(12) United States Patent
Bolli et al.

(10) Patent No.: US 9,403,813 B2
(45) Date of Patent: Aug. 2, 2016

(54) AZETIDINE AMIDE DERIVATIVES AS OREXIN RECEPTOR ANTAGONISTS

(71) Applicant: ACTELION PHARMACEUTICALS LTD, Alschwil (CH)

(72) Inventors: Martin Bolli, Allschwil (CH);
Christoph Boss, Allschwil (CH);
Christine Brotschi, Allschwil (CH);
Bibia Heidmann, Allschwil (CH);
Thierry Sifferlen, Allschwil (CH); Jodi T. Williams, Allschwil (CH)

(73) Assignee: ACTELION PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 14/775,474

(22) PCT Filed: Mar. 11, 2014

(86) PCT No.: PCT/IB2014/059628
§ 371 (c)(1),
(2) Date: Sep. 11, 2015

(87) PCT Pub. No.: WO2014/141065
PCT Pub. Date: Sep. 18, 2014

(65) Prior Publication Data
US 2016/0024064 A1  Jan. 28, 2016

(30) Foreign Application Priority Data
Mar. 12, 2013 (EP) ..................................... 13158791

(51) Int. Cl.
| | | |
|---|---|---|
| *C07D 413/14* | (2006.01) | |
| *C07D 403/04* | (2006.01) | |
| *C07D 417/14* | (2006.01) | |
| *C07D 403/14* | (2006.01) | |
| *C07D 401/14* | (2006.01) | |
| *C07D 413/04* | (2006.01) | |

(52) U.S. Cl.
CPC ............ *C07D 413/14* (2013.01); *C07D 401/14* (2013.01); *C07D 403/04* (2013.01); *C07D 403/14* (2013.01); *C07D 413/04* (2013.01); *C07D 417/14* (2013.01)

(58) Field of Classification Search
CPC .. C07D 413/14; C07D 403/04; C07D 417/14; C07D 403/14; C07D 401/14; C07D 413/04
See application file for complete search history.

(56) References Cited

U.S. PATENT DOCUMENTS

| | | | |
|---|---|---|---|
| 6,660,759 B1 | 12/2003 | Hattori et al. | |
| 7,763,638 B2 | 7/2010 | Aissaoui et al. | |
| 7,994,336 B2 | 8/2011 | Aissaoui et al. | |
| 8,063,099 B2 | 11/2011 | Aissaoui et al. | |
| 8,106,215 B2 | 1/2012 | Aissaoui et al. | |
| 8,133,901 B2 | 3/2012 | Aissaoui et al. | |
| 8,236,801 B2 | 8/2012 | Aissaoui et al. | |
| 8,236,964 B2 | 8/2012 | Aissaoui et al. | |
| 8,288,411 B2 | 10/2012 | Aissaoui et al. | |
| 8,288,429 B2 | 10/2012 | Aissaoui et al. | |
| 8,288,435 B2 | 10/2012 | Aissaoui et al. | |
| 9,150,566 B2 | 10/2015 | Bolli et al. | |
| 2005/0014765 A1 | 1/2005 | Mailliet et al. | |
| 2006/0019975 A1 | 1/2006 | Humphrey et al. | |
| 2009/0082394 A1 | 3/2009 | Jenck | |
| 2010/0016401 A1 | 1/2010 | Aissaoui et al. | |
| 2010/0222328 A1 | 9/2010 | Aissaoui et al. | |
| 2010/0234420 A1 | 9/2010 | Jenck | |
| 2011/0105491 A1 | 5/2011 | Aissaoui et al. | |
| 2011/0212968 A1 | 9/2011 | Aissaoui et al. | |
| 2015/0166527 A1 | 6/2015 | Boss et al. | |
| 2015/0252032 A1 | 9/2015 | Bolli et al. | |

FOREIGN PATENT DOCUMENTS

| | | |
|---|---|---|
| JP | 2001 247569 | 9/2001 |
| WO | WO 2001/096302 | 12/2001 |
| WO | WO 2002/044172 | 6/2002 |
| WO | WO 2002/089800 | 11/2002 |
| WO | WO 2002/090355 | 11/2002 |
| WO | WO 2003/002559 | 1/2003 |
| WO | WO 2003/002561 | 1/2003 |
| WO | WO 2003/032991 | 4/2003 |
| WO | WO 2003/041711 | 5/2003 |

(Continued)

OTHER PUBLICATIONS

Written Opinion of the ISR, PCT/IB2014/059628, Dec. 9, 2015.*

(Continued)

*Primary Examiner* — Matthew Coughlin
(74) *Attorney, Agent, or Firm* — Hoxie & Associates LLC

(57) ABSTRACT

The present invention relates to azetidine amide derivatives derivatives of formula (I)

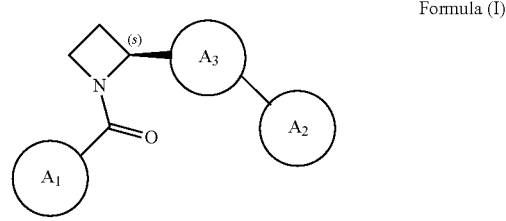

Formula (I)

wherein rings $A_1$ $A_2$ and $A_3$ are as described in the description, to pharmaceutically acceptable salts thereof, to their preparation, to pharmaceutical compositions containing one or more compounds of formula (I), and to their use as pharmaceuticals, especially to their use as orexin receptor antagonists.

12 Claims, No Drawings

(56) References Cited

FOREIGN PATENT DOCUMENTS

| | | |
|---|---|---|
| WO | WO 2003/051368 | 6/2003 |
| WO | WO 2003/051873 | 6/2003 |
| WO | WO 2004/024725 | 3/2004 |
| WO | WO 2004/026866 | 4/2004 |
| WO | WO 2004/041791 | 5/2004 |
| WO | WO 2004/041807 | 5/2004 |
| WO | WO 2004/041816 | 5/2004 |
| WO | WO 2005/044797 | 5/2005 |
| WO | WO 2005/113522 | 12/2005 |
| WO | WO 2005/121131 | 12/2005 |
| WO | WO 2006/012349 | 2/2006 |
| WO | WO 2006/123249 | 11/2006 |
| WO | WO 2007/039781 | 4/2007 |
| WO | WO 2008/008517 | 1/2008 |
| WO | WO 2008/020405 | 2/2008 |
| WO | WO 2008/069997 | 6/2008 |
| WO | WO 2008/087611 | 7/2008 |
| WO | WO 2008/144380 | 11/2008 |
| WO | WO 2008/150364 | 12/2008 |
| WO | WO 2009/003993 | 1/2009 |
| WO | WO 2009/003997 | 1/2009 |
| WO | WO 2009/077990 | 6/2009 |
| WO | WO 2009/124956 | 10/2009 |
| WO | WO 2010/038200 | 4/2010 |
| WO | WO 2010/048012 | 4/2010 |
| WO | WO 2010/060470 | 6/2010 |
| WO | WO 2010/060471 | 6/2010 |
| WO | WO 2010/060472 | 6/2010 |
| WO | WO 2010/063662 | 6/2010 |
| WO | WO 2010/063663 | 6/2010 |
| WO | WO 2010/072722 | 7/2010 |
| WO | WO 2010/114978 | 10/2010 |
| WO | WO 2010/122151 | 10/2010 |
| WO | WO 2010/143116 | 12/2010 |
| WO | WO 2011/050198 | 4/2011 |
| WO | WO 2011/050200 | 4/2011 |
| WO | WO 2011/050202 | 4/2011 |
| WO | WO 2011/090911 | 7/2011 |
| WO | WO 2012/039717 | 3/2012 |

OTHER PUBLICATIONS

Packiarajan et al. Bioorg. Med. Chem. Lett. 2012, 22, 6469-6474.*
Adam et al., Physiol Behav, 91(4) 449-458; 2007.
Aston-Jones et al., Brain Res, 1314, 74-90; 2010.
Berridge et al., Brain Res, 1314, 91-102; 2009.
Borgland et al., Neuron, 49(4), 589-601; 2006.
Boss et al., Journal of Medicinal Chemistry, 52: 891-903, 2009.
Boutrel et al., Proc Natl Acad Sci, 102(52), 19168-19173; 2005.
Brisbare et al., Nature Medicine, 13, 150-155, 2007.
Carter et al., Curr Op Pharmacol., 9, 39-45, 2009.
Chemelli et al., Cell, 98, 437-451, 1999.
Chrousos et al., Jama, 267(9), 1244-1252; 1992.
Dietrich, Psychopharmacology, 212, 145-154; 2010.
Fendt et al., Neuroscience Biobehav Rev, 23, 743-760; 1999.
Feng et al., J Psychopharmacol, 22(7), 784-791, 2008.
Furlong et al., Eur J Neurosci, 30(8), 1603-1614; 2009.
Gould; Int J Pharm, 33, 201-217, 1986.
Gozzi et al., PLoS One, 6(1), e16406; 2011.
Greene et al., "Protective Groups in Organic Synthesis", Wiley-Interscience, 1999.
Hollander et al., Proc Natl Acad Sci, 105(49), 19480-19485; 2008.
Hutcheson et al., Behav Pharmacol, 22(2), 173-181; 2011.
International Search Report of PCT Application No. PCT/IB2013/059233 mailed Feb. 27, 2014.
Kang et al., Science, 326(5955): 1005-1007; 2009.
Kayaba et al., Am. J. Physiol. Regul. Integr. Comp. Physiol., 285:R581-593; 2003.
Koob et al., Curr Opin Investig Drugs, 11(1), 63-71, 2010.
Lamb, Bioorganic & Medicinal Chemistry Letters; vol. 21, p. 2711-2714; Dec. 3, 2010.
Langmead et al.; Brit J Pharmacol, 141, 340-346; 2004.
Lawrence et al., Br J Pharrnacol, 148(6), 752-759; 2006.
LeSage et al., Psychopharmacology, 209(2), 203-212; 2010.
Liu et al., Sleep, 30(1): 83-90; 2007.
Lucca et al., J. Med. Chem., 2411-2423; 1998.
Majzoub et al., European Journal of Endocrinology, 155 (suppl_1) S71-S76; 2006.
Mathes et al.; Appetite, 52, 545-553, 2009.
Moorthy et al., J. Org. Chem, 9786-9; 2007.
National Center for Biotechnology Information. PubChem Compound Database; CID=16672186, https://pubchem.ncbi.nlm.nih.gov/ compound/16672186 (accessed Feb. 25, 2016).
Nollet et al., NeuroPharrn, 61(1-2), 336-46, 2011.
Panetta et al., J Org Chem, 64(3), 1015-1021; 1999.
Powers et al., Tetrahedron Letters, 1267-1269; 2009.
Prud'homrne et al., Neuroscience, 162(4), 1287-1298; 2009.
Quarta et al., Neurochem Int, 56(1), 11-15; 2010.
Remington, The Science and Practice of Pharmacy, 21st Edition, Part 5, Pharmaceutical Manufacturing; 2005.
Sakurai et al., Cell, 92, 573-585; 1998.
Salomon et al., Biol Psychiatry, 54(2), 96-104, 2003.
Sharf et al., Brain Res., 1314, 130-138; 2010.
Shippenberg, Neuropsychopharmcalogy; Chapter 97, 1381-1397; 2002.
Smith et al., Eur J Neurosci, 30(3), 493-503; 2009.
Smith et al., Neuropharmacology, 58(1), 179-184; 2010.
Spealman et al, Pharmacol. Biochem. Behav., 64, 327-336; 1999.
Stahl et al., Handbook of Pharmaceutical Salts: Properties, Selection and Use; 2008.
Stickgold et al., Nature, 437, 1272-1278; 2005.
Sutcliffe et al., Nat Rev Neurosci, 3(5), 339-349; 2002.
Tsujino; Pharmacol Rev., 61, 162-176, 2009.
Vanderschuren et al., Current Topics in Behavioral Neurosciences 3, 179-195; 2009.
Vinkers et al., European J Pharmacol, 585, 407-425; 2008.
Winrow et al., Neuropharmacology, 58(1),185-94, 2009.
Wouters et al., Pharmaceutical Salts and Cocrystals, 2012.
Zhang et al., Auton Neurosci, 126-127, 139-145, 2006.

* cited by examiner

AZETIDINE AMIDE DERIVATIVES AS OREXIN RECEPTOR ANTAGONISTS

CROSS-REFERENCE TO RELATED APPLICATIONS

This application is a National Stage Entry of International Application No. PCT/IB2014/059628, filed on Mar. 11, 2014, which claims priority from European Patent Application No. 13158791.7, filed on Mar. 12, 2013, the contents of each of which are hereby incorporated by reference in their entirety.

The present invention relates to novel azetidine amide derivatives and their use as pharmaceuticals. The invention also concerns related aspects including processes for the preparation of the compounds, pharmaceutical compositions containing one or more compounds of formula (I) or (II), and especially their use as orexin receptor antagonists.

Orexins (orexin A or OX-A and orexin B or OX-B) are neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexin receptor antagonists are a novel type of nervous system or psychotropic drugs. Their mode of action in animals and humans involves either blockade of both orexin-1 and orexin-2 receptor (dual antagonists), or individual and selective blockade of either the orexin-1 or the orexin-2 receptor (selective antagonists) in the brain. Orexins were initially found to stimulate food consumption in rats suggesting a physiological role for these peptides as mediators in the central feedback mechanism that regulates feeding behaviour (Sakurai T. et al., Cell, 1998, 92, 573-585).

On the other hand, orexin neuropeptides and orexin receptors play an essential and central role in regulating circadian vigilance states. In the brain, orexin neurons collect sensory input about internal and external states and send short intra-hypothalamic axonal projections as well as long projections to many other brain regions. The particular distribution of orexin fibers and receptors in basal forebrain, limbic structures and brainstem regions—areas related to the regulation of waking, sleep and emotional reactivity—suggests that orexins exert essential functions as regulators of behavioral arousal; by activating wake-promoting cell firing, orexins contribute to orchestrate all brain arousal systems that regulate circadian activity, energy balance and emotional reactivity. This role opens large therapeutic opportunities for medically addressing numerous mental health disorders possibly relating to orexinergic dysfunctions [see for example: Tsujino N and Sakurai T, "Orexin/hypocretin: a neuropeptide at the interface of sleep, energy homeostasis, and reward systems.", Pharmacol Rev. 2009, 61:162-176; and Carter M E et al., "The brain hypocretins and their receptors: mediators of allostatic arousal.", Curr Op Pharmacol. 2009, 9: 39-45] that are described in the following sections. It was also observed that orexins regulate states of sleep and wakefulness opening potentially novel therapeutic approaches to insomnia and other sleep disorders (Chemelli R. M. et al., Cell, 1999, 98, 437-451).

Human memory is comprised of multiple systems that have different operating principles and different underlying neuronal substrates. The major distinction is between the capacity for conscious, declarative memory and a set of unconscious, non-declarative memory abilities. Declarative memory is further subdivided into semantic and episodic memory. Non-declariative memory is further subdivided into priming and perceptual learning, procedural memory for skills and habits, associative and non-associative learning, and some others. While semantic memory refers to the general knowledge about the world, episodic memory is autobiographical memory of events. Procedural memories refer to the ability to perform skill-based operations, as e.g. motor skills. Long-term memory is established during a multiple stage process through gradual changes involving diverse brain structures, beginning with learning, or memory acquisition, or formation. Subsequently, consolidation of what has been learned may stabilize memories. When long-term memories are retrieved, they may return to a labile state in which original content may be updated, modulated or disrupted. Subsequently, reconsolidation may again stabilize memories. At a late stage, long-term memory may be resistant to disruption. Long-term memory is conceptually and anatomically different from working memory, the latter of which is the capacity to maintain temporarily a limited amount of information in mind. Behavioural research has suggested that the human brain consolidates long-term memory at certain key time intervals. The initial phase of memory consolidation may occur in the first few minutes after we are exposed to a new idea or learning experience. The next, and possibly most important phase, may occur over a longer period of time, such as during sleep; in fact, certain consolidation processes have been suggested to be sleep-dependent [R. Stickgold et al., Sleep-dependent memory consolidation; Nature 2005, 437, 1272-1278]. Learning and memory processes are believed to be fundamentally affected in a variety of neurological and mental disorders, such as e.g. mental retardation, Alzheimer's disease or depression. Indeed, memory loss or impairment of memory acquisition is a significant feature of such diseases, and no effective therapy to prevent this detrimental process has emerged yet.

In addition, both anatomical and functional evidence from in vitro and in vivo studies suggest an important positive interaction of the endogenous orexin system with reward pathways of the brain [Aston-Jones G et al., Brain Res 2010, 1314, 74-90; Sharf R et al., Brain Res 2010, 1314, 130-138]. Selective pharmacological OXR-1 blockade reduced cue- and stress-induced reinstatement of cocaine seeking [Boutrel B, et al., "Role for hypocretin in mediating stress-induced reinstatement of cocaine-seeking behavior." Proc Natl Acad Sci 2005, 102(52), 19168-19173; Smith R J et al., "Orexin/hypocretin signaling at the orexin 1 receptor regulates cue-elicited cocaine-seeking." Eur J Neurosci 2009, 30(3), 493-503; Smith R J et al., "Orexin/hypocretin is necessary for context-driven cocaine-seeking." Neuropharmacology 2010, 58(1), 179-184], cue-induced reinstatement of alcohol seeking [Lawrence A J et al., Br J Pharmacol 2006, 148(6), 752-759] and nicotine self-administration [Hollander J A et al., Proc Natl Acad Sci 2008, 105(49), 19480-19485; LeSage M G et al., Psychopharmacology 2010, 209(2), 203-212]. Orexin-1 receptor antagonism also attenuated the expression of amphetamine- and cocaine-induced CPP [Gozzi A et al., PLoS One 2011, 6(1), e16406; Hutcheson D M et al., Behav Pharmacol 2011, 22(2), 173-181], and reduced the expression or development of locomotor sensitization to amphetamine and cocaine [Borgland S L et al., Neuron 2006, 49(4), 589-601; Quarta D et al., "The orexin-1 receptor antagonist SB-334867 reduces amphetamine-evoked dopamine outflow in the shell of the nucleus accumbens and decreases the expression of amphetamine sensitization." Neurochem Int 2010, 56(1), 11-15].

The effect of a drug to diminish addictions may be modelled in normal or particularly sensitive mammals used as animal models [see for example Spealman et al, Pharmacol. Biochem. Behav. 1999, 64, 327-336; or T. S. Shippenberg, G. F. Koob, "Recent advances in animal models of drug addiction" in Neuropsychopharmacology: The fifth generation of progress; K. L. Davis, D. Charney, J. T. Doyle, C. Nemeroff (eds.) 2002; chapter 97, pages 1381-1397].

Several converging lines of evidence furthermore demonstrate a direct role of the orexin system as modulator of the acute stress response. For instance, stress (i.e. psychological stress or physical stress) is associated with increased arousal and vigilance which in turn is controlled by orexins [Sutcliffe, J G et al., Nat Rev Neurosci 2002, 3(5), 339-349]. Orexin neurons are likely to be involved in the coordinated regulation of behavioral and physiological responses in stressful environments [Y. Kayaba et al., Am. J. Physiol. Regul. Integr. Comp. Physiol. 2003, 285:R581-593]. Hypocretin/orexin contributes to the expression of some but not all forms of stress and arousal [Furlong T M et al., Eur J Neurosci 2009, 30(8), 1603-1614]. Stress response may lead to dramatic, usually time-limited physiological, psychological and behavioural changes that may affect appetite, metabolism and feeding behavior [Chrousos, G P et al., JAMA 1992, 267(9), 1244-1252]. The acute stress response may include behavioural, autonomic and endocrinological changes, such as promoting heightened vigilance, decreased libido, increased heart rate and blood pressure, or a redirection of blood flow to fuel the muscles, heart and the brain [Majzoub, J A et al., European Journal of Endocrinology 2006, 155 (suppl_1) S71-S76].

As outlined above the orexin system regulates homeostatic functions such as sleep-wake cycle, energy balance, emotions and reward. Orexins are also involved in mediating the acute behavioral and autonomous nervous system response to stress [Zhang W et. al., "Multiple components of the defense response depend on orexin: evidence from orexin knockout mice and orexin neuron-ablated mice." Auton Neurosci 2006, 126-127, 139-145]. Mood disorders including all types of depression and bipolar disorder are characterized by disturbed "mood" and feelings, as well as by sleeping problems (insomnia as well as hypersomnia), changes in appetite or weight and reduced pleasure and loss of interest in daily or once enjoyed activities [Liu X et al., Sleep 2007, 30(1): 83-90]. Thus, there is a strong rationale that disturbances in the orexin system may contribute to the symptoms of mood disorders. Evidence in humans, for instance, exists that depressed patients show blunted diurnal variation in CSF orexin levels [Salomon R M et al., Biol Psychiatry 2003, 54(2), 96-104]. In rodent models of depression, orexins were also shown to be involved. Pharmacological induction of a depressive behavioral state in rats, for instance, revealed an association with increased hypothalamic orexin levels [Feng P et al., J Psychopharmacol 2008, 22(7): 784-791]. A chronic stress model of depression in mice also demonstrated an association of molecular orexin system disturbances with depressed behavioral states and a reversal of these molecular changes by antidepressant treatment [Nollet et al., NeuroPharm 2011, 61(1-2):336-46].

The orexin system is also involved in stress-related appetitive/reward seeking behaviour (Berridge C W et al., Brain Res 2009, 1314, 91-102). In certain instances, a modulatory effect on stress may be complementary to an effect on appetitive/reward seeking behaviour as such. For instance, an $OX_1$ selective orexin receptor antagonist was able to prevent footshock stress induced reinstatement of cocaine seeking behaviour [Boutrel, B et al., Proc Natl Acad Sci 2005, 102(52), 19168-19173]. In addition, stress is also known to play an integral part in withdrawal which occurs during cessation of drug taking (Koob, G F et al., Curr Opin Investig Drugs 2010, 11(1), 63-71).

Orexins have been found to increase food intake and appetite [Tsujino, N, Sakurai, T, Pharmacol Rev 2009, 61(2) 162-176]. As an additional environmental factor, stress can contribute to binge eating behaviour, and lead to obesity [Adam, T C et al. Physiol Behav 2007, 91(4) 449-458]. Animal models that are clinically relevant models of binge eating in humans are described for example in W. Foulds Mathes et al.; Appetite 2009, 52, 545-553.

A number of recent studies report that orexins may play a role into several other important functions relating to arousal, especially when an organism must respond to unexpected stressors and challenges in the environment [Tsujino N and Sakurai T. Pharmacol Rev. 2009, 61:162-176; Carter M E, Borg J S and deLecea L., Curr Op Pharmacol. 2009, 9: 39-45; C Boss, C Brisbare-Roch, F Jenck, Journal of Medicinal Chemistry 2009, 52: 891-903]. The orexin system interacts with neural networks that regulate emotion, reward and energy homeostasis to maintain proper vigilance states. Dysfunctions in its function may thus relate to many mental health disorders in which vigilance, arousal, wakefulness or attention is disturbed.

The compound (2R)-2-{(1S)-6,7-dimethoxy-1-[2-(4-trifluoromethyl-phenyl)-ethyl]-3,4-dihydro-1H-isoquinolin-2-yl}-N-methyl-2-phenyl-acetamide (WO2005/118548), a dual orexin receptor antagonist, showed clinical efficacy in humans when tested for the indication primary insomnia. In the rat, the compound has been shown to decrease alertness, characterized by decreases in both active wake and locomotion; and to dose-dependently increase the time spent in both REM and NREM sleep [Brisbare et al., Nature Medicine 2007, 13, 150-155]. The compound further attenuated cardiovascular responses to conditioned fear and novelty exposure in rats [Furlong T M et al., Eur J Neurosci 2009, 30(8), 1603-1614]. It is also active in an animal model of conditioned fear: the rat fear-potentiated startle paradigm (WO2009/047723) which relates to emotional states of fear and anxiety diseases such as anxieties including phobias and post traumatic stress disorders (PTSDs). In addition, intact declarative and non-declarative learning and memory has been demonstrated in rats treated with this compound [WO2007/105177, H Dietrich, F Jenck, Psychopharmacology 2010, 212, 145-154]. Said compound furthermore decreased brain levels of amyloid-beta (Aβ) as well as Aβ plaque deposition after acute sleep restriction in amyloid precursor protein transgenic mice [J E Kang et al., "Amyloid-beta dynamics are regulated by orexin and the sleep-wake cycle.", Science 2009, 326(5955): 1005-1007]. The accumulation of the Aβ in the brain extracellular space is hypothesized to be a critical event in the pathogenesis of Alzheimer's disease. The so-called and generally known "amyloid cascade hypothesis" links Aβ to Alzheimer's disease and, thus, to the cognitive dysfunction, expressed as impairment of learning and memory. The compound has also been shown to induce antidepressant-like activity in a mouse model of depression, when administered chronically [Nollet et al., NeuroPharm 2011, 61(1-2):336-46]. Moreover, the compound has been shown to attenuate the natural activation induced by orexin A in fasted hungry rats exposed to food odors [M J Prud'homme et al., Neuroscience 2009, 162(4), 1287-1298]. The compound also displayed pharmacological activity in a rat model of nicotine self-administration [LeSage M G et al., Psychopharmacology 2010, 209(2), 203-212]. N-Biphenyl-2-yl-1-{[(1-methyl-1H-benzimidazol-2-yl)sulfanyl]acetyl}-L-prolinamide, another dual orexin receptor antagonist, inhibited nicotine-reinstatement for a conditioned reinforcer and reduced behavioral (locomotor sensitization) and molecular (transcriptional responses) changes induced by repeated amphetamine administration in rodents [Winrow et al., Neuropharmacology 2009, 58(1), 185-94].

Orexin receptor antagonists comprising a 2-substituted saturated cyclic amide derivatives are known for example from WO2008/038251, WO2008/081399, WO2008/087611, WO2008/117241, WO2008/139416, WO2009/004584, WO2009/016560, WO2009/016564, WO2009/040730, WO2009/104155, WO2010/004507, WO2010/038200, WO2001/096302, WO2002/044172, WO2002/089800, WO2002/090355, WO2003/002559, WO2003/002561, WO2003/032991, WO2003/041711, WO2003/051368, WO2003/051873, WO2004/026866, WO2004/041791, WO2004/041807, WO2004/041816, WO2009/003993, WO2009/003997, WO2009/124956, WO2010/060470, WO2010/060471, WO2010/060472, WO2010/063662, WO2010/063663, WO2010/072722, WO2010/122151, and WO2008/150364. WO2008/020405 discloses certain azetidine compounds as orexin receptor antagonists. Despite the great number of prior art compounds and their high structural variability, all compounds share a common structural feature, i.e. in position 2 of the saturated cyclic amide a linker group such as at least a methylene group (or longer groups such as —CH$_2$—NH—CO— (as in WO2008/020405), —CH$_2$—NH—, —CH$_2$—O—, —CH$_2$—S—, etc.) link the cyclic amide to the respective aromatic ring system substituent. It has now surprisingly been found that, despite the substantial conformational and, thus, pharmacological changes that may be expected from the removal of a linker between two rigid structural elements, the present compounds, that have an aromatic ring system directly attached to an azetidine amide in position 2, are orexin receptor antagonists which may be active especially on the orexin-2 receptor.

The present invention, thus, provides novel azetidine amide derivatives of formula (I) which are non-peptide antagonists of human orexin receptors potentially useful in the treatment of disorders relating to orexinergic dysfunctions, comprising especially sleep disorders, anxiety disorders, addiction disorders, cognitive dysfunctions, mood disorders, or appetite disorders; and especially in the treatment of sleep disorders, anxiety disorders, and addiction disorders.

1) A first aspect of the invention relates to compounds of the formula (I),

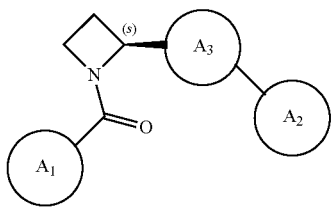

Formula (I)

wherein the carbon atom at position 2 of the azetidine ring is in absolute (S)-configuration;
ring A$_3$ represents a meta di-substituted 5-membered heteroarylene ring containing one, two or three heteroatoms; wherein at least one of said heteroatoms is nitrogen, and the remaining is/are independently selected from oxygen, sulfur and nitrogen; [wherein it is understood that the two meta-arranged substituents are the azetidin-2-yl group and the substituent A$_2$; and that the ring A$_3$ does not carry any further substituent];
ring A$_2$ represents phenyl or 6-membered heteroaryl; wherein said phenyl or 6-membered heteroaryl is independently unsubstituted, or mono-, di-, or tri-substituted; wherein the substituents are independently selected from (C$_{1-4}$)alkyl, (C$_{1-4}$)alkoxy, halogen, (C$_{1-3}$)fluoroalkyl, (C$_{1-3}$)fluoroalkoxy, and (C$_{3-6}$)cycloalkyl-oxy-;
ring A$_1$ represents phenyl or 5- or 6-membered heteroaryl, wherein said phenyl or 5- or 6-membered heteroaryl independently is mono-, di-, or tri-substituted; wherein
  one of said substituents is attached in ortho-position to the point of attachment of A$_1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from (C$_{1-4}$)alkyl, (C$_{1-4}$)alkoxy, halogen, (C$_{1-3}$)fluoroalkyl, and (C$_{1-3}$)fluoroalkoxy;
  and the other of said substituents, if present, is/are independently selected from (C$_{1-4}$)alkyl, (C$_{1-4}$)alkoxy, halogen, (C$_{1-3}$)fluoroalkyl, (C$_{1-3}$)fluoroalkoxy and dimethylamino.

2) A further embodiment of the invention relates to compounds according to embodiment 1), wherein the ring A$_3$ represents a ring

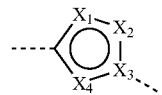

wherein said ring is a meta di-substituted 5-membered heteroarylene ring containing one, two or three heteroatoms at any of the positions X$_1$, X$_2$, X$_3$, and/or X$_4$; wherein at least one of said heteroatoms is nitrogen, and the remaining, if present, is/are independently selected from oxygen, sulfur and nitrogen.

3) A further embodiment of the invention relates to compounds according to embodiment 1), wherein the ring A$_3$ represents a ring

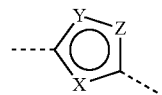

wherein said ring is a meta di-substituted 5-membered heteroarylene ring containing one, two or three heteroatoms at any of the positions X, Y and/or Z; wherein at least one of said heteroatoms is nitrogen, and the remaining, if present, is/are independently selected from oxygen, sulfur and nitrogen.

4) A further embodiment of the invention relates to compounds according to embodiment 1), wherein the ring A$_3$ is a meta di-substituted 5-membered heteroarylene ring selected from oxadiazol-diyl, triazol-diyl, isoxazol-diyl, oxazol-diyl, thiazol-diyl, pyrazol-diyl, imidazol-diyl, isothiazol-diyl, and thiadiazol-diyl (especially oxadiazol-diyl, or triazol-diyl).

5) A further embodiment of the invention relates to compounds according to embodiment 1), wherein the ring A$_3$ is selected from [1,2,4]oxadiazol-3,5-diyl, [1,2,4]triazol-3,5-diyl, [1,2,4]triazol-1,3-diyl, 1H-pyrazol-3,5-diyl, imidazol-2,4-diyl, isoxazol-3,5-diyl, oxazol-2,4-diyl, oxazol-2,5-diyl, thiazol-2,4-diyl, thiazol-2,5-diyl, isothiazol-3,5-diyl, [1,3,4]thiadiazol-2,5-diyl, and [1,3,4]oxadiazol-2,5-diyl (especially [1,2,4]oxadiazol-3,5-diyl, or [1,2,4]triazol-3,5-diyl).

6) A further embodiment of the invention relates to compounds of formula (I) according to embodiment 1), wherein the ring A₃ represents

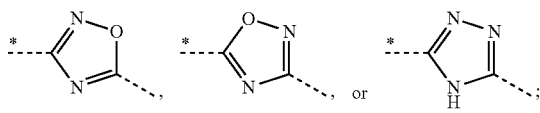

wherein the asterisks indicate the bond that is linked to the azetidin-2-yl moiety of the molecule.

7) A further embodiment of the invention relates to compounds of formula (I) according to embodiment 1), wherein the ring A₃ represents:

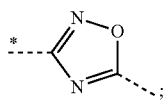

wherein the asterisks indicate the bond that is linked to the azetidin-2-yl moiety of the molecule.

8) A further embodiment of the invention relates to compounds of formula (I) according to embodiment 1), wherein the ring A₃ represents:

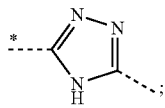

wherein the asterisks indicate the bond that is linked to the azetidin-2-yl moiety of the molecule.

9) A further embodiment of the invention relates to compounds of formula (I) according to embodiment 1), wherein the ring A₃ represents

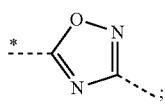

wherein the asterisks indicate the bond that is linked to the azetidin-2-yl moiety of the molecule.

10) A further embodiment relates to compounds of formula (I) according to any one of embodiments 1) to 9), wherein ring A₂ represents
   phenyl which is unsubstituted, or mono-, di-, or tri-substituted (especially unsubstituted, or mono- or di-substituted); wherein the substituents are independently selected from the group consisting of $(C_{1-4})$alkyl, $(C_{1-4})$alkoxy, $(C_{3-6})$cycloalkyl, halogen, $(C_{1-3})$fluoroalkyl, $(C_{1-3})$fluoroalkoxy; and $(C_{3-6})$cycloalkyl-oxy-; or
   6-membered heteroaryl (especially 6-membered heteroaryl containing one or two ring nitrogen atoms; notably pyridinyl); wherein said heteroaryl is independently unsubstituted, or mono-, or di-substituted (especially mono-substituted); wherein the substituents are independently selected from $(C_{1-4})$alkyl, $(C_{1-4})$alkoxy, halogen, $(C_{1-3})$fluoroalkyl, $(C_{1-3})$fluoroalkoxy, and $(C_{3-6})$cycloalkyl-oxy- (especially $(C_{1-4})$alkoxy, and $(C_{3-6})$cycloalkyl-oxy-).

11) A further embodiment relates to compounds of formula (I) according to any one of embodiments 1) to 9), wherein ring A₂ represents
   phenyl which is mono- or di-substituted; wherein the substituents are independently selected from $(C_{1-4})$alkyl, $(C_{1-4})$alkoxy, halogen, and $(C_{1-3})$fluoroalkoxy; or
   6-membered heteroaryl containing one or two ring nitrogen atoms (especially pyridinyl); wherein said heteroaryl is mono-substituted; wherein the substituent is selected from $(C_{1-4})$alkoxy and $(C_{3-6})$cycloalkyl-oxy-; wherein preferably said substituent is attached in ortho-position with respect to the point of attachment of the rest of the molecule.

12) A further embodiment relates to compounds of formula (I) according to any one of embodiments 1) to 9), wherein ring A₂ represents
   phenyl which is unsubstituted, or mono-, di-, or tri-substituted (especially mono- or di-substituted); wherein the substituents are independently selected from methyl, methoxy, ethoxy, n-propoxy, fluoro, chloro, and trifluoromethoxy; or
   pyridinyl which is mono-substituted; wherein the substituent is ethoxy or cyclobutyl-oxy-.

13) A further embodiment relates to compounds of formula (I) according to embodiment 1), wherein the group A₃-A₂ represents a group independently selected from the following groups A, B and C:

A: [1,2,4]oxadiazol-3,5-diyl groups selected from the groups:

A.1

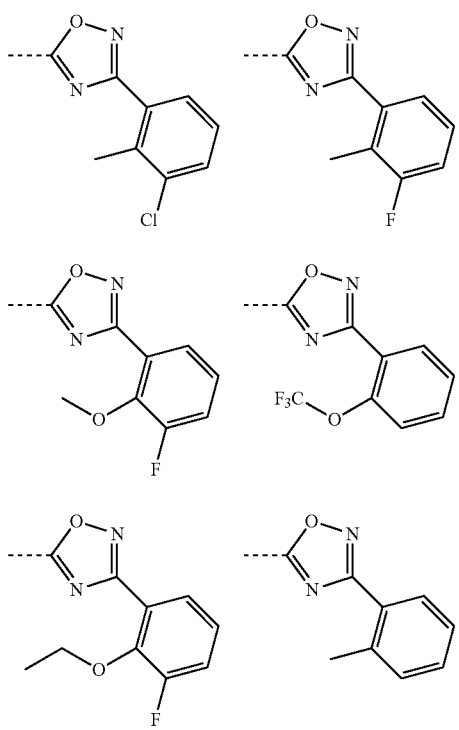

-continued
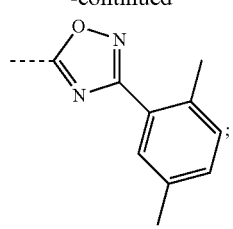
A.2
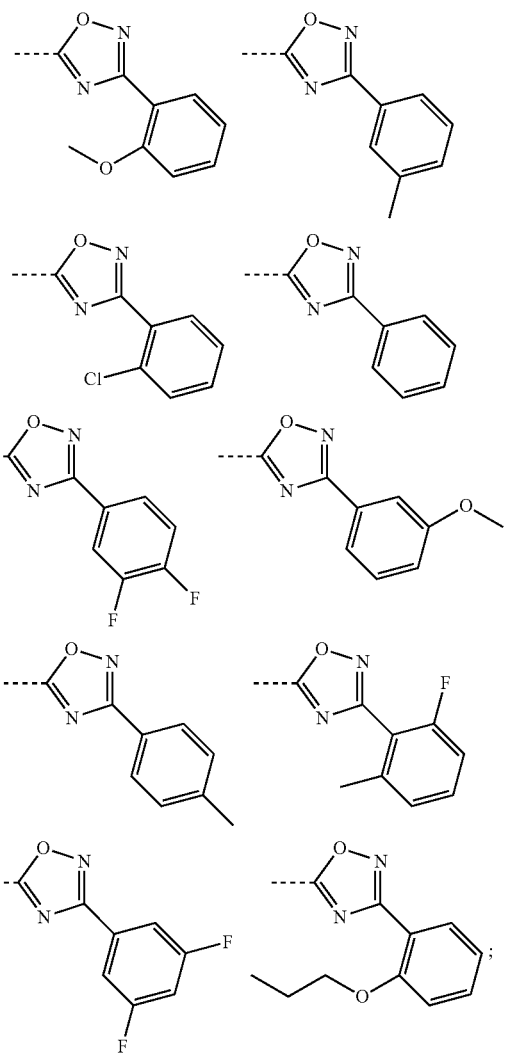
A.3
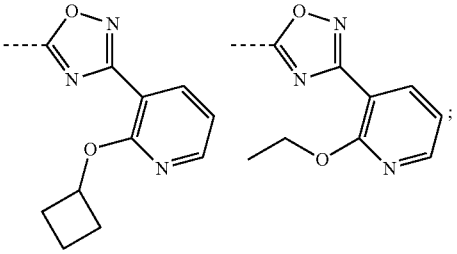
B: [1,2,4]oxadiazol-3,5-diyl groups selected from the groups:
B.1
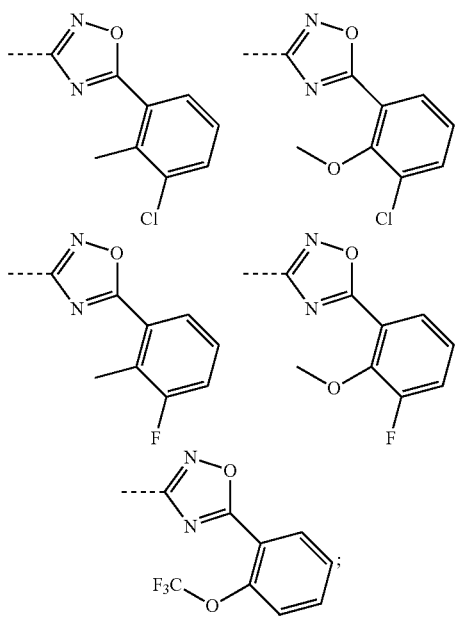
B.2
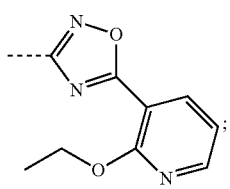
B.3
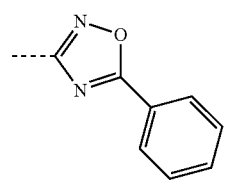
C: [1,2,4]triazol-3,5-diyl groups selected from the groups:
C.1
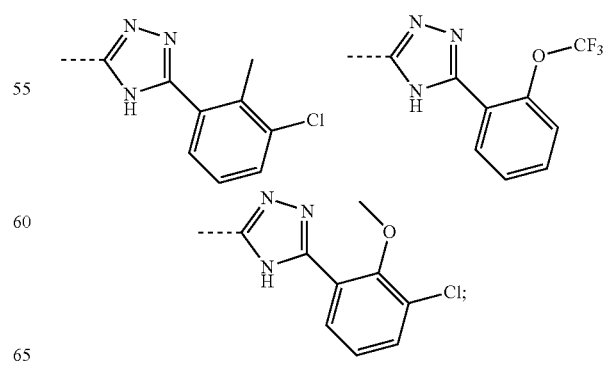

C.2

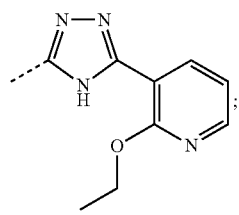

C.3

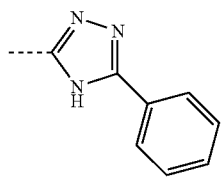

wherein each of the groups A, B, and C and their respective subgroups forms a particular sub-embodiment.

14) A further embodiment relates to compounds of formula (I) according to embodiment 1), wherein the group $A_3$-$A_2$ represents a group independently selected from the following groups A, B and C:

A: [1,2,4]oxadiazol-3,5-diyl groups selected from the groups:

A.1

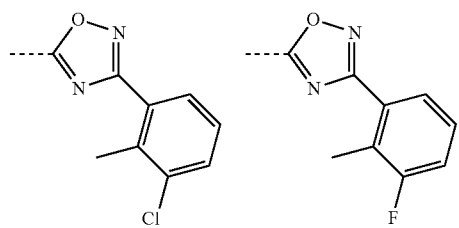

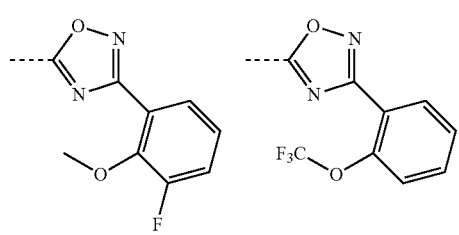

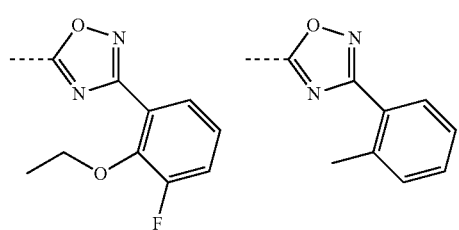

A.2

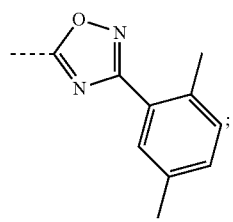

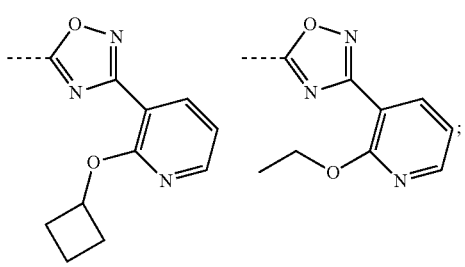

B: [1,2,4]oxadiazol-3,5-diyl groups selected from the groups:

B.1

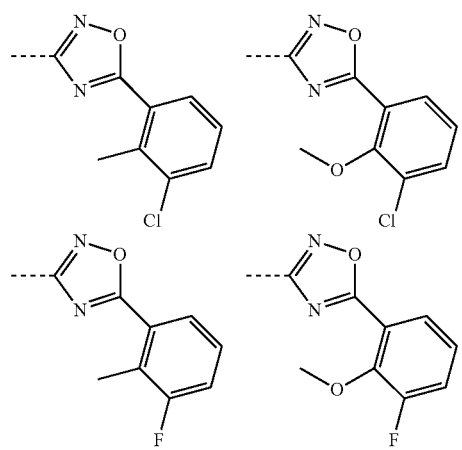

B.2

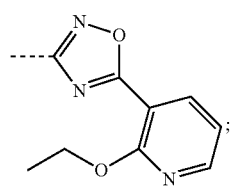

C: [1,2,4]triazol-3,5-diyl groups selected from the groups:
C.1

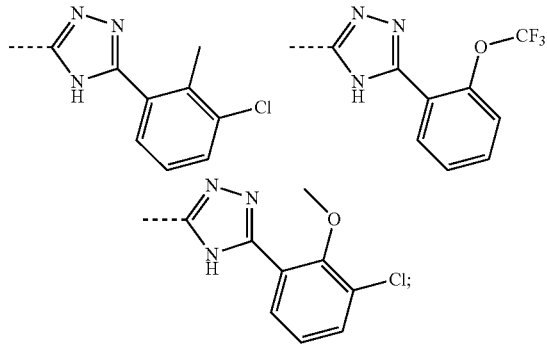

C.2

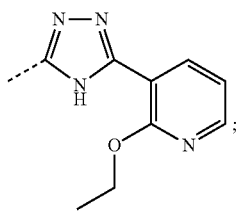

wherein each of the groups A, B, and C and their respective subgroups forms a particular sub-embodiment.

15) A further embodiment relates to compounds of formula (I) according to any one of embodiments 1) to 14), wherein ring $A_1$ represents phenyl or 5- or 6-membered heteroaryl, wherein said phenyl or 5- or 6-membered heteroaryl independently is mono-, di-, or tri-substituted; wherein
  one of said substituents is attached in ortho-position to the point of attachment of $A_1$ to the rest of the molecule; wherein said substituent is phenyl or 5- or 6-membered heteroaryl; wherein said phenyl or 5- or 6-membered heteroaryl substituent is independently unsubstituted, or mono- or di-substituted, wherein the substituents are independently selected from $(C_{1-4})$alkyl, $(C_{1-4})$alkoxy, and halogen;
  and the other of said substituents, if present, is/are independently selected from $(C_{1-4})$alkyl, $(C_{1-4})$alkoxy, halogen, $(C_{1-3})$fluoroalkyl, $(C_{1-3})$fluoroalkoxy and dimethylamino.

16) A further embodiment relates to compounds of formula (I) according to any one of embodiments 1) to 14), wherein
  ring $A_1$ represents 5-membered heteroaryl, wherein the 5-membered heteroaryl is mono- or di-substituted; wherein
    one of said substituents is attached in ortho-position to the point of attachment of $A_1$ to the rest of the molecule; wherein said ortho-substituent is phenyl, or 6-membered heteroaryl (especially pyridyl); wherein said phenyl or 6-membered heteroaryl is independently unsubstituted, or mono-, or di-substituted (especially unsubstituted, or mono-substituted), wherein the substituents are independently selected from $(C_{1-4})$alkyl, $(C_{1-4})$alkoxy, halogen, $(C_{1-3})$fluoroalkyl, and $(C_{1-3})$fluoroalkoxy [wherein said ortho-substituent is especially phenyl which is unsubstituted, or mono-substituted with $(C_{1-4})$alkyl, or halogen];
    and the other of said substituents, if present, is selected from $(C_{1-4})$alkyl and dimethylamino (especially methyl);
  or ring $A_1$ represents phenyl or 6-membered heteroaryl (especially phenyl), wherein the phenyl or 6-membered heteroaryl independently is mono-, di-, or tri-substituted; wherein
    one of said substituents is attached in ortho-position to the point of attachment of $A_1$ to the rest of the molecule; wherein
      said ortho-substituent is phenyl which is unsubstituted, mono-, or di-substituted (especially unsubstituted), wherein the substituents are independently selected from $(C_{1-4})$alkyl, $(C_{1-4})$alkoxy, halogen, $(C_{1-3})$fluoroalkyl, and $(C_{1-3})$fluoroalkoxy (especially $(C_{1-4})$alkyl, and halogen);
      or said ortho-substituent is 6-membered heteroaryl (especially 6-membered heteroaryl containing one or two nitrogen atoms; in particular pyridyl or pyrimidinyl) which is unsubstituted, mono-, or di-substituted (especially unsubstituted), wherein the substituents are independently selected from $(C_{1-4})$alkyl, $(C_{1-4})$alkoxy, halogen, and $(C_{1-3})$fluoroalkyl (especially $(C_{1-4})$alkyl);
      or said ortho-substituent is 5-membered heteroaryl (in particular [1,2,3]triazol-2-yl) which is unsubstituted, or mono-substituted (especially unsubstituted), wherein the substituents are independently selected from $(C_{1-4})$alkyl, $(C_{1-4})$alkoxy, halogen, and $(C_{1-3})$fluoroalkyl;
    and the other of said substituents, if present, is/are independently selected from $(C_{1-4})$alkyl, $(C_{1-4})$alkoxy, halogen, $(C_{1-3})$fluoroalkyl, and $(C_{1-3})$fluoroalkoxy [especially $(C_{1-4})$alkyl, $(C_{1-4})$alkoxy, and halogen].

17) A further embodiment relates to compounds of formula (I) according to any one of embodiments 1) to 14), wherein ring $A_1$ represents phenyl which is mono-, di-, or tri-substituted; wherein:
  one of said substituents is attached in ortho-position to the point of attachment of $A_1$ to the rest of the molecule; wherein
    said ortho-substituent is phenyl which is unsubstituted, mono-, or di-substituted (especially unsubstituted), wherein the substituents are independently selected from $(C_{1-4})$alkyl, $(C_{1-4})$alkoxy, halogen, $(C_{1-3})$fluoroalkyl, and $(C_{1-3})$fluoroalkoxy [especially $(C_{1-4})$alkyl and halogen]; or
    said ortho-substituent is 6-membered heteroaryl (especially 6-membered heteroaryl containing one or two nitrogen atoms; in particular pyrimidinyl) which is unsubstituted, mono-, or di-substituted (especially unsubstituted), wherein the substituents are independently selected from $(C_{1-4})$alkyl, $(C_{1-4})$alkoxy, halogen, and $(C_{1-3})$fluoroalkyl [notably such 6-membered heteroaryl is unsubstituted pyrimidin-2-yl]; or
    said ortho-substituent is 5-membered heteroaryl (in particular [1,2,3]triazol-2-yl) which is unsubstituted, or mono-substituted (especially unsubstituted), wherein the substituents are independently selected from $(C_{1-4})$alkyl, $(C_{1-4})$alkoxy, halogen, and $(C_{1-3})$fluoroalkyl (especially $(C_{1-4})$alkyl, notably methyl) [notably such 5-membered heteroaryl is unsubstituted [1,2,3]triazol-2-yl];
  and the other of said substituents, if present, is/are independently selected from $(C_{1-4})$alkyl, $(C_{1-4})$alkoxy, halogen, $(C_{1-3})$fluoroalkyl, and $(C_{1-3})$fluoroalkoxy [especially $(C_{1-4})$alkyl, $(C_{1-4})$alkoxy, and halogen].

18) A further embodiment relates to compounds of formula (I) according to any one of embodiments 1) to 14), wherein
ring $A_1$ represents 5-membered heteroaryl, wherein the 5-membered heteroaryl is mono- or di-substituted; wherein
one of said substituents is attached in ortho-position to the point of attachment of $A_1$ to the rest of the molecule; wherein said ortho-substituent is phenyl which is unsubstituted, or mono-substituted, wherein the substituent is selected from methyl, fluoro, and chloro;
and the other of said substituents, if present, is selected from methyl and dimethylamino (especially methyl);
or ring $A_1$ represents phenyl which is mono-, di-, or tri-substituted; wherein
one of said substituents is attached in ortho-position to the point of attachment of $A_1$ to the rest of the molecule; wherein
said ortho-substituent is phenyl which is unsubstituted, mono-, or di-substituted (especially unsubstituted), wherein the substituents are independently selected from methyl, chloro and fluoro; or
said ortho-substituent is unsubstituted pyrimidin-2-yl; or
said ortho-substituent is unsubstituted [1,2,3]triazol-2-yl;
and the other of said substituents, if present, is/are independently selected from methyl, methoxy, chloro, fluoro, trifluromethyl, and trifluromethoxy.

19) A further embodiment relates to compounds of formula (I) according to any one of embodiments 1) to 18), wherein one or both of the following characteristics are present:
in case ring $A_1$ represents a 5-membered heteroaryl group, such group is an oxazolyl or a thiazolyl group (especially a thiazolyl group); and/or
in case ring $A_1$ represents a 6-membered heteroaryl group, such group is a pyridinyl, a pyrazinyl, or a pyrimidinyl group (especially a pyridinyl group);
wherein said groups independently are substituted as defined in any one of the preceeding embodiments.

20) A further embodiment relates to compounds of formula (I) according to any one of embodiments 1) to 17) or 19), wherein one or more of the following characteristics are present:
in case said ortho substituent of ring $A_1$ represents a 5-membered heteroaryl group, such group is unsubstituted [1,2,3]triazol-2-yl, or unsubstituted pyrazol-1-yl [especially such group is unsubstituted [1,2,3]triazol-2-yl]; and/or
in case said ortho substituent of ring $A_1$ represents a 6-membered heteroaryl group, such group is a pyridinyl or a pyrimidinyl group [especially such group is unsubstituted pyrimidin-2-yl]; and/or
in case said ortho substituent of ring $A_1$ represents a phenyl group, such group is especially an unsubstituted or mono-substituted phenyl group wherein the substituent is selected from $(C_{1-4})$alkyl, $(C_{1-4})$alkoxy, and halogen [in particular such group is phenyl, 2-methyl-phenyl, 3-methyl-phenyl, 4-methyl-phenyl, 2-fluorophenyl, 3-chlorophenyl];
wherein said groups independently are unsubstituted or substituted as defined in any one of the preceeding embodiments, or as explicitly defined herein.

21) A further embodiment relates to compounds of formula (I) according to any one of embodiments 1) to 14), wherein the ring $A_1$ represents a group selected from the following groups A and B:

A: substituted phenyl groups selected from the groups:

A.1

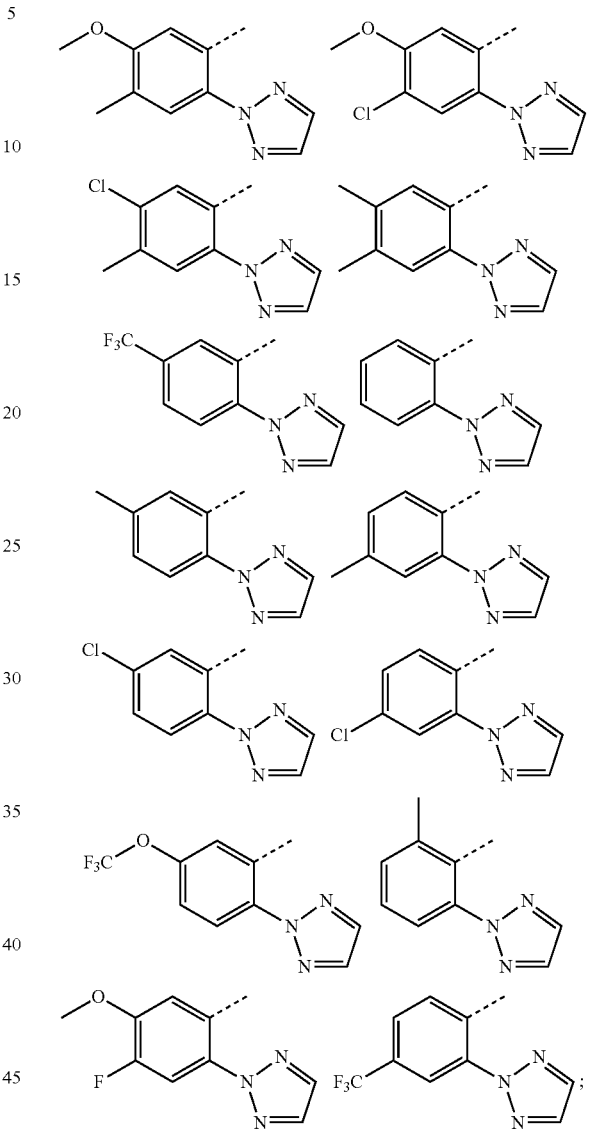

A.2

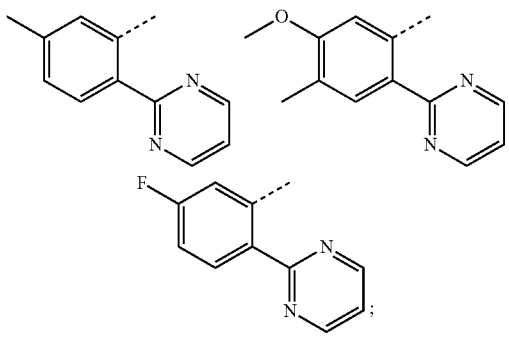

A.3

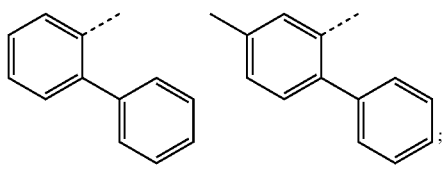

B: substituted 5-membered heteroaryl groups selected from the groups:

B.1

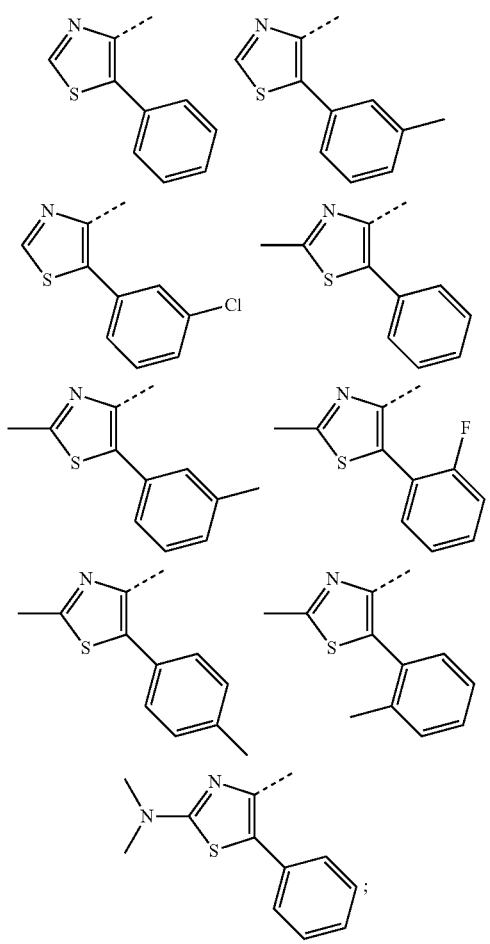

B.2

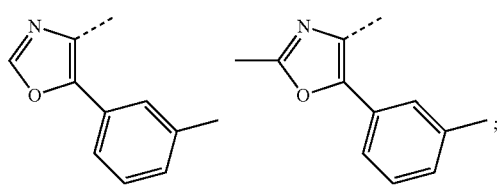

wherein groups A.1 and A.2 together form a preferred sub-embodiment.

22) A further embodiment relates to compounds of formula (I) according to any one of embodiments 1) to 14), wherein ring $A_1$ represents a group

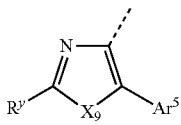

wherein $X_9$ represents O or S; and
$R^y$ represents hydrogen, $(C_{1-4})$alkyl, or dimethylamino; and
$Ar^5$ represents phenyl; wherein said phenyl is unsubstituted, mono-, di-, or tri-substituted, wherein the substituents are independently selected from $(C_{1-4})$alkyl, $(C_{1-4})$alkoxy, halogen, $(C_{1-3})$fluoroalkyl, and $(C_{1-3})$fluoroalkoxy [especially unsubstituted or mono-substituted, wherein the substituent is selected from $(C_{1-4})$alkyl and halogen; and wherein particular groups are selected from the groups listed under group B of embodiment 21)].

23) Another embodiment relates to compounds according to embodiment 22), wherein $Ar^5$ represents phenyl, wherein said phenyl is unsubstituted, mono-, or di-substituted (especially unsubstituted or mono-substituted), wherein the substituents are independently selected from $(C_{1-4})$alkyl, $(C_{1-4})$alkoxy, and halogen (especially such phenyl group is phenyl, 2-methyl-phenyl, 3-methyl-phenyl, 4-methyl-phenyl, 2-fluorophenyl, or 3-chlorophenyl); and $R^y$ represents hydrogen or $(C_{1-4})$alkyl (especially hydrogen or methyl).

24) A further embodiment relates to compounds of formula (I) according to any one of embodiments 1) to 14), wherein ring $A_1$ represents a group

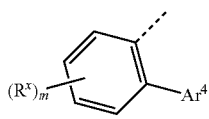

wherein
$(R^x)_m$ represents one, or two optional substituents [i.e. m represents the integer 0, 1, or 2] independently selected from the group consisting of $(C_{1-4})$alkyl, $(C_{1-4})$alkoxy, halogen, $(C_{1-3})$fluoroalkyl, and $(C_{1-3})$fluoroalkoxy; and
$Ar^4$ represents phenyl or 5- or 6-membered heteroaryl; wherein said phenyl or 5- or 6-membered heteroaryl independently is unsubstituted, mono-, di-, or tri-substituted, wherein the substituents are independently selected from the group consisting of $(C_{1-4})$alkyl, $(C_{1-4})$alkoxy, halogen, $(C_{1-3})$fluoroalkyl, and $(C_{1-3})$fluoroalkoxy.

25) Another embodiment relates to compounds according to embodiments 24), wherein
$(R^x)_m$ represents one or two substituents independently selected from $(C_{1-4})$alkyl, $(C_{1-4})$alkoxy, halogen, $(C_{1-3})$fluoroalkyl, and $(C_{1-3})$fluoroalkoxy (in particular: independently selected from methyl, methoxy, fluoro, chloro, trifluoromethyl, and trifluoromethoxy); and
$Ar^4$ represents unsubstituted or mono-substituted phenyl wherein the substituent is selected from the group consisting of $(C_{1-4})$alkyl, $(C_{1-4})$alkoxy, and halogen (especially such phenyl group is phenyl, 2-methyl-phenyl, 3-methyl-phenyl, 4-methyl-phenyl, 2-fluorophenyl, or 3-chlorophenyl); unsubstituted [1,2,3]triazol-2-yl; unsubstituted pyrazol-1-yl; unsubstituted pyridin-2-yl; or unsubstituted pyrimidin-2-yl.

26) Another embodiment relates to compounds according to embodiments 24), wherein $(R^x)_m$ represents one or two substituents independently selected from $(C_{1-4})$alkyl, $(C_{1-4})$alkoxy, halogen, $(C_{1-3})$fluoroalkyl, and $(C_{1-3})$fluoroalkoxy (in particular: independently selected from methyl, methoxy, fluoro, chloro, trifluoromethyl, and trifluoromethoxy); and $Ar^4$ represents unsubstituted pyrimidin-2-yl or unsubstituted [1,2,3]triazol-2-yl.

27) A further embodiment relates to compounds of formula (I) according to any one of embodiments 1) to 14), wherein ring $A_1$ represents a group independently selected from the following groups A, B, and C:

A.

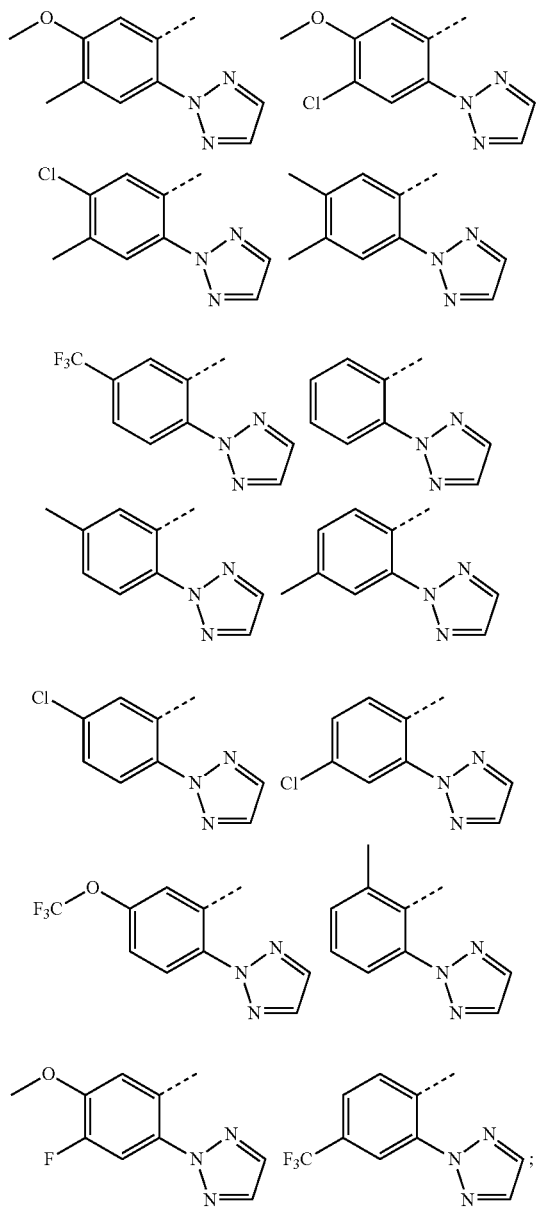

B.

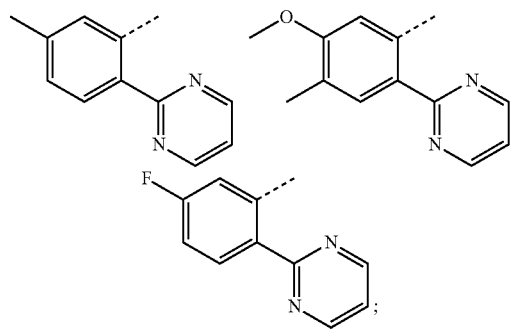

C.

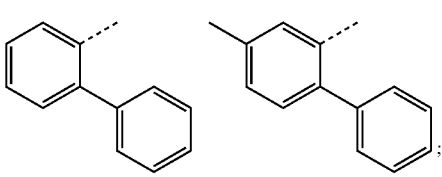

wherein each of the groups A, B and C forms a particular sub-embodiment [and said group is especially selected from groups A and B].

28) The invention, thus, relates to compounds of the formula (I) as defined in embodiment 1), or to such compounds further limited by the characteristics of any one of embodiments 2) to 27), under consideration of their respective dependencies; to pharmaceutically acceptable salts thereof; and to the use of such compounds as medicaments especially in the treatment of mental health disorders relating to orexinergic dysfunctions, which disorders are as defined below and which are especially selected from sleep disorders, anxiety disorders, addiction disorders, cognitive dysfunctions, mood disorders, or appetite disorders. Especially the following embodiments relating to the compounds of formula (I) are thus possible and intended and herewith specifically disclosed in individualized form:

1, 3+1, 4+1, 6+1, 10+1, 10+3+1, 10+4+1, 10+6+1, 11+1, 11+3+1, 11+4+1, 11+6+1, 12+1, 12+3+1, 12+4+1, 12+6+1, 13+1, 14+1, 16+1, 16+3+1, 16+4+1, 16+6+1, 16+10+1, 16+10+3+1, 16+10+4+1, 16+10+6+1, 16+11+1, 16+11+3+1, 16+11+4+1, 16+11+6+1, 16+12+1, 16+12+3+1, 16+12+4+1, 16+12+6+1, 16+13+1, 16+14+1, 17+1, 17+3+1, 17+4+1, 17+6+1, 17+10+1, 17+10+3+1, 17+10+4+1, 17+10+6+1, 17+11+1, 17+11+3+1, 17+11+4+1, 17+11+6+1, 17+12+1, 17+12+3+1, 17+12+4+1, 17+12+6+1, 17+13+1, 17+14+1, 18+1, 18+3+1, 18+4+1, 18+6+1, 18+10+1, 18+10+3+1, 18+10+4+1, 18+10+6+1, 18+11+1, 18+11+3+1, 18+11+4+1, 18+11+6+1, 18+12+1, 18+12+3+1, 18+12+4+1, 18+12+6+1, 18+13+1, 18+14+1, 19+1, 19+16+1, 19+16+3+1, 19+16+4+1, 19+16+6+1, 19+16+10+1, 19+16+10+3+1, 19+16+10+4+1, 19+16+10+6+1, 19+16+11+1, 19+16+11+3+1, 19+16+11+4+1, 19+16+11+6+1, 19+16+12+1, 19+16+12+3+1, 19+16+12+4+1, 19+16+12+6+1, 19+16+13+1, 19+16+14+1, 19+18+1, 19+18+3+1, 19+18+4+1, 19+18+6+1, 19+18+10+1, 19+18+10+3+1, 19+18+10+4+1, 19+18+10+6+1, 19+18+11+1, 19+18+11+3+1, 19+18+11+4+1, 19+18+11+6+1, 19+18+12+1, 19+18+12+3+1, 19+18+12+4+1, 19+18+12+6+1, 19+18+13+1, 19+18+14+1, 20+1,

20+19+1, 20+19+16+1, 20+19+16+3+1, 20+19+16+4+1, 20+19+16+6+1, 20+19+16+10+1, 20+19+16+10+3+1, 20+19+16+10+4+1, 20+19+16+10+6+1, 20+19+16+11+1, 20+19+16+11+3+1, 20+19+16+11+4+1, 20+19+16+11+6+1, 20+19+16+12+1, 20+19+16+12+3+1, 20+19+16+12+4+1, 20+19+16+12+6+1, 20+19+16+13+1, 20+19+16+14+1, 21+1, 21+3+1, 21+4+1, 21+6+1, 21+10+1, 21+10+3+1, 21+10+4+1, 21+10+6+1, 21+11+1, 21+11+3+1, 21+11+4+1, 21+11+6+1, 21+12+1, 21+12+3+1, 21+12+4+1, 21+12+6+1, 21+13+1, 21+14+1, 22+1, 22+3+1, 22+4+1, 22+6+1, 22+10+1, 22+10+3+1, 22+10+4+1, 22+10+6+1, 22+11+1, 22+11+3+1, 22+11+4+1, 22+11+6+1, 22+12+1, 22+12+3+1, 22+12+4+1, 22+12+6+1, 22+13+1, 22+14+1, 23+22+1, 23+22+3+1, 23+22+4+1, 23+22+6+1, 23+22+10+1, 23+22+10+3+1, 23+22+10+4+1, 23+22+10+6+1, 23+22+11+1, 23+22+11+3+1, 23+22+11+4+1, 23+22+11+6+1, 23+22+12+1, 23+22+12+3+1, 23+22+12+4+1, 23+22+12+6+1, 23+22+13+1, 23+22+14+1, 24+1, 24+3+1, 24+4+1, 24+6+1, 24+10+1, 24+10+3+1, 24+10+4+1, 24+10+6+1, 24+11+1, 24+11+3+1, 24+11+4+1, 24+11+6+1, 24+12+1, 24+12+3+1, 24+12+4+1, 24+12+6+1, 24+13+1, 24+14+1, 26+24+1, 26+24+3+1, 26+24+4+1, 26+24+6+1, 26+24+10+1, 26+24+10+3+1, 26+24+10+4+1, 26+24+10+6+1, 26+24+11+1, 26+24+11+3+1, 26+24+11+4+1, 26+24+11+6+1, 26+24+12+1, 26+24+12+3+1, 26+24+12+4+1, 26+24+12+6+1, 26+24+13+1, 26+24+14+1, 27+1, 27+3+1, 27+4+1, 27+6+1, 27+10+1, 27+10+3+1, 27+10+4+1, 27+10+6+1, 27+11+1, 27+11+3+1, 27+11+4+1, 27+11+6+1, 27+12+1, 27+12+3+1, 27+12+4+1, 27+12+6+1, 27+13+1, 27+14+1.

In the list above, the numbers refer to the embodiments according to their numbering provided hereinabove whereas "+" indicates the dependency from another embodiment. The different individualized embodiments are separated by commas. In other words, "27+14+1" for example refers to embodiment 27) depending on embodiment 14), depending on embodiment 1), i.e. embodiment "27+14+1" corresponds to the compounds of embodiment 1) further limited by the features of the embodiments 14) and 27).

29) A second aspect of the invention relates to novel compounds of the formula (I) as defined in embodiment 1), which are also compounds of the formula (II):

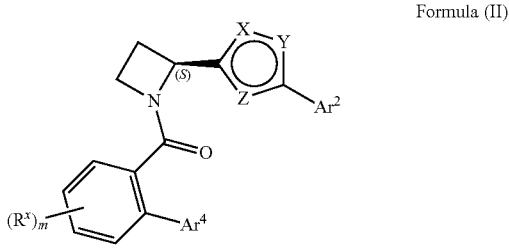

Formula (II)

wherein the carbon atom at position 2 of the azetidine ring is in absolute (S)-configuration; wherein the ring

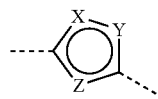

represents

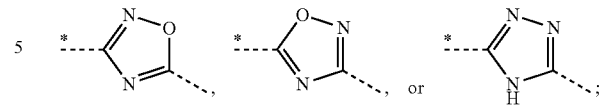

wherein the asterisks indicate the bond that is linked to the azetidin-2-yl moiety of the molecule;

Ar² represents phenyl or 6-membered heteroaryl; wherein said phenyl or 6-membered heteroaryl is independently unsubstituted, or mono-, or di-substituted; wherein the substituents are independently selected from $(C_{1-4})$alkyl, $(C_{1-4})$alkoxy, halogen, $(C_{1-3})$fluoroalkoxy, and $(C_{3-6})$cycloalkyl-oxy-;

$(R^x)_m$ represents one or two optional substituents [i.e. m represents the integer 0, 1, or 2] (especially $(R^x)_m$ represents one or two substituents) independently selected from $(C_{1-4})$alkyl, $(C_{1-4})$alkoxy, halogen, $(C_{1-3})$fluoroalkyl, and $(C_{1-3})$fluoroalkoxy (especially selected from $(C_{1-4})$alkyl, $(C_{1-4})$alkoxy, and halogen); and Ar⁴ represents phenyl, which is unsubstituted or mono-substituted (especially unsubstituted), wherein the substituent is independently selected from $(C_{1-4})$alkyl, and halogen;

or Ar⁴ represents unsubstituted pyrimidin-2-yl; or Ar⁴ represents unsubstituted [1,2,3]triazol-2-yl; wherein the characteristics disclosed in embodiments 2) to 28) above are intended to apply mutatis mutandis also to the compounds formula (II) according to embodiment 29); wherein especially the following embodiments are thus possible and intended and herewith specifically disclosed in individualized form:

29, 29+7, 29+8, 29+9, 29+11+7, 29+11+8, 29+11+9, 29+11, 29+12+7, 29+12+8, 29+12+9, 29+12, 29+13, 29+14, 29+27+7, 29+27+8, 29+27+9, 29+27+11+7, 29+27+11+8, 29+27+11+9, 29+27+11, 29+27+12+7, 29+27+12+8, 29+27+12+9, 29+27+12, 29+27+13, 29+27+14, 29+27.

In the list above the numbers refer to the embodiments according to their numbering provided hereinabove whereas "+" indicates the dependency from another embodiment as outlined above.

30) Particular compounds according to embodiment 1) are selected from:

(5-Methyl-2-[1,2,3]triazol-2-yl-phenyl)-[(S)-2-(3-o-tolyl-[1,2,4]oxadiazol-5-yl)-azetidin-1-yl]-methanone;

{(S)-2-[3-(3-Fluoro-2-methyl-phenyl)-[1,2,4]oxadiazol-5-yl]-azetidin-1-yl}-(5-methyl-2-[1,2,3]triazol-2-yl-phenyl)-methanone;

{(S)-2-[3-(2-Methoxy-phenyl)-[1,2,4]oxadiazol-5-yl]-azetidin-1-yl}-(5-methyl-2-[1,2,3]triazol-2-yl-phenyl)-methanone;

{(S)-2-[3-(3-Methoxy-phenyl)-[1,2,4]oxadiazol-5-yl]-azetidin-1-yl}-(5-methyl-2-[1,2,3]triazol-2-yl-phenyl)-methanone;

{(S)-2-[3-(3-Chloro-2-methyl-phenyl)-[1,2,4]oxadiazol-5-yl]-azetidin-1-yl}-(5-methyl-2-[1,2,3]triazol-2-yl-phenyl)-methanone;

{(S)-2-[3-(2-Ethoxy-3-fluoro-phenyl)-[1,2,4]oxadiazol-5-yl]-azetidin-1-yl}-(5-methyl-2-[1,2,3]triazol-2-yl-phenyl)-methanone;

{(S)-2-[3-(2,5-Dimethyl-phenyl)-[1,2,4]oxadiazol-5-yl]-azetidin-1-yl}-(5-methyl-2-[1,2,3]triazol-2-yl-phenyl)-methanone;

(5-Methyl-2-[1,2,3]triazol-2-yl-phenyl)-[(S)-2-(3-m-tolyl-[1,2,4]oxadiazol-5-yl)-azetidin-1-yl]-methanone;

{(S)-2-[3-(2-Chloro-phenyl)-[1,2,4]oxadiazol-5-yl]-azetidin-1-yl}-(5-methyl-2-[1,2,3]triazol-2-yl-phenyl)-methanone;

(5-Methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Fluoro-2-methoxy-phenyl)-[1,2,4]oxadiazol-5-yl]-azetidin-1-yl}-(5-methyl-2-[1,2,3]triazol-2-yl-phenyl)-methanone;

{(S)-2-[3-(3-Fluoro-2-methoxy-phenyl)-[1,2,4]oxadiazol-5-yl]-azetidin-1-yl}-(5-methoxy-4-methyl-2-[1,2,3]triazol-2-yl-phenyl)- methanone;

(4,5-Dimethyl-2-[1,2,3]triazol-2-yl-phenyl)-{(S)-2-[3-(3-fluoro-2-methoxy-phenyl)-[1,2,4]oxadiazol-5-yl]-azetidin-1-yl}-methanone;

(4,5-Dimethyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Fluoro-2-methoxy-phenyl)-[1,2,4]oxadiazol-5-yl]-azetidin-1-yl}-(4-methyl-2-[1,2,3]triazol-2-yl-phenyl)-methanone;

(4,5-Dimethyl-2-[1,2,3]triazol-2-yl-phenyl)-{(S)-2-[3-(3-fluoro-2-methyl-phenyl)-[1,2,4]oxadiazol-5-yl]-azetidin-1-yl}-methanone;

{(S)-2-[3-(3-Fluoro-2-methyl-phenyl)-[1,2,4]oxadiazol-5-yl]-azetidin-1-yl}-(4-methyl-2-[1,2,3]triazol-2-yl-phenyl)-methanone;

(4-Fluoro-5-methoxy-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(4-fluoro-5-methoxy-2-[1,2,3]triazol-2-yl-phenyl)- methanone;

(4-Fluoro-5-methoxy-2-[1,2,3]triazol-2-yl-phenyl)-{(S)-2-[3-(3-fluoro-2-methyl-phenyl)-[1,2,4]oxadiazol-5-yl]-azetidin-1-yl}-methanone;

{(S)-2-[3-(3-Fluoro-2-methoxy-phenyl)-[1,2,4]oxadiazol-5-yl]-azetidin-1-yl}-(4-fluoro-5-methoxy-2-[1,2,3]triazol-2-yl-phenyl)- methanone;

(5-Methoxy-4-methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(5-methoxy-4-methyl-2-[1,2,3]triazol-2-yl-phenyl)- methanone;

{(S)-2-[3-(3-Fluoro-2-methyl-phenyl)-[1,2,4]oxadiazol-5-yl]-azetidin-1-yl}-(5-methoxy-4-methyl-2-[1,2,3]triazol-2-yl-phenyl)- methanone;

{(S)-2-[3-(2-Ethoxy-pyridin-3-yl)-[1,2,4]oxadiazol-5-yl]-azetidin-1-yl}-(5-methyl-2-[1,2,3]triazol-2-yl-phenyl)-methanone;

(4,5-Dimethyl-2-[1,2,3]triazol-2-yl-phenyl)-{(S)-2-[3-(2-ethoxy-pyridin-3-yl)-[1,2,4]oxadiazol-5-yl]-azetidin-1-yl}-methanone;

{(S)-2-[3-(2-Ethoxy-pyridin-3-yl)-[1,2,4]oxadiazol-5-yl]-azetidin-1-yl}-(4-fluoro-5-methoxy-2-[1,2,3]triazol-2-yl-phenyl)- methanone;

{(S)-2-[3-(2-Ethoxy-pyridin-3-yl)-[1,2,4]oxadiazol-5-yl]-azetidin-1-yl}-(5-methoxy-4-methyl-2-[1,2,3]triazol-2-yl-phenyl)- methanone;

(4-Methyl-biphenyl-2-yl)-{(S)-2-[3-(2-trifluoromethoxy-phenyl)-[1,2,4]oxadiazol-5-yl]-azetidin-1-yl}-methanone;

(2-Methyl-5-phenyl-thiazol-4-yl)-{(S)-2-[3-(2-trifluoromethoxy-phenyl)-[1,2,4]oxadiazol-5-yl]-azetidin-1-yl}-methanone;

(2-Dimethylamino-5-phenyl-thiazol-4-yl)-{(S)-2-[3-(2-trifluoromethoxy-phenyl)-[1,2,4]oxadiazol-5-yl]-azetidin-1-yl}-methanone;

Biphenyl-2-yl-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(4-methyl-biphenyl-2-yl)-methanone;

{(S)-2-[3-(3-Chloro-2-methyl-phenyl)-[1,2,4]oxadiazol-5-yl]-azetidin-1-yl}-(2-dimethylamino-5-phenyl-thiazol-4-yl)-methanone;

{(S)-2-[3-(3-Chloro-2-methyl-phenyl)-[1,2,4]oxadiazol-5-yl]-azetidin-1-yl}-(4,5-dimethyl-2-[1,2,3]triazol-2-yl-phenyl)-methanone;

Biphenyl-2-yl-{(S)-2-[3-(3-chloro-2-methyl-phenyl)-[1,2,4]oxadiazol-5-yl]-azetidin-1-yl}-methanone;

(4-Chloro-5-methoxy-2-[1,2,3]triazol-2-yl-phenyl)-{(S)-2-[3-(3-chloro-2-methyl-phenyl)-[1,2,4]oxadiazol-5-yl]-azetidin-1-yl}-methanone;

(4-Chloro-5-methoxy-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(4-chloro-2-[1,2,3]triazol-2-yl-phenyl)-methanone;

(4-Chloro-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(4-methyl-2-[1,2,3]triazol-2-yl-phenyl)-methanone;

(4-Methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(5-chloro-2-[1,2,3]triazol-2-yl-phenyl)-methanone;

(5-Chloro-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(5-chloro-4-methyl-2-[1,2,3]triazol-2-yl-phenyl)- methanone;

(5-Chloro-4-methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

(5-Methyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

(4,5-Dimethyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

(5-Methoxy-4-methyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

{(S)-2-[5-(3-Fluoro-2-methoxy-phenyl)-[1,2,4]oxadiazol-3-yl]-azetidin-1-yl}-(5-methoxy-4-methyl-2-[1,2,3]triazol-2-yl-phenyl)- methanone;

(4,5-Dimethyl-2-[1,2,3]triazol-2-yl-phenyl)-{(S)-2-[5-(3-fluoro-2-methyl-phenyl)-[1,2,4]oxadiazol-3-yl]-azetidin-1-yl}-methanone;

{(S)-2-[5-(2-Ethoxy-pyridin-3-yl)-[1,2,4]oxadiazol-3-yl]-azetidin-1-yl}-(5-methyl-2-[1,2,3]triazol-2-yl-phenyl)-methanone;

(4,5-Dimethyl-2-[1,2,3]triazol-2-yl-phenyl)-{(S)-2-[5-(2-ethoxy-pyridin-3-yl)-[1,2,4]oxadiazol-3-yl]-azetidin-1-yl}-methanone;

{(S)-2-[5-(2-Ethoxy-pyridin-3-yl)-[1,2,4]oxadiazol-3-yl]-azetidin-1-yl}-(5-methoxy-4-methyl-2-[1,2,3]triazol-2-yl-phenyl)- methanone;

{(S)-2-[5-(3-Fluoro-2-methyl-phenyl)-[1,2,4]oxadiazol-3-yl]-azetidin-1-yl}-(5-methyl-2-[1,2,3]triazol-2-yl-phenyl)-methanone;

(4-Chloro-5-methoxy-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

(5-Chloro-4-methyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

(4-Chloro-5-methoxy-2-[1,2,3]triazol-2-yl-phenyl)-{(S)-2-[5-(3-fluoro-2-methyl-phenyl)-[1,2,4]oxadiazol-3-yl]-azetidin-1-yl}-methanone;

{(S)-2-[5-(2-Ethoxy-pyridin-3-yl)-[1,2,4]oxadiazol-3-yl]-azetidin-1-yl}-(4-methyl-2-[1,2,3]triazol-2-yl-phenyl)-methanone;

(4-Chloro-5-methoxy-2-[1,2,3]triazol-2-yl-phenyl)-{(S)-2-[5-(2-ethoxy-pyridin-3-yl)-[1,2,4]oxadiazol-3-yl]-azetidin-1-yl}-methanone;

(5-Chloro-4-methyl-2-[1,2,3]triazol-2-yl-phenyl)-{(S)-2-[5-(2-ethoxy-pyridin-3-yl)-[1,2,4]oxadiazol-3-yl]-azetidin-1-yl}-methanone;

{(S)-2-[5-(3-Chloro-2-methyl-phenyl)-[1,2,4]oxadiazol-3-yl]-azetidin-1-yl}-(2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(5-methyl-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(4,5-dimethyl-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(5-methoxy-4-methyl-2-[1,2,3]triazol-2-yl-phenyl)- methanone;

(4-Chloro-5-methoxy-2-[1,2,3]triazol-2-yl-phenyl)-{(S)-2-[5-(3-chloro-2-methyl-phenyl)-[1,2,4]oxadiazol-3-yl]-azetidin-1-yl}-methanone;

{(S)-2-[5-(3-Chloro-2-methyl-phenyl)-[1,2,4]oxadiazol-3-yl]-azetidin-1-yl}-(5-chloro-4-methyl-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(4-methyl-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(4-chloro-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(2-[1,2,3]triazol-2-yl-4-trifluoromethyl-phenyl)- methanone;

{(S)-2-[5-(3-Chloro-2-methoxy-phenyl)-[1,2,4]oxadiazol-3-yl]-azetidin-1-yl}-(5-methyl-2-[1,2,3]triazol-2-yl-phenyl)-methanone;

{(S)-2-[5-(3-Chloro-2-methoxy-phenyl)-[1,2,4]oxadiazol-3-yl]-azetidin-1-yl}-(4,5-dimethyl-2-[1,2,3]triazol-2-yl-phenyl)-methanone;

{(S)-2-[5-(3-Chloro-2-methoxy-phenyl)-[1,2,4]oxadiazol-3-yl]-azetidin-1-yl}-(5-methoxy-4-methyl-2-[1,2,3]triazol-2-yl-phenyl)- methanone;

{(S)-2-[5-(3-Chloro-2-methoxy-phenyl)-[1,2,4]oxadiazol-3-yl]-azetidin-1-yl}-(4-chloro-5-methoxy-2-[1,2,3]triazol-2-yl-phenyl)-methanone;

{(S)-2-[5-(3-Chloro-2-methoxy-phenyl)-[1,2,4]oxadiazol-3-yl]-azetidin-1-yl}-(5-chloro-4-methyl-2-[1,2,3]triazol-2-yl-phenyl)- methanone;

{(S)-2-[5-(3-Chloro-2-methyl-phenyl)-[1,2,4]oxadiazol-3-yl]-azetidin-1-yl}-(4-methyl-biphenyl-2-yl)-methanone;

{(S)-2-[5-(3-Chloro-2-methyl-phenyl)-[1,2,4]oxadiazol-3-yl]-azetidin-1-yl}-(5-methoxy-4-methyl-2-pyrimidin-2-yl-phenyl)-methanone;

{(S)-2-[5-(3-Chloro-2-methyl-phenyl)-[1,2,4]oxadiazol-3-yl]-azetidin-1-yl}-(5-methyl-2-pyrimidin-2-yl-phenyl)-methanone;

{(S)-2-[5-(3-Chloro-2-methoxy-phenyl)-[1,2,4]oxadiazol-3-yl]-azetidin-1-yl}-(4-methyl-2-[1,2,3]triazol-2-yl-phenyl)-methanone;

{(S)-2-[5-(3-Chloro-2-methoxy-phenyl)-[1,2,4]oxadiazol-3-yl]-azetidin-1-yl}-(4-chloro-2-[1,2,3]triazol-2-yl-phenyl)-methanone;

(4-Methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(4,5-Dimethyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(5-Methoxy-4-methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(5-Chloro-4-methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(4-Chloro-5-methoxy-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(4-Chloro-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(2-[1,2,3]Triazol-2-yl-4-trifluoromethyl-phenyl)-{(S)-2-[5-(2-trifluoromethoxy-phenyl)-4H-[1,2,4]triazol-3-yl]-azetidin-1-yl}-methanone; and (4-Methyl-biphenyl-2-yl)-{(S)-2-[5-(2-trifluoromethoxy-phenyl)-4H-[1,2,4]triazol-3-yl]-azetidin-1-yl}-methanone.

The compounds of formula (I) and (II) contain at least one stereogenic center which is situated in position 2 of the azetidine moiety. It is understood that the absolute configuration of said chiral center is as depicted in formula (I) and (II), i.e. it is in absolute (S) configuration. In addition, the compounds of formula (I) and (II) may contain one or more further stereogenic or asymmetric centers, such as one or more asymmetric carbon atoms. The compounds of formula (I) and (II) may thus be present as mixtures of stereoisomers or preferably as pure stereoisomers. Mixtures of stereoisomers may be separated in a manner known to a person skilled in the art.

In some instances, the compounds of formula (I) and (II) may contain tautomeric forms. Such tautomeric forms are encompassed in the scope of the present invention. For example, in case the present compounds contain heteroaromatic aromatic rings containing unsubstituted ring nitrogen atoms having a free valency such as imidazol-2,4-diyl, or [1,2,4]-triazol-3,5-diyl, such rings may be present in tautomeric forms. For example, the group imidazol-2,4-diyl represents the tautomeric forms 1H-imidazol-2,4-diyl and 3H-imidazol-2,4-diyl; and the group [1,2,4]triazol-3,5-diyl represents the tautomeric forms 1H-[1,2,4]triazol-3,5-diyl, 2H-[1,2,4]triazol-3,5-diyl and 4H-[1,2,4]triazol-3,5-diyl.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and (II) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) and (II) are not isotopically labelled, or they are labelled only with one or more deuterium atoms. In a sub-embodiment, the compounds of formula (I) and (II) are not isotopically labelled at all. Isotopically labelled compounds of f formula (I) and (II) may be prepared in analogy to the methods described hereinafter, but using the appropriate isotopic variation of suitable reagents or starting materials.

In this patent application, a dotted line shows the point of attachment of the radical drawn. For example, the radical drawn below

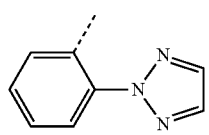

is a 2-([1,2,3]-triazol-2-yl)-phenyl group.

Where the plural form is used for compounds, salts, pharmaceutical compositions, diseases and the like, this is intended to mean also a single compound, salt, or the like.

Any reference to compounds of formula (I) and (II) as defined in any one of embodiments 1) to 30) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quere (Eds.), RSC Publishing, 2012.

Definitions provided herein are intended to apply uniformly to the compounds of formula (I) and (II) as defined in any one of embodiments 1) to 30), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, or bromine, preferably fluorine or chlorine.

The term "alkyl", used alone or in combination, refers to a saturated straight or branched chain alkyl group containing one to six carbon atoms. The term "$(C_{x-y})$alkyl" (x and y each being an integer), refers to an alkyl group as defined before, containing x to y carbon atoms. For example a $(C_{1-4})$alkyl group contains from one to four carbon atoms. Examples of alkyl groups are methyl, ethyl, propyl, isopropyl, n-butyl, isobutyl, sec.-butyl and tert.-butyl. Preferred are methyl and ethyl. Most preferred is methyl.

The term "cycloalkyl", used alone or in combination, refers to a saturated cyclic alkyl group containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl and cyclohexyl. Preferred is cyclopropyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and methoxy.

The term "fluoroalkyl" refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$ fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups such as trifluoromethyl.

The term "fluoroalkoxy" refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$fluoroalkoxy groups such as trifluoromethoxy and difluoromethoxy.

The term "aryl" refers to a naphthyl or, preferably, to a phenyl group; wherein said group is unsubstituted or substituted as explicitly defined.

Particular examples of the ring $A_1$ representing a phenyl group wherein said phenyl is mono-, di-, or tri-substituted; wherein one of said substituents is attached in ortho-position to the point of attachment of ring $A_1$ to the rest of the molecule, is such that the other of said substituents, if present, is/are independently selected from $(C_{1-4})$alkyl, $(C_{1-4})$alkoxy, and halogen (especially methyl, methoxy and halogen). Likewise, in the group

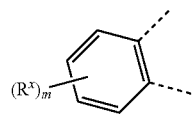

the group $(R^x)_m$ represents one or two optional substituents independently selected from $(C_{1-4})$alkyl, $(C_{1-4})$alkoxy, and halogen (especially methyl, methoxy and halogen). Particular examples of the above mentioned phenyl groups are 1,2-phenylene, 4-methyl-1,2-phenylene, 5-methyl-1,2-phenylene, 4,5-dimethyl-1,2-phenylene, 6-methyl-1,2-phenylene, 5-fluoro-1,2-phenylene, 5-chloro-1,2-phenylene, 4-chloro-1,2-phenylene, 4-methyl-5-methoxy-1,2-phenylene, 4-chloro-5-methoxy-1,2-phenylene, 4-fluoro-5-methoxy-1,2-phenylene, 5-chloro-4-methyl-1,2-phenylene, 5-trifluoromethyl-1,2-phenylene, 4-trifluoromethoxy-1,2-phenylene, and 5-trifluoromethoxy-1,2-phenylene; wherein in the above groups the carbonyl group is attached in position 1.

Particular examples of the ring $A_2$ representing phenyl groups are unsubstituted, or mono-, di-, or tri-substituted; wherein the substituents are independently selected from $(C_{1-4})$alkyl, $(C_{1-4})$alkoxy, halogen, $(C_{1-3})$fluoroalkyl, $(C_{1-3})$fluoroalkoxy; [notably from $(C_{1-4})$alkyl, $(C_{1-4})$alkoxy, halogen, $(C_{1-3})$fluoroalkyl, and $(C_{1-3})$fluoroalkoxy; especially from methyl, methoxy, halogen, trifluoromethyl, and trifluoromethoxy]. Particular examples are phenyl, 2-methyl-phenyl, 3-methyl-phenyl, 4-methyl-phenyl, 2,5-dimethyl-phenyl, 2-methoxy-phenyl, 3-methoxy-phenyl, 2-(n-propoxy)-phenyl, 3-fluoro-2-methoxy-phenyl, 3-fluoro-2-ethoxy-phenyl, 3-chloro-2-methoxy-phenyl, 3,4-difluoro-phenyl, 3,5-difluoro-phenyl, 2-chloro-phenyl, 3-fluoro-2-methyl-phenyl, 2-fluoro-6-methyl-phenyl, 3-chloro-2-methyl-phenyl, and 2-trifluoromethoxy-phenyl.

Examples of the particular phenyl groups which are ortho substituents of ring $A_1$, (in particular: groups $Ar^4$ and $Ar^5$) are unsubstituted or mono-substituted phenyl groups wherein the substituent is selected from $(C_{1-4})$alkyl, $(C_{1-4})$alkoxy, and halogen (especially methyl and halogen); such as especially phenyl, 2-methyl-phenyl, 3-methyl-phenyl, 4-methyl-phenyl, 2-fluorophenyl, and 3-chlorophenyl.

The term "heteroaryl", if not explicitly stated otherwise, refers to a 5- or 6-membered monocyclic aromatic ring containing 1 to a maximum of 3 heteroatoms independently selected from oxygen, nitrogen and sulfur. Examples of such heteroaryl groups are 5-membered monocyclic heteroaryl groups such as furanyl, oxazolyl, isoxazolyl, oxadiazolyl, thienyl, thiazolyl, isothiazolyl, thiadiazolyl, pyrrolyl, imidazolyl, pyrazolyl, and triazolyl; and 6-membered monocyclic heteroaryl such as pyridyl, pyrimidyl, pyridazinyl, and pyrazinyl.

Examples of the particular 5- or 6-membered heteroaryl groups which are further substituted in ortho position as used for the ring $A_1$ are the above mentioned 5- or 6-membered heteroaryl groups, notably oxazolyl (in particular oxazol-4,5-diyl, 2-methyl-oxazol-4,5-diyl), thiazolyl (in particular thiazol-4,5-diyl, 2-methyl-thiazol-4,5-diyl, 2-dimethylamino-thiazol-4,5-diyl), pyridyl (in particular pyridin-2,3-diyl, 6-methyl-pyridin-2,3-diyl), pyrimidyl (in particular pyrimidin-4,5-diyl, 2-methyl-pyrimidin-4,5-diyl), and pyrazinyl (in particular pyrazin-2,3-diyl). These groups are at least mono-substituted in ortho position, and preferably carry no further substituent or one further substitutent as explicitly defined. In particular such optional further substituent is $(C_{1-4})$alkyl, notably methyl, or, in case of thiazolyl groups additionally dimethylamino. The above groups are preferably attached to the rest of the molecule (i.e. the carbonyl group) in position 4 of oxazolyl, imidazolyl, or thiazolyl groups, in position 2 or 3 of pyridyl or pyrazinyl groups, or in position 5 of pyrimidinyl groups. In a sub-embodiment, examples of such groups are thiazol-4,5-diyl, 2-methyl-thiazol-4,5-diyl, 2-dimethylamino-thiazol-4,5-diyl, oxazol-4,5-diyl, and 2-methyl-oxzol-4,5-diyl.

Particular examples of the ring $A_2$ representing a 6-membered heteroaryl are especially 6-membered heteroaryl groups which are unsubstituted, or mono-substituted; wherein the substituent is selected from $(C_{1-4})$alkyl, $(C_{1-4})$alkoxy, halogen, $(C_{1-3})$fluoroalkyl, $(C_{1-3})$fluoroalkoxy, and $(C_{3-6})$cycloalkyl-oxy-[notably from $(C_{1-4})$alkoxy, $(C_{1-3})$fluoroalkoxy, and $(C_{3-6})$cycloalkyl-oxy-]. Particular examples of such heteroaryl groups are pyrazinyl, pyrimidyl and notably pyridyl groups, which groups are unsubstituted, or mono-substituted; wherein the substituent is selected from $(C_{1-4})$alkyl, $(C_{1-4})$alkoxy, $(C_{1-3})$fluoroalkoxy, and $(C_{3-6})$cycloalkyl-oxy- (especially methoxy, ethoxy, and cyclobutyloxy); such as especially 2-(cyclobutyl-oxy)-pyridin-3-yl, and 2-ethoxy-pyridin-3-yl.

Examples of the particular 5- or 6-membered heteroaryl groups which are ortho substituents of ring $A_1$ (in particular: groups $Ar^4$) are the above mentioned 5- or 6-membered heteroaryl groups, notably oxazolyl, isoxazolyl, oxadiazolyl, thienyl, thiazolyl, isothiazolyl, thiadiazolyl, imidazolyl, pyrazolyl, triazolyl, pyridyl, pyrimidyl, and pyrazinyl. The above mentioned groups are preferably unsubstituted or may be substituted as explicitly defined. Preferred examples are triazolyl (notably unsubstituted [1,2,3]triazol-2-yl), pyrazolyl (notably unsubstituted pyrazol-1-yl), oxazolyl (notably unsubstituted oxazol-2-yl), oxadiazolyl (notably 3-methyl-[1,2,4]oxadiazol-5-yl); pyridinyl (notably unsubstituted pyridin-2-yl), and pyrimidinyl (notably unsubstituted pyrimidin-2-yl) [notably unsubstituted [1,2,3]triazol-2-yl, and unsubstituted pyrimidin-2-yl].

The compounds of compounds of formula (I) and (II) as defined in any one of embodiments 1) to 30) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject in need thereof a pharmaceutically active amount of a compounds of formula (I) and (II) as defined in any one of embodiments 1) to 30).

In a preferred embodiment of the invention, the administered amount of such a compound of formula (I) or (II) as defined in any one of embodiments 1) to 30) is comprised between 1 mg and 1000 mg per day, particularly between 5 mg and 500 mg per day, more particularly between 25 mg and 400 mg per day, especially between 50 mg and 200 mg per day.

For avoidance of any doubt, if compounds are described as being useful for the prevention or treatment of certain diseases, such compounds are likewise suitable for use in the preparation of a medicament for the prevention or treatment of said diseases.

The compounds of formula (I) and (II) as defined in any one of embodiments 1) to 30) are useful for the prevention or treatment of disorders relating to orexinergic dysfunctions.

Such disorders relating to orexinergic dysfunctions are diseases or disorders where an antagonist of a human orexin receptor is required, notably mental health disorders relating to orexinergic dysfunctions. The above mentioned disorders may in particular be defined as comprising sleep disorders, anxiety disorders, addiction disorders, cognitive dysfunctions, mood disorders, and appetite disorders. In one sub-embodiment, the above mentioned disorders comprise especially sleep disorders, anxiety disorders, addiction disorders, cognitive dysfunctions, and appetite disorders. In another sub-embodiment, the above mentioned disorders comprise especially sleep disorders, anxiety disorders, and addiction disorders. In yet another sub-embodiment, the above mentioned disorders comprise especially sleep disorders.

In addition, further disorders relating to orexinergic dysfunctions are selected from treating, controlling, ameliorating or reducing the risk of epilepsy, including absence epilepsy; treating or controlling pain, including neuropathic pain; treating or controlling Parkinson's disease; treating or controlling psychosis including acute mania and bipolar disorder; treating or controlling stroke, particularly ischemic or haemorrhagic stroke; blocking an emetic response i.e. nausea and vomiting; and treating or controlling agitation, in isolation or co-morbid with another medical condition.

In another embodiment, further disorders relating to orexinergic dysfunctions are selected from schizoaffective disorders; dissociative disorders including multiple personality syndromes and psychogenic amnesias; sexual and reproductive dysfunction; psychosexual dysfunction and addiction; increased anaesthetic risk; anaesthetic responsiveness; hypothalamic-adrenal dysfunctions; all types of amnesia; severe mental retardation; dyskinesias and muscular diseases; muscle spasticity; tremors; movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; seizure disorders; complex partial and generalized seizures; Lennox-Gastaut syndrome; migraine and headache; anaesthesia and analgesia; enhanced or exaggerated sensitivity to pain such as hyperalgesia, causalgia, and allodynia; acute pain; burn pain; atypical facial pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; all types of cerebrovascular disorders including subarachnoid haemorrhage, and vascular dementia; chronic renal failure and other renal diseases; gout; kidney cancer; and urinary incontinence;

Anxiety disorders can be distinguished by the primary object or specificity of threat, ranging from rather diffuse as in generalized anxiety disorder, to circumscribed as encountered in phobic anxieties (PHOBs) or post-traumatic stress disorders (PTSDs). Anxiety disorders may, thus, be defined as comprising generalized anxiety disorders (GAD), obsessive compulsive disorders (OCDs), acute stress disorders, post-traumatic stress disorders (PTSDs), panic anxiety disorders (PADs) including panic attacks, phobic anxieties (PHOBs), specific phobia, social phobia (social anxiety disorder), avoidance, somatoform disorders including hypochondriasis, separation anxiety disorder, anxiety disorders due to a general medical condition, and substance induced anxiety disorders. In a sub-embodiment, particular examples of circumscribed threat induced anxiety disorders are phobic anxieties or post-traumatic stress disorders. Anxiety disorders especially include post-traumatic stress disorders, obsessive compulsive disorders, panic attacks, phobic anxieties, and avoidance.

Addiction disorders may be defined as addictions to one or more rewarding stimuli, notably to one rewarding stimulus. Such rewarding stimuli may be of either natural or synthetic origin. Examples of such rewarding stimuli are substances/drugs {of either natural or synthetic origin; such as cocaine, amphetamines, opiates [of natural or (semi-)synthetic origin such as morphine or heroin], *cannabis*, ethanol, mescaline, nicotine, and the like}, which substances/drugs may be consumed alone or in combination; or other rewarding stimuli {of either natural origin (such as food, sweet, fat, or sex, and the like), or synthetic origin [such as gambling, or internet/IT (such as immoderate gaming, or inappropriate involvement in online social networking sites or blogging), and the like]}. In a sub-embodiment, addiction disorders relating to psychoactive substance use, abuse, seeking and reinstatement are defined as all types of psychological or physical addictions and their related tolerance and dependence components. Substance-related addiction disorders especially include substance use disorders such as substance dependence, substance craving and substance abuse; substance-induced disorders such as substance intoxication, substance withdrawal, and substance-induced delirium. The expression "prevention or treatment of addictions" (i.e. preventive or curative treatment of patients who have been diagnosed as having an addiction, or as being at risk of developing addictions) refers to diminishing addictions, notably diminishing the onset of addictions, to weakening their maintenance, to facilitating withdrawal, to facilitating abstinence, or to attenuating, decreasing or preventing the occurrence of reinstatement of addiction (especially to diminishing the onset of addictions, to facilitating withdrawal, or to attenuating, decreasing or preventing the occurrence of reinstatement of addiction).

Mood disorders include major depressive episode, manic episode, mixed episode and hypomanic episode; depressive disorders including major depressive disorder, dysthymic disorders; bipolar disorders including bipolar I disorder, bipolar II disorder (recurrent major depressive episodes with hypomanic episodes), cyclothymic disorder; mood disorders including mood disorder due to a general medical condition (including the subtypes with depressive features, with major depressive-like episode, with manic features, and with mixed features), substance-induced mood disorder (including the subtypes with depressive features, with manic features, and with mixed features). Such mood disorders are especially major depressive episode, major depressive disorder, mood disorder due to a general medical condition; and substance-induced mood disorder.

Appetite disorders comprise eating disorders and drinking disorders. Eating disorders may be defined as comprising eating disorders associated with excessive food intake and complications associated therewith; anorexias; compulsive eating disorders; obesity (due to any cause, whether genetic or environmental); obesity-related disorders including overeating and obesity observed in Type 2 (non-insulin-dependent) diabetes patients; bulimias including bulimia nervosa; cachexia; and binge eating disorder. Particular eating disorders comprise metabolic dysfunction; dysregulated appetite control; compulsive obesities; bulimia or anorexia nervosa. In a sub-embodiment, eating disorders may be defined as especially comprising anorexia nervosa, bulimia, cachexia, binge eating disorder, or compulsive obesities. Drinking disorders include polydipsias in psychiatric disorders and all other types of excessive fluid intake. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance.

Cognitive dysfunctions include deficits in attention, learning and especially memory functions occurring transiently or chronically in psychiatric, neurologic, neurodegenerative, cardiovascular and immune disorders, and also occurring transiently or chronically in the normal, healthy, young, adult, or especially aging population. Cognitive dysfunctions especially relate to the enhancement or maintenance of memory in patients who have been diagnosed as having, or being at risk of developing, diseases or disorders in which diminished memory (notably declarative or procedural) is a symptom [in particular dementias such as frontotemporal dementia, or dementia with Lewy bodies, or (especially) Alzheimer's disease]. Especially, the term "prevention or treatment of cognitive dysfunctions" relates to the enhancement or maintenance of memory in patients who have a clinical manifestation of a cognitive dysfunction, especially expressed as a deficit of declarative memory, linked to dementias such as frontotemporal dementia, or dementia with Lewy bodies, or (especially) Alzheimer's disease. Furthermore, the term "prevention or treatment of cognitive dysfunctions" also relates to improving memory consolidation in any of the above mentioned patient populations.

Sleep disorders comprise dyssomnias, parasomnias, sleep disorders associated with a general medical condition and substance-induced sleep disorders. In particular, dyssomnias include intrinsic sleep disorders (especially insomnias, breathing-related sleep disorders, periodic limb movement disorder, and restless leg syndrome), extrinsic sleep disorders, and circadian-rhythm sleep disorders. Dyssomnias notably include insomnia, primary insomnia, idiopathic insomnia, insomnias associated with depression, emotional/mood disorders, aging, Alzheimer's disease or cognitive impairment; REM sleep interruptions; breathing-related sleep disorders; sleep apnea; periodic limb movement disorder (nocturnal myoclonus), restless leg syndrome, circadian rhythm sleep disorder; shift work sleep disorder; and jet-lag syndrome. Parasomnias include arousal disorders and sleep-wake transition disorders; notably parasomnias include nightmare disorder, sleep terror disorder, and sleepwalking disorder. Sleep disorders associated with a general medical condition are in particular sleep disorders associated with diseases such as mental disorders, neurological disorders, neuropathic pain, and heart and lung diseases. Substance-induced sleep disorders include especially the subtypes insomnia type, parasomnia type and mixed type, and notably include conditions due to drugs which cause reductions in REM sleep as a side effect. Sleep disorders especially include all types of insomnias, sleep-related dystonias; restless leg syndrome; sleep apneas; jet-lag syndrome; shift work sleep disorder, delayed or advanced sleep phase syndrome, or insomnias related to psychiatric disorders. In addition, sleep disorders further include sleep disorders associated with aging; intermittent treatment of chronic insomnia; situational transient insomnia (new environment, noise) or short-term insomnia due to stress; grief; pain or illness.

In the context of the present invention, it is to be understood that, in case certain environmental conditions such as stress or fear (wherein stress may be of social origin (e.g. social stress) or of physical origin (e.g. physical stress), including stress caused by fear) facilitate or precipitate any of the disorders or diseases as defined before, the present compounds may be particularly useful for the treatment of such environmentally conditioned disorder or disease.

Preparation of Compounds of Formula (I))

The present compounds can be prepared by well known literature methods, by the methods given below, by the methods given in the experimental part or by analogous methods. Optimum reaction conditions may vary with the particular reactants or solvents used, but such conditions can be determined by a person skilled in the art by routine optimisation procedures. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. In some cases the order of carrying out the following reaction schemes, and/or reaction steps, may be varied to facilitate the reaction or to avoid unwanted reaction products. In the general sequence of reactions outlined below, the generic groups $A_1$, $A_2$, and $A_3$ are as defined for formula (I). In some instances the generic groups $A_1$, $A_2$, and $A_3$ may be incompatible with the assembly illustrated in the schemes below and so will require the use of protecting groups (PG). The use of protecting groups is well known in the art (see for example "Protective Groups in Organic Synthesis", T. W. Greene, P.G.M. Wuts, Wiley-Interscience, 1999). For the purposes of this discussion, it will be assumed that such protecting groups as necessary are in place. The compounds obtained may also be converted into pharmaceutically acceptable salts thereof in a manner known per se. Compounds are synthesized as their S-enantiomers.

In case $A_3$ is a [1,2,4]oxadiazol-3,5-diyl-, compounds of formula (I) may in general be prepared as illustrated in Reaction Scheme A and B. Compounds of structure A-1 can be coupled with commercially available (S)-methyl azetidine-2-carboxylate using standard amide coupling conditions such as EDC/HOBt, HOAt/DCC, TBTU, HATU or PyBOP in the presence of a base such as DIPEA or TEA at rt in a suitable solvent such as DCM, DMF, MeCN or mixtures thereof (Step a, Reaction Scheme A). Saponification of the ester function of compounds of structure A-2 using methods known in the art such as treatment with base such as NaOH in a solvent or a solvent mixture such as EtOH/water or THF may afford the desired carboxylic acids of structure A-3 (Step b, Reaction Scheme A). Compounds of structure A-3 may be converted in a two step procedure to compounds of formula (I). First, coupling of a compound of structure A-3 with hydroxyamidine A-4 in the presence of coupling reagents such as EDC/

HOBT, PyBOP, HATU, TBTU in the presence of a base such as DIPEA or TEA at rt in a suitable solvent such as DCM, DMF or mixture thereof to give intermediate acyl hydroxyamidines of structure A-5 (Step c, Reaction Scheme A). Second, the cyclization of compounds of structure A-5 in solvents such as dioxane or xylene may be achieved thermally in a temperature range from 60-100° C. for hours to days to obtain compounds of formula (I) (Step d, Reaction Scheme A).

about 30 min to several days (see WO 2006/12349, Lucca et al J. Med. Chem. 1998, 2411-2423).

Reaction Scheme A

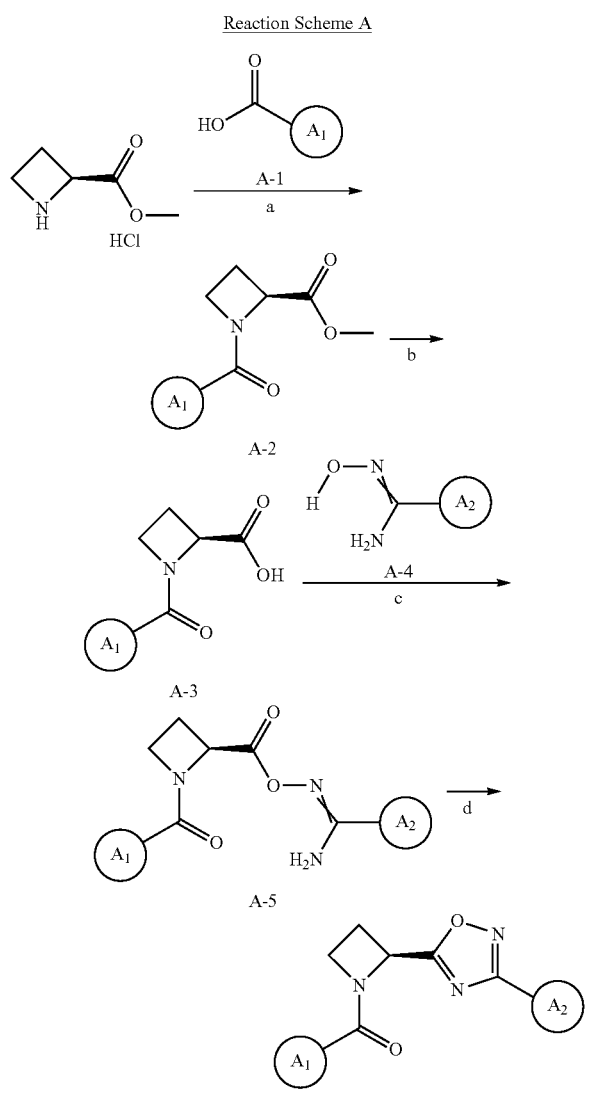

Reaction Scheme B

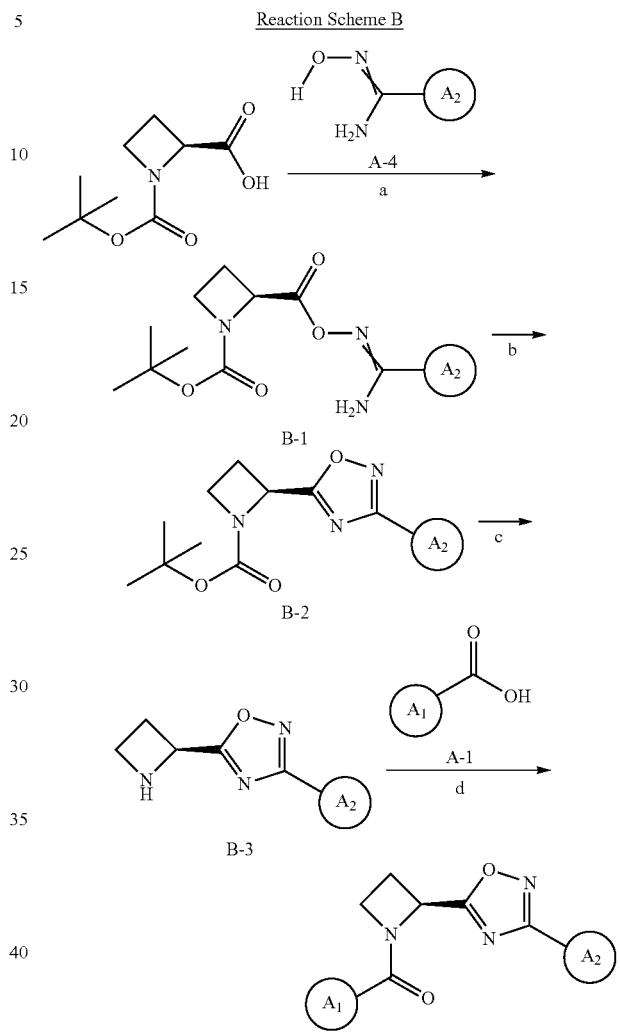

Carboxylic acids A-1 are well known in the art and can be especially prepared following the procedures reported in WO2008069997, WO2008008517, WO2010048012, WO2010063662, WO2010063663, WO2011050198, WO2011050200 and WO2011050202. In addition, they may be prepared in analogy to the methods given in the experimental part.

Commercially available nitrile-derivatives may be reacted with hydroxylamine under neutral or basic conditions such as TEA DIPEA, $Na_2CO_3$, $NaHCO_3$, NaOH, $KO^tBu$ and the like in a suitable solvent (MeOH, EtOH, etc) to obtain hydroxyamidine A-4. The reaction typically proceeds by allowing the reaction temperature to go from rt to a range of 65-80° C., for Compounds of formula (I), wherein $A_3$ is a [1,2,4]oxadiazol-3,5-diyl-, can alternatively be prepared as outlined in Reaction Scheme B. The commercially available (S)-1-(tert-butoxycarbonyl)azetidine-2-carboxylic acid may be coupled with hydroxyamidines of structure A-4 to obtain acyl-hydroxyamidines of structure B-1 (Step a, Reaction Scheme B). The coupling reaction may be promoted by coupling reagents outlined in Step c, Reaction Scheme A. Cyclization is performed as outlined in Step d, Reaction Scheme A, leading to compounds of structure B-2 (Step b, Reaction Scheme B). Boc-deprotection of compounds of structure B-2 by using standard methods such as treatment with 4N HCl in dioxane or with TFA leads to compounds of structure B-3 (Step c, Reaction Scheme B). Reaction of compounds of B-3 with acids of structure A-1 in the presence of coupling reagents, base and solvents as outlined in Step a, Reaction Scheme A furnishes compounds of formula (I) (Step d, Reaction Scheme B).

Compounds of formula (I), wherein $A_3$ is a [1,2,4]oxadiazol-3,5-diyl-, can be prepared as outlined in Reaction Scheme C.

The commercially available (S)-1-(tert-butoxycarbonyl)azetidine-2-carboxylic acid can be converted to carboxamide C-1, by activation with ethyl chloroformate, in the presence of TEA and NH₃ in water, in solvents such as THF at 0° C. to rt. Reduction to (S)-2-cyano-azetidine-1-carboxylic acid tert-butyl ester C-2 can be achieved in the presence of trifluoro-acetic anhydride and base such as TEA in solvents such as DCM at about 0° C. Nitrile C-2 may be reacted with hydroxylamine under neutral or basic conditions such as TEA, DIPEA, Na₂CO₃, NaHCO₃, NaOH, KOH, KO′Bu and the like in a suitable solvent (MeOH, EtOH, etc) to obtain hydroxyamidine C-3. The reaction typically proceeds by allowing the reaction temperature to go from rt to about 70° C. for 1 to 2 h. The acyl-hydroxyamidines of structure C-5 can be synthesized by coupling compounds of structure C-3 with compounds of structure C-4 as outlined in Step c, Reaction Scheme A. The cyclization of compounds of structure C-5 can be achieved thermally as mentioned in Step d, Reaction Scheme A or in the presence of TBAF in solvents such as THF at elevated temperature in accordance to literature procedures (WO2005113522) to yield compounds of structure C-6. Boc-deprotection using standard methods as mentioned in Step c, Scheme B lead to compounds of structure C-7. Reaction of amines C-7 with carboxylic acids of structure A-1, in the presence of coupling reagents, base and solvents as outlined in Step a, Reaction Scheme A furnishes compounds of formula (I).

Reaction Scheme C

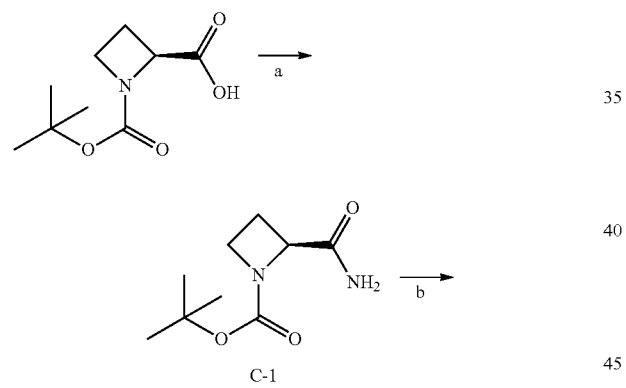

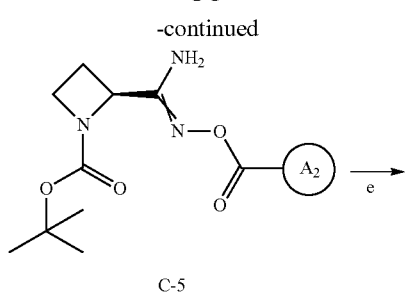

C-5

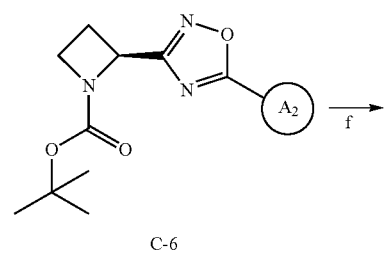

C-6

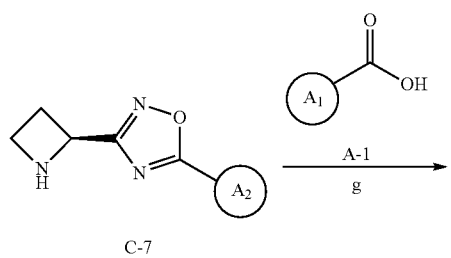

C-7

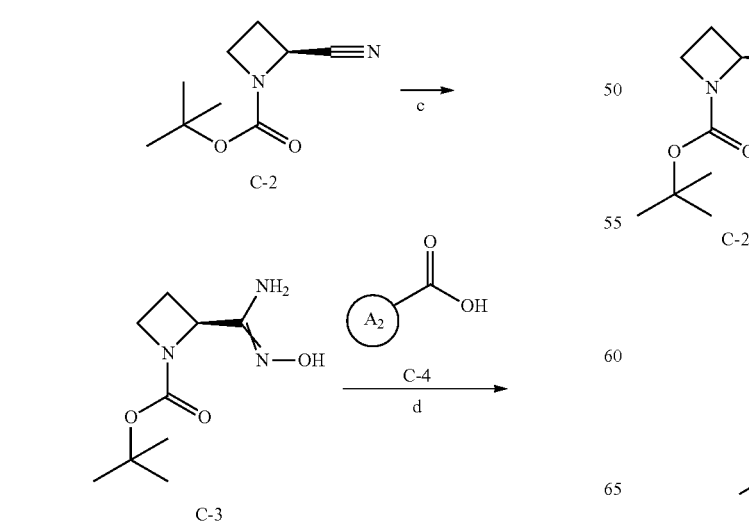

Reaction Scheme D

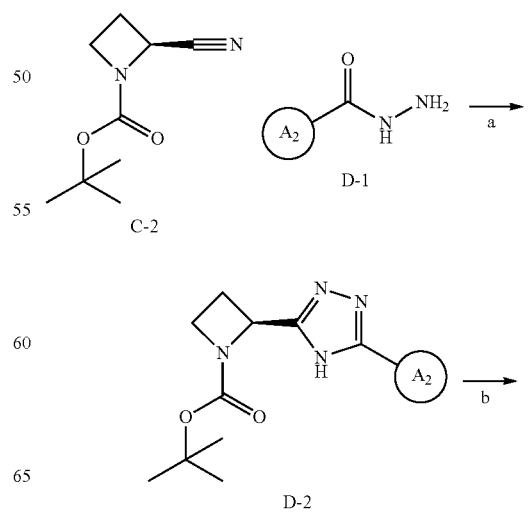

D-2

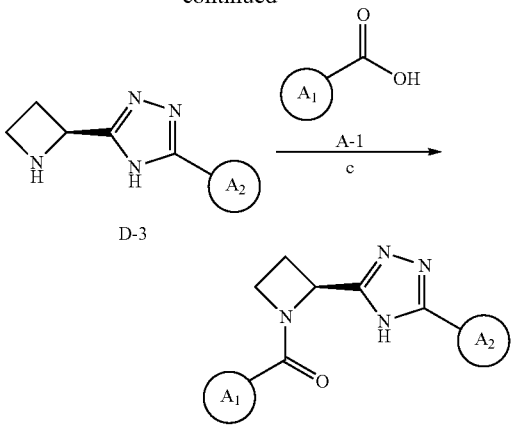

In case $A_3$ is a [1,2,4]triazol-3,5-diyl-, compounds of formula (I) may in general be prepared as illustrated in Reaction Scheme D.

Compound of structure D-2 can be synthesized from nitrile of structure C-2 and hydrazides of structure D-1 in presence of a base such as $K_2CO_3$ in a solvent such as n-butanol at elevated temperature of about 125° C. or under microwave irradiation at a temperature of about 150° C. Boc-deprotection using standard methods such as mentioned in Step c, Scheme B leads to compounds of structure D-3. Amide coupling of amines of structure D-3 with acids of structure A-1, in the presence of coupling reagents, base and solvents as outlined in Step a, Reaction Scheme A furnishes compounds of formula (I).

Hydrazides of structure D-1 are either commercially available or synthesized from commercially available carboxcylic acids or esters according to procedures known by persons skilled in the art (see experimental part).

Whenever the compounds of formula (I) or (II) are obtained in the form of mixtures of stereoisomers such as especially enantiomers, the stereoisomers can be separated using methods known to one skilled in the art: e.g. by formation and separation of diastereomeric salts or by HPLC over a chiral stationary phase such as a Daicel ChiralPak AD-H (5 μm) column, a Daicel ChiralCel OD-H (5 μm) column, a Daicel ChiralCel OD (10 μm) column, a Daicel ChiralPak IA (5 μm) column, a Daicel ChiralPak IB (5 μm) column, a Daicel ChiralPak IC (5 μm) column, or a (R,R)-Whelk-01 (5 μm) column. Typical conditions of chiral HPLC are an isocratic mixture of eluent A (EtOH, in presence or absence of a base like TEA and/or diethylamine or of an acid like TFA) and eluent B (heptane).

EXPERIMENTAL PART

I. Chemistry

All temperatures are stated in ° C. Commercially available starting materials were used as received without further purification. Unless otherwise specified, all reactions were carried out under an atmosphere of nitrogen or argon. Compounds were purified by flash column chromatography (FC) on silica gel or by preparative HPLC. Compounds described in the invention are characterized by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given.

LC-MS with Acidic Conditions
Method A:
Agilent 1100 series with mass spectrometry detection (MS: Finnigan single quadrupole). Column: Zorbax SB-aq (3.5 μm, 4.6×50 mm). Conditions: MeCN [eluent A]; water+0.04% TFA [eluent B]. Gradient: 95% B→5% B over 1.5 min (flow: 4.5 mL/min). Detection: UV/Vis+MS.

Method B:
Agilent 1100 series with mass spectrometry detection (MS: Finnigan single quadrupole). Column: Waters XBridge C18 (2.5 μm, 4.6×30 mm). Conditions: MeCN [eluent A]; water+0.04% TFA [eluent B]. Gradient: 95% B→5% B over 1.5 min (flow: 4.5 mL/min). Detection: UV/Vis+MS.

Preparative HPLC with Acidic Conditions
Method C:
Column: Waters XBridge (10 μm, 75×30 mm). Conditions: MeCN [eluent A]; water+0.5% HCOOH [eluent B]; Gradient: 90% B→5% B over 6.4 min (flow: 75 mL/min). Detection: UV/Vis+MS.

Method D:
Column: Waters Atlantis (10 μm, 75×30 mm). Conditions: MeCN [eluent A]; water+0.5% HCOOH [eluent B]; Gradient: 90% B→5% B over 6.4 min (flow: 75 mL/min). Detection: UV/Vis+MS.

Preparative HPLC with Basic Conditions
Method E:
Column: Waters XBridge (10 μm, 75×30 mm). Conditions: MeCN [eluent A]; water+0.5% $NH_4OH$ (25% aq.) [eluent B]; Gradient: 90% B→5% B over 6.5 min (flow: 75 mL/min). Detection: UV/Vis+MS

ABBREVIATIONS

As Used Hereinbefore or Hereinafter

AcOH acetic acid
aq. aqueous
BSA bovine serum albumin
Boc butyloxycarbonyl
d days
DCC dicyclohexyl carbodiimide
DCM dichloromethane
DIPEA diisopropyl-ethylamine, Hunig's base, ethyl-diisopropylamine
DMAP 4-dimethylaminopyridne
DMCDA trans-N,N'-dimethylcyclohexane-1,2-diamine
DME 1,2-dimethoxyethane
DMF dimethylformamide
DMSO dimethylsulfoxide
EDC N-(3-dimethylaminopropyl)-N'-ethyl-carbodiimide
eq. equivalent(s)
Et ethyl
EtOAc ethyl acetate
Ex. example(s)
FC flash chromatography
GM General Method
h hour(s)
hex hexane
hept heptane
HOBt 1-hydroxybenzotriazole
HPLC high performance liquid chromatography
KO$^t$Bu potassium tert-butoxide
LC-MS liquid chromatography—mass spectrometry
Me methyl MeCN acetonitrile
MeOH methanol
min minute(s)
OAc acetate
org. organic
Pd(PPh$_3$)$_4$ tetrakis(triphenylphosphine)palladium
Ph phenyl
PPh$_3$ triphenyl phosphine
prep. preparative
PyBOP benzotriazol-1-yl-oxy-tris-pyrrolidino-phosphonium-hexafluoro-phosphate
rt room temperature
rxn reaction
sat. saturated
SM starting material
TBTU 2-(1H-benzotriazole-1-yl)-1,2,3,3-tetramethyluronium tetrafluoroborate
TEA triethylamine
TFA trifluoroacetic acid
THF tetrahydrofuran
TLC thin layer chromatography
t$_R$ retention time Synthesis of Intermediate A-1

Compounds of structure A-1 were prepared in analogy to the procedure described in WO2008/069997. The addition of DMCDA is optional, but may alter the yield.

4-Chloro-2-(2H-1,2,3-triazol-2-yl)benzoic acid (A-1-1)

Cs$_2$CO$_3$ (12.0 g, 37 mmol) was added portionwise to a rt solution of commercially available 4-chloro-2-iodobenzoic acid (5.22 g, 18.5 mmol) in DMF (25 mL) followed by 1H-1,2,3-triazole (1.61 mL, 27.8 mmol) and Cu(I)I (210 mg, 1.1 mmol). The resulting blue suspension was stirred at 120° C. for 30 min, then the rxn mixture was quenched with 2M aq. HCl and filtered through a celite plug before being extracted with DCM (3×). The combined org. layers were dried (Na$_2$SO$_4$), filtered and evaporated in vacuo to give the crude product that was purified by FC (Biotage SP1: eluting with DCM/MeOH 95:5+0.1% AcOH) to give the title compound A-1-1 as a brown solid. LC-MS A: t$_R$=0.66 min; [M($^{35}$Cl)+H]$^+$=224.10.

Listed in Table 1 below are o-triazolocarboxylic acids of structure A-1, unless otherwise stated, prepared from the corresponding commercially available iodo-carboxylic acid according to the above procedure (see A-1-1), using 1H-1,2,3-triazole.

TABLE 1

| A-1 | Name | t$_R$ [min]; LC-MS Method | MS-data m/z [M + H]$^+$ |
| --- | --- | --- | --- |
| A-1-2 | 5-Methyl-2-(2H-1,2,3-triazol-2-yl)benzoic acid | 0.53; B | 204.13 |
| A-1-3 | 4-Methyl-2-(2H-1,2,3-triazol-2-yl)benzoic acid | 0.53; B | 204.23 |
| A-1-4 | 2-(2H-1,2,3-Triazol-2-yl)benzoic acid | 0.55; A | 190.08 |
| A-1-5 | 5-Chloro-2-(2H-1,2,3-triazol-2-yl)benzoic acid | 0.66; A | ($^{35}$Cl) 224.3 |
| A-1-6 | 4,5-Dimethyl-2-(2H-1,2,3-triazol-2-yl)benzoic acid | 0.59; B | 218.09 |
| A-1-7[#‡] | 4-Chloro-5-methoxy-2-(2H-1,2,3-triazol-2-yl)benzoic acid | 0.70; A | ($^{35}$Cl) 254.01 |
| A-1-8[#‡] | 4-Fluoro-5-methoxy-2-(2H-1,2,3-triazol-2-yl)benzoic acid | 0.64; A | 238.1 |
| A-1-9 | 2-(2H-1,2,3-triazol-2-yl)-5-(trifluoromethoxy)benzoic acid | 0.66; B | 273.71 |
| A-1-10[#] | 2-(2H-1,2,3-triazol-2-yl)-4-(trifluoromethyl)benzoic acid | 0.72; A | No ionization |
| A-1-11[#‡] | 5-Methoxy-4-methyl-2-(2H-1,2,3-triazol-2-yl)benzoic acid | 0.68; A | 234.05 |
| A-1-12 | 2-(2H-1,2,3-triazol-2-yl)-5-(trifluoromethyl)benzoic acid | 0.64; B | No ionization |
| A-1-13 | 2-Methyl-6-(2H-1,2,3-triazol-2-yl)benzoic acid | 0.51; B | 204.22 |

[#]Prepared from the corresponding o-bromo-carboxylic acid
[‡]Corresponding o-bromo-carboxylic acid was synthesized according to below mentioned procedures.

The synthesis of 2-bromo-substituted benzoic acids were performed in analogy to described methods (Tetrahedron Letters, 2009, 1267-1269, J. Org. Chem, 2007, 9786-9).

2-Bromo-5-methoxy-4-methyl-benzoic acid

Br$_2$ (0.74 mL, 14.4 mmol) was added to a rt suspension of 3-methoxy-4-methylbenzoic acid (2.00 g, 12 mmol) in acetic acid (15 mL) and water (15 mL), then the mixture was heated to 60° C. for 2 h. The mixture was allowed to reach rt and the solids were filtered off and rinsed with cold water (40 mL) to yield 2-bromo-5-methoxy-4-methylbenzoic acid as a white solid which was used further without purification. LC-MS A: t$_R$=0.76 min, [M+H]$^+$=no ionization. $^1$H NMR (DMSO) δ$_H$: 7.49 (s, 1H), 7.29 (s, 1H), 3.82 (s, 3H), 2.17 (s, 3H).

2-Bromo-4-fluoro-5-methoxy-benzoic acid

The title compound was prepared from 4-fluoro-3-methoxybenzoic acid in analogy to the above described method. LC-MS A: t$_R$=0.72 min, [M+H]$^+$=no ionization. $^1$H NMR (DMSO) δ$_H$: 13.52 (bs, 1H), 7.77 (dd, 1H), 7.44 (dd, 1H), 4.01 (s, 3H).

2-Bromo-4-chloro-5-methoxybenzoic acid

The title compound was prepared from 4-chloro-3-methoxybenzoic acid in analogy to the above described method. LC-MS A: t$_R$=0.77 min, [M+H]$^+$=no ionization. $^1$H NMR (DMSO) δ$_H$: 13.60 (bs, 1H), 7.82 (s, 1H), 7.47 (s, 1H), 3.91 (s, 3H).

4-Methyl-[1,1'-biphenyl]-2-carboxylic acid (A-1-14)

Step A:
H$_2$SO$_4$ 95-98% (2.54 mL, 0.048 mol) was added to a solution of 2-iodo-5-methylbenzoic acid (25.0 g, 0.095 mol) in MeOH (220 mL) and refluxed for 20 h. The rxn mixture was cooled with an ice bath, and 1N aq. NaOH was added dropwise until pH 8 was reached. The org. solvent was removed in vacuo and the aq. layer was extracted with DCM (2×). The combined org. extracts were washed with sat. aq. NaHCO$_3$ (1×) and H$_2$O (1×), dried (Na$_2$SO$_4$), filtered and concentrated in vacuo to give methyl 2-iodo-5-methylbenzoate as a pale yellow liquid which was used in the next step without further purification. LC-MS A: t$_R$=0.87 min; [M+H]$^+$=259.22.

Step B:
Pd(PPh$_3$)$_4$ (523 mg, 0.45 mmol) was added to a rt solution of methyl 2-iodo-5-methylbenzoate in toluene (23 mL). After the solution was stirred for 10 min, a solution of phenylboronic acid (1.24 g, 9.96 mmol) in EtOH (10 mL) was added, followed by 2M aq. Na$_2$CO$_3$ (21 mL). The mixture was vigorously stirred and heated to reflux for 24 h. The rxn mixture was allowed to reach rt, then Et$_2$O was added and the org. layer was separated and concentrated in vacuo. Purification by FC (Biotage SP1: EtOAc/hept eluting with a gradient of 0-10% EtOAc) was performed to give methyl 4-methyl-[1,1'-biphenyl]-2-carboxylate as a colorless oil. LC-MS A: $t_R$=0.94 min; [M+H]$^+$=227.16.

Step C:

32% aq. NaOH (74 mL) was added to a rt solution of methyl 4-methyl-[1,1'-biphenyl]-3-carboxylate (15.5 g, 0.068 mol) in MeOH (124 mL). The rxn mixture was stirred at 65° C. for 2 h, then the org. solvent was evaporated, water added, and the aq. layer acidified with conc. HCl. The mixture was stirred at rt for 30 min, and the precipitate was filtered off to give the title compound A-1-14 as a white solid. LC-MS A: $t_R$=0.80 min; [M+H]$^+$=no ionization.

5-Chloro-4-methyl-2-(2H-1,2,3-triazol-2-yl)benzoic acid (A-1-15)

Cs$_2$CO$_3$ (742 mg, 2.28 mmol) was added portionwise to a rt solution of 2-bromo-5-chloro-4-methyl-benzoic acid methyl ester (300 mg, 1.14 mmol) in DMF (3 mL) followed by 1H-1,2,3-triazole (0.1 mL, 1.71 mmol), Cu(I)I (13 mg, 0.068 mmol) and DMCDA (40 uL, 0.23 mmol). The resulting suspension was stirred at 120° C. for 4 h. The rxn mixture was quenched with 2M aq. HCl and extracted with EtOAc (3×). The combined org. layers were dried (Na$_2$SO$_4$), filtered and evaporated in vacuo to obtain the crude product that was purified by prep. HPLC (method C) to give the title compound A-1-15 as a pale yellow solid. LC-MS A: $t_R$=0.72 min; [M($^{35}$Cl)+H]+=238.01.

5-Methoxy-4-methyl-2-(pyrimidin-2-yl)benzoic acid (A-1-16)

Step A was performed in analogy to a described method (J. Org. Chem, 2007, 9786-9).

Step A:

Br$_2$ (1.11 mL, 21.7 mmol) was added to a rt suspension of 3-methoxy-4-methylbenzoic acid (3.00 g, 18.1 mmol) in a mixture of acetic acid (23 mL) and water (23 mL) and the mixture was heated to 60° C. for 2 h. The mixture was allowed to reach rt and the solids were filtered and rinsed with water to yield 2-bromo-5-methoxy-4-methylbenzoic acid as a white solid which was used as such in the next step. LC-MS A: $t_R$=0.76 min, no ionization.

Step B:

H$_2$SO$_4$ (0.5 mL, 9.3 mmol) was added to a suspension of 2-bromo-5-methoxy-4-methylbenzoic acid (4.07 g, 16.6 mmol) in MeOH (40 mL) and the resulting rxn mixture was heated to 70° C. overnight. The rxn mixture was cooled to 0° C. and basified with 1M aq. NaOH (10 mL) to pH 11. The rxn mixture was extracted with DCM and the combined org. layers were dried (MgSO$_4$), filtered and concentrated in vacuo to yield methyl 2-bromo-5-methoxy-4-methylbenzoate as a yellow solid that was used as such in the next step without purification. LC-MS A: $t_R$=0.90 min, [M+H]$^+$=258.91.

Step C:

Pd(PPh$_3$)$_4$ (416 mg, 0.36 mmol) was added to a rt solution of 2-tributylstannylpyrimidine (1.40 g, 3.6 mmol) and methyl 2-bromo-5-methoxy-4-methylbenzoate (1.03 g, 3.96 mmol) in degassed DME (7 mL) and the resulting mixture was irradiated in the microwave at 160° C. for 1 h. To the rxn mixture was added Pd(PPh$_3$)$_4$ (315 mg, 0.27 mmol) and irradiation was continued at 160° C. for another 2 h. The rxn mixture was diluted with EtOAc and H$_2$O, filtered over celite, the org. layer was separated and the aq. layer was re-extracted with EtOAc. The combined org. extracts were dried (MgSO$_4$), filtered, concentrated in vacuo and purified by FC (Biotage SP1: EtOAc/hex 1:9 to 3:7) to yield methyl 5-methoxy-4-methyl-2-(pyrimidin-2-yl)benzoate as a brown solid which was used without further purification. LC-MS A: $t_R$=0.75 min, [M+H]$^+$=258.99.

Step D:

1M aq. NaOH (4 mL) was added to a rt suspension of methyl 5-methoxy-4-methyl-2-(pyrimidin-2-yl)benzoate (503 mg, 1.95 mmol) in MeOH (5 mL) and THF (5 mL) and stirred at rt for 2 days. The residue was acidified with 25% aq. HCl, washed with DCM and concentrated in vacuo to yield the title compound A-1-16 as a off-white solid as its HCl-salt. LC-MS A: $t_R$=0.63 min, [M+H]$^+$=245.06.

Carboxylic acids from Table 2 are either commercially available or fully described in the literature.

TABLE 2

| A-1 | Name of Carboxylic Acid | Literature Procedure or Commercial Availability |
|---|---|---|
| A-1-17 | 5-(3-Chlorophenyl)thiazole-4-carboxylic acid | WO2009/016560 |
| A-1-18 | 5-(2-Fluorophenyl)-2-methylthiazole-4-carboxylic acid | WO2008/038251 |
| A-1-19 | [1,1'-Biphenyl]-2-carboxylic acid | commercially available |
| A-1-20 | 2-Methyl-5-(m-tolyl)oxazole-4-carboxylic acid | WO2010/004507 WO2009/077990 |
| A-1-21 | 2-Methyl-5-(m-tolyl)thiazole-4-carboxylic acid | WO2008/081399 WO2008/065626 |
| A-1-22 | 5-Methyl-2-(pyrimidin-2-yl)benzoic acid | commercially available |
| A-1-23 | 3-(2-Chlorophenyl)-5-methylisoxazole-4-carboxylic acid | commercially available |
| A-1-24 | 2-Methyl-5-phenyl-thiazole-4-carboxylic acid | commercially available |
| A-1-25 | 5-Phenyl-1,3-thiazole-4-carboxylic acid | commercially available |
| A-1-26 | 5-(m-Tolyl)thiazole-4-carboxylic acid | WO 2010/044054 |
| A-1-27 | 2-(Dimethylamino)-5-phenylthiazole-4-carboxylic acid | WO2010/004507 |
| A-1-28 | 2-Methyl-5-(p-tolyl)thiazole-4-carboxylic acid | WO2010/004507 |
| A-1-29 | 2-Methyl-5-(o-tolyl)thiazole-4-carboxylic acid | WO2009/016560 |
| A-1-30 | 5-Fluoro-2-(pyrimidin-2-yl)benzoic acid | WO2011/050200 |
| A-1-31 | 5-(m-Tolyl)oxazole-4-carboxylic acid | WO2009/077990 WO2010/143116 |

Synthesis of Intermediate A-2

(S)-1-(5-Methyl-2-[1,2,3]triazol-2-yl-benzoyl)-azetidine-2-carboxylic acid methyl ester (A-2-1)

TBTU (4.93 g, 15.4 mmol) was added to a rt solution of 5-methyl-2-(2H-1,2,3-triazol-2-yl)benzoic acid A-1-2 (2.40 mg, 11.8 mmol) and DIPEA (8.09 mL, 47.2 mmol) in DCM (24 mL) and after stirring for 15 min, (S)-methyl azetidine-2-carboxylate HCl (2.03 g, 13 mmol) was added and the resulting mixture was stirred at rt for 1 h. The rxn mixture was diluted with DCM and water, the layers were separated and the aq. layer was extracted with DCM (1×). The combined org. extracts were washed with brine, dried (MgSO$_4$), filtered and concentrated in vacuo. The crude was purified by FC (EtOAc/hept 5:1) to obtain the title compound A-2-1 as a white solid. LC-MS A: $t_R$=0.70 min; [M+H]$^+$=301.18.

Listed in Table 3 below are esters of type A-2, prepared from commercially available (S)-methyl azetidine-2-carboxylate HCl and acids of structure A-1, synthesized according to described methods.

TABLE 3

| A-2 | SM A-1 | Name | tR [min] LC/MS-Method | MS-data m/z [M + H]+ |
|---|---|---|---|---|
| A-2-2 | A-1-6 | (S)-1-(4,5-Dimethyl-2-[1,2,3]triazol-2-yl-benzoyl)-azetidine-2-carboxylic acid methyl ester | 0.73 A | 315.16 |
| A-2-3 | A-1-3 | (S)-1-(4-Methyl-2-[1,2,3]triazol-2-yl-benzoyl)-azetidine-2-carboxylic acid methyl ester | 0.69 A | 301.14 |
| A-2-4 | A-1-11 | (S)-1-(5-Methoxy-4-methyl-2-[1,2,3]triazol-2-yl-benzoyl)-azetidine-2-carboxylic acid methyl ester | 0.74 A | 331.09 |
| A-2-5 | A-1-8 | (S)-1-(4-Fluoro-5-methoxy-2-[1,2,3]triazol-2-yl-benzoyl)-azetidine-2-carboxylic acid methyl ester | 0.72 A | 335.14 |

Synthesis of Intermediate A-3

(S)-1-(5-Methyl-2-[1,2,3]triazol-2-yl-benzoyl)-azetidine-2-carboxylic acid (A-3-1)

2N aq. NaOH (10.5 mL) was added to a rt solution of A-2-1 (3.32 g, 11 mmol) in MeOH (17 mL) and THF (17 mL). The mixture was stirred at rt for 2 h, then the org. solvents were removed in vacuo and the residue was acidified with 6N aq. HCl. The aq. layer was extracted with DCM (2×), the combined org. layers washed with brine, dried (MgSO$_4$), filtered and concentrated in vacuo to give the title compound A-3-1 as a white solid that was used further without purification. LC-MS A: $t_R$=0.61 min; [M+H]$^+$=287.17.

Listed in Table 4 below are compounds of structure A-3, prepared according to the above procedure (see A-3-1).

TABLE 4

| A-3 | SM A-2 | Name | tR [min] LC/MS-Method | MS-data m/z [M + H]+ |
|---|---|---|---|---|
| A-3-2 | A-2-2 | (S)-1-(4,5-Dimethyl-2-[1,2,3]triazol-2-yl-benzoyl)-azetidine-2-carboxylic acid | 0.65 A | 301.15 |
| A-3-3 | A-2-3 | (S)-1-(4-Methyl-2-[1,2,3]triazol-2-yl-benzoyl)-azetidine-2-carboxylic acid | 0.61 A | 287.16 |

TABLE 4-continued

| A-3 | SM A-2 | Name | tR [min] LC/MS-Method | MS-data m/z [M + H]+ |
|---|---|---|---|---|
| A-3-4 | A-2-4 | (S)-1-(5-Methoxy-4-methyl-2-[1,2,3]triazol-2-yl-benzoyl)-azetidine-2-carboxylic acid | 0.66 A | 317.08 |
| A-3-5 | A-2-5 | (S)-1-(4-Fluoro-5-methoxy-2-[1,2,3]triazol-2-yl-benzoyl)-azetidine-2-carboxylic acid | 0.63 A | 321.13 |

Synthesis of Intermediate A-4

General Method A for the Synthesis of Hydroxyamidines (A-4)

To a solution of nitrile-derivative (1.0 eq.) in MeOH (0.5 M), hydroxylamine HCl (1.1 to 3.0 eq.) and NaHCO$_3$ (1.1 to 3.0 eq.) was added at rt. The resulting suspension was stirred at a given temperature and time (see Table 5). The mixture was concentrated in vacuo, then EtOAc was added to the remaining residue and the org. layer was washed with brine (1×), dried (MgSO$_4$), filtered and concentrated to yield hydroxyamidine A-4.

General Method B for the Synthesis of Hydroxyamidines (A-4)

Hydroxylamine HCl (1.0 eq.) was added to a rt solution of nitrile-derivative (1 eq.) and 1M aq. NaOH (1 eq.) in EtOH (1 M). The resulting suspension was stirred at a given temperature and time (see Table 5). The org. solvent was concentrated in vacuo and the remaining residue was extracted with DCM (3×). The combined org. layers were dried (MgSO$_4$), filtered and concentrated to yield hydroxyamidine A-4.

General Method C for the Synthesis of Hydroxyamidines (A-4)

To a solution of hydroxylamine HCl (1.1 to 3 eq.) and NaHCO$_3$ (1.1 to 3 eq.) in water (2M), nitrile-derivative and EtOH (2M) was added at rt and stirred at a given temperature and time (see Table 5). The org. solvent was concentrated in vacuo and the remaining residue was extracted with DCM (3×). The combined org. layers were dried (MgSO$_4$), filtered and concentrated to yield hydroxyamidine A-4.

Listed in Table 5 below are hydroxylamidines of type A-4, prepared from either commercially available nitrile-derivates or synthesized according to described methods.

TABLE 5

| A-4 | Hydroxyamidine | SM | GM | T [° C.] time [h] | tR [min] LC/MS-Method | MS-data m/z [M + H]+ |
|---|---|---|---|---|---|---|
| A-4-1 | N-Hydroxy-3-methyl-benzamidine | | B | 80 5.5 | 0.39 A | 151.08 |
| A-4-2 | N-Hydroxy-3-methoxy-benzamidine | | A | 65 18 | 0.37 A | 167.14 |

TABLE 5-continued

| A-4 | Hydroxyamidine | SM | GM | T [° C.] time [h] | $t_R$ [min] LC/MS-Method | MS-data m/z [M + H]$^+$ |
|---|---|---|---|---|---|---|
| A-4-3 | N-Hydroxy-2-methyl-benzamidine | | A | 85 48 | 0.3 A | 151.23 |
| A-4-4 | N-Hydroxy-4-methyl-benzamidine | | A | 75 18 | 0.39 A | 151.21 |
| A-4-5 | N-Hydroxy-2,5-dimethyl-benzamidine | | A | 85 96 | 0.43 A | 165.07 |
| A-4-6 | N-Hydroxy-2-methoxy-benzamidine | | A | 80 48 | 0.36 A | 167.05 |
| A-4-7 | N-Hydroxy-2-trifluoromethoxy-benzamidine | | A | 85 6 | 0.39 A | 221.03 |
| A-4-8 | 3,4-Difluoro-N-hydroxy-benzamidine | | C | rt 18 | 0.27 B | 172.08 |
| A-4-9 | 3,5-Difluoro-N-hydroxy-benzamidine | | A | 60 18 | 0.26 B | 172.95 |
| A-4-10 | 2-Chloro-N-hydroxy-benzamidine | | C | 80 24 | 0.21 B | ($^{35}$Cl) 170.97 |
| A-4-11 | 3-Chloro-N-hydroxy-2-methyl-benzamidine | | A | 80 24 | 0.35 B | ($^{35}$Cl) 185.22 |
| A-4-12 | 3-Fluoro-N-hydroxy-2-methyl-benzamidine | | C | 80 24 | 0.27 B | 169.04 |

TABLE 5-continued

| A-4 | Hydroxyamidine | SM | GM | T [°C.] time [h] | $t_R$ [min] LC/MS-Method | MS-data m/z [M + H]⁺ |
|---|---|---|---|---|---|---|
| A-4-13 | 3-Fluoro-N-hydroxy-2-methoxy-benzamidine | | A | 70 / 18 | 0.26 B | 185.26 |
| A-4-14 | 2-Ethoxy-N-hydroxy-nicotinamidine | a) | A | 70 / 6 | 0.27 B | 182.18 |
| A-4-15 | N-Hydroxy-2-propoxy-benzamidine | | A | 80 / 18 | 0.48 A | 195.17 |
| A-4-16 | 2-Cyclobutoxy-N-hydroxy-nicotinamidine | a) | A | 70 / 6 | 0.39 B | 208.13 |
| A-4-17 | 2-Ethoxy-3-fluoro-N-hydroxy-benzamidine | a) | A | 70 / 18 | 0.36 B | 199.16 |
| A-4-18 | 2-Fluoro-N-hydroxy-6-methyl-benzamidine | | A | 70 / 18 | 0.21 B | 168.96 | a) Nitriles, which are not commercially available, are synthesized according to procedures described below.

Synthesis of Nitriles

3-Ethoxyisonicotinonitrile

Sodium ethoxide (53 mg, 0.74 mmol) was added to a 0° C. solution of 3-chloro-4-cyanopyridine (100 mg, 0.72 mmol) in DMF (1 mL). The mixture was stirred at 0° C. for 30 min and at rt for 2 h, then the mixture was concentrated in vacuo. To the residue Et₂O was added, and the salts were filtered off. The filtrate was concentrated in vacuo to yield the title compound as a white solid. LC-MS A: $t_R$=0.67 min; [M($^{35}$Cl)+H]⁺=149.06.

2-Cyclobutoxynicotinonitrile

NaH 60% dispersion in mineral oil (100 mg, 2.5 mmol) was added to a rt solution of cyclobutanol (0.13 mL, 1.6 mmol) in DMF (1.5 mL). After stirring for 1 h, 3-cyano-2-fluoropyridine (150 mg, 1.23 mmol) was added and the brown suspension was stirred at rt for 1 h. The rxn mixture was quenched with water and extracted with DCM (2×). The combined org. layers were dried (MgSO₄), filtered and concentrated in vacuo to yield 2-cyclobutoxynicotinonitrile as an orange oil. LC-MS B: $t_R$=0.76 min; [M+H]⁺=175.21. ¹H NMR (DMSO) $\delta_H$: 8.43 (m, 1H), 8.26 (dd, J₁=7.6 Hz, J₂=1.9 Hz, 1H), 7.17 (dd, J₁=7.6 Hz, J₂=5.0 Hz, 1H), 5.25 (m, 1H), 2.43 (m, 2H), 2.13 (m, 2H), 1.82 (m, 1H), 1.66 (m, 1H).

2-Ethoxy-3-fluorobenzonitrile

NaH 60% dispersion in mineral oil (575 mg, 14.4 mmol) was added to a rt solution of EtOH (1.0 mL, 17.1 mmol) in DMF (6.0 mL). After stirring for 40 min at rt, the solution was cooled to 0° C., 2,3-difluorobenzonitrile (1.59 mL, 14.4 mmol) was added dropwise and stirring was continued for 1 h at rt. The rxn mixture was quenched with water and extracted with DCM (2×). The combined org. layers were dried (MgSO₄), filtered and concentrated in vacuo to yield 2-ethoxy-3-fluorobenzonitrile as an orange oil. LC-MS B: $t_R$=0.74 min; [M+H]⁺+=no ionization. ¹H NMR (CDCl₃) $\delta_H$: 7.66 (m, 2H), 7.27 (m, 1H), 4.32 (q, 2H), 1.35 (t, 3H).

Synthesis of Intermediate B-2

(S)-2-(3-Phenyl-[1,2,4]oxadiazol-5-yl)-azetidine-1-carboxylic acid tert-butyl ester (B-2-1)

Step A:

PyBOP (2.53 g, 4.85 mmol) was added to a 0° C. solution of Boc-L-azetidine-2-carboxylic acid (650 mg, 3.23 mmol) and DIPEA (1.66 mL, 9.69 mmol) in DCM (14 mL) and the rxn mixture was stirred at rt for 20 min, before N'-hydroxybenzimidamide (440 mg, 3.23 mmol) was added and stirring continued at rt for 2 h. To the rxn mixture was added $H_2O$ and the mixture extracted with DCM (2×). The combined org. extracts were washed with brine, dried ($MgSO_4$), filtered and concentrated in vacuo to yield (S)-tert-butyl 2-((benzimidamidooxy)carbonyl)azetidine-1-carboxylate B-1-1 which was used further without purification.

Step B:

The crude B-1-1 was taken up in dioxane (20 mL) and refluxed (90° C.) for 4 h. The rxn mixture was concentrated and purified by FC (EtOAc/hept 1:4) to give the title compound B-2-1 as a yellow oil. LC-MS A: $t_R$=0.91 min; $[M+H]^+$=302.09.

Listed in Table 6 below are compounds of structure B-2, prepared from the commercially available Boc-L-azetidine-2-carboxylic acid and the corresponding hydroxyamidine A-4 according to the above procedure (see B-2-1).

TABLE 7

| B-2 | SM A-4 | Name | $t_R$ [min] LC/MS-Method | MS-data m/z $[M + H]^+$ |
|---|---|---|---|---|
| B-2-2 | A-4-7 | (S)-2-[3-(2-Trifluoromethoxy-phenyl)-[1,2,4]oxadiazol-5-yl]-azetidine-1-carboxylic acid tert-butyl ester | 0.98 A | 385.78 |
| B-2-3 | A-4-11 | (S)-2-[3-(3-Chloro-2-methyl-phenyl)-[1,2,4]oxadiazol-5-yl]-azetidine-1-carboxylic acid tert-butyl ester | 0.99 A | ($^{35}$Cl) 350.07 |

Synthesis of Intermediate B-3

5-(S)-Azetidin-2-yl-3-phenyl-[1,2,4]oxadiazole (B-3-1)

4N HCl in dioxane (5 mL, 20 mmol) was added to a 0° C. solution of B-2-1 (759 mg, 2.52 mmol) in DCM (10 mL). The resulting mixture was allowed to warm to rt and stirred at rt for 2 h, then poured into an ice-cooled solution of 2M aq. NaOH (20 mL) and extracted with DCM (3×). The combined org. extracts were washed with brine, dried ($MgSO_4$), filtered and concentrated in vacuo to obtain the title compound B-3-1 as a yellow oil that was used further without purification. LC-MS A: $t_R$=0.51 min; $[M+H]^+$=202.15.

Listed in Table 7 below are compounds of structure B-3, prepared according to the above procedure (see B-3-1).

TABLE 7

| B-3 | B-2 | Name | $t_R$ [min] LC/MS-Method | MS-data m/z $[M + H]^+$ |
|---|---|---|---|---|
| B-3-2 | B-2-2 | 5-(S)-Azetidin-2-yl-3-(2-trifluoromethoxy-phenyl)-[1,2,4]oxadiazole | 0.62 A | 327.16 $[M + H + MeCN]^+$ |

TABLE 7-continued

| B-3 | B-2 | Name | $t_R$ [min] LC/MS-Method | MS-data m/z $[M + H]^+$ |
|---|---|---|---|---|
| B-3-3 | B-2-3 | 5-(S)-Azetidin-2-yl-3-(3-chloro-2-methyl-phenyl)-[1,2,4]oxadiazole | 0.62 A | ($^{35}$Cl) 291.15 |

Synthesis of Intermediate C-1

(S)-2-Carbamoyl-azetidine-1-carboxylic acid tert-butyl ester (C-1)

TEA (10.4 mL, 74.5 mmol) was added to a 0° C. solution of Boc-L-azetidine-2-carboxylic acid (7.50 g, 37.3 mmol) in THF (85 mL) and the resulting mixture was stirred at 0° C. for 20 min, before ethyl chloroformate (3.82 mL, 39.1 mmol) was added (exotherm). The rxn mixture was stirred at 0° C. for 20 min, then 25% aq. $NH_3$ (62.7 mL, 447 mmol) in THF (25 mL) was added and the resulting mixture was allowed to reach rt and stirring was continued at rt for 45 min. The mixture was concentrated in vacuo to remove the solvent, the residue was taken up in DCM and water, the org. layer was separated and the inorg. layer was extracted with DCM (2×). The combined org. layers were dried ($MgSO_4$), filtered and concentrated in vacuo to yield the title compound C-1 as a white solid which was used further without purification. LC-MS A: $t_R$=0.52 min; $[M+H]^+$=201.27.

Synthesis of Intermediate C-2

(S)-2-Cyano-azetidine-1-carboxylic acid tert-butyl ester C-2

Trifluoroacetic anhydride (6.9 mL, 48.1 mmol) was added to a 0° C. solution of C-1 (5.34 g, 26.7 mmol) and TEA (11.1 mL, 80 mmol) in DCM (74 mL) and stirring was continued at 0° C. for 15 min. The mixture was diluted with DCM, washed with water, dried (MgSO4), filtered and concentrated in vacuo. The crude was purified by FC (Biotage SP1: EtOAc/hept 1:1) to give the title compound C-2 as a yellow oil. LC-MS A: $t_R$=0.73 min; $[M+H]^+$=183.26.

Synthesis of Intermediate C-3

(S)-2-(N-Hydroxycarbamimidoyl)-azetidine-1-carboxylic acid tert-butyl ester (C-3)

Hydroxylamine HCl (1.07 g, 15 mmol) was added to a rt solution of C-2 (1.83 g, 10 mmol) and $NaHCO_3$ (1.26 g, 15 mmol) in MeOH (30 mL) and the resulting suspension was stirred at 70° C. for 1.5 h. The mixture was concentrated in vacuo and the residue was suspended in EtOAc and water. The org. layer was separated and the inorg. layer was extracted with EtOAc (1×). The combined org. extracts were dried ($MgSO_4$), filtered and concentrated in vacuo to yield the title compound C-3 as a white solid which was used further without purification. LC-MS A: $t_R$=0.43 min; [M+H]⁺=216.12.

Synthesis of Intermediate C-6

(S)-2-[5-(3-Chloro-2-methyl-phenyl)-[1,2,4]oxadiazol-3-yl]-azetidine-1-carboxylic acid tert-butyl ester (C-6-1)

Step A:

TBTU (3.43 g, 10.7 mmol) was added to a rt solution of 3-chloro-2-methylbenzoic acid (1.40 g, 8.21 mmol) and DIPEA (3.51 mL, 20.5 mmol) in DCM (12 mL) and the rxn mixture was stirred for 15 min at rt, before C-3 (3.46 g, 10.11 mmol) was added and stirring was continued for 30 min. The mixture was diluted with DCM and water. The org. layer was separated and the inorg. layer was extracted with DCM (1×). The combined org. layers were washed with brine, dried (MgSO₄), filtered and concentrated in vacuo to give (S)-tert-butyl 2-(N'-((3-chloro-2-methylbenzoyl)oxy)carbamimidoyl)azetidine-1-carboxylate C-5-1 which was used further without purification.

Step B:

TBAF (1M in THF; 15 mL, 15 mmol) was added to a rt solution of crude C-5-1 in THF (30 mL) and the resulting solution was stirred at 70° C. for 24 h, then the solvent was partially removed and TBAF (1 eq.) was added and stirring at 70° C. was continued for 16 h. The mixture was concentrated in vacuo and the crude was purified by FC (EtOAc/hept 1:4 to 1:1) to give the title compound C-6-1 as a yellow oil. LC-MS A: $t_R$=0.99 min; [M($^{35}$Cl)+H]=350.02.

Listed in Table 8 below are compounds of structure C-6, prepared according to the above procedure (see C-6-1).

TABLE 8

| C-6 | SM C-4 | Name | $t_R$ [min] LC/MS-Method | MS-data m/z [M + H]⁺ |
|---|---|---|---|---|
| C-6-2 | | (S)-2-[5-(3-Fluoro-2-methoxy-phenyl)-[1,2,4]oxadiazol-3-yl]-azetidine-1-carboxylic acid tert-butyl ester | 0.82 A | 368.14 |
| C-6-3 | | (S)-2-[5-(3-Fluoro-2-methyl-phenyl)-[1,2,4]oxadiazol-3-yl]-azetidine-1-carboxylic acid tert-butyl ester | 0.96 A | 334.09 |
| C-6-4 | | (S)-2-[5-(2-Trifluoromethoxy-phenyl)-[1,2,4]oxadiazol-3-yl]-azetidine-1-carboxylic acid tert-butyl ester | 0.97 A | 385.93 |
| C-6-5 | | (S)-2-[5-(3-Chloro-2-methoxy-phenyl)-[1,2,4]oxadiazol-3-yl]-azetidine-1-carboxylic acid tert-butyl ester | 0.95 A | ($^{35}$Cl) 366.03 |
| C-6-6 | | (S)-2-[5-(2-Ethoxy-pyridin-3-yl)-[1,2,4]oxadiazol-3-yl]-azetidine-1-carboxylic acid tert-butyl ester | 0.91 A | 347.16 |

Synthesis of Intermediate C-7

3-(S)-Azetidin-2-yl-5-(3-chloro-2-methyl-phenyl)-[1,2,4]oxadiazole (C-7-1)

4N HCl in dioxane (20 mL, 20 mmol) was added to a 0° C. solution of C-6-1 (1.90 g, 5.48 mmol) in DCM (20 mL) and the resulting mixture was allowed to reach rt and stirred at rt for 2 h. The rxn mixture was concentrated in vacuo and triturated with Et$_2$O to give the title compound C-7-1 as a white solid which was used further without purification. LC-MS A: $t_R$=0.61 min; [M($^{35}$Cl)+H]$^+$=250.18.

Listed in Table 9 below are compounds of structure C-7, prepared according to the above procedure (see C-7-1).

Synthesis of Intermediate D-1

3-Chloro-2-methyl-benzoic acid hydrazide (D-1-2)

TBTU (678 mg, 2.11 mmol) was added to a rt solution of 3-chloro-2-methylbenzoic acid (300 mg, 1.76 mmol) and DIPEA (0.9 mL, 5.28 mmol) in DMF (5.0 mL) and the resulting solution was stirred at rt for 15 min. The mixture was cooled to 0° C. and 1M hydrazine in THF (10.6 mL, 10.6 mmol) was added and the yellow solution was stirred at rt overnight. The rxn mixture was diluted with DCM and washed with sat. aq. NaHCO$_3$. The aq. layer was re-extracted with DCM (1×) and the combined org. layers were concentrated in vacuo to give the title compound D-1-2 as a light orange solid that was used further without purification. LC-MS A: $t_R$=0.50 min; [M($^{35}$Cl)+H]$^+$=185.24.

Listed in Table 10 below are compounds of structure D-1, prepared from the commercially available carboxylic acid according to the above procedure (see D-1-2).

Table 10

| D-1 | SM | Name | $t_R$ [min] LC/MS-Method | MS-data m/z [M + H]$^+$ |
|---|---|---|---|---|
| D-1-3 | (structure: 2-(trifluoromethoxy)benzoic acid) | 2-(Trifluoromethoxy)benzohydrazide | 0.50 A | 221.16 |
| D-1-4 | (structure: 3-chloro-2-methoxybenzoic acid) | 3-Chloro-2-methoxybenzohydrazide | 0.50 A | ($^{35}$Cl) 201.09 |
| D-1-5 | (structure: 2-ethoxynicotinic acid) | 2-Ethoxynicotinohydrazide | 0.45 A | 182.18 |

TABLE 9

| C-7 | SM C-6 | Name | $t_R$ [min] LC/MS-Method | MS-data m/z [M + H]$^+$ |
|---|---|---|---|---|
| C-7-2 | C-6-2 | 3-(S)-Azetidin-2-yl-5-(3-fluoro-2-methoxy-phenyl)-[1,2,4]oxadiazole | 0.54 A | 250.11 |
| C-7-3 | C-6-3 | 3-(S)-Azetidin-2-yl-5-(3-fluoro-2-methyl-phenyl)-[1,2,4]oxadiazole | 0.57 A | 234.14 |
| C-7-4 | C-6-4 | 3-(S)-Azetidin-2-yl-5-(2-trifluoromethoxy-phenyl)-[1,2,4]oxadiazole | 0.61 A | 286.06 |
| C-7-5 | C-6-5 | 3-(S)-Azetidin-2-yl-5-(3-chloro-2-methoxy-phenyl)-[1,2,4]oxadiazole | 0.58 A | ($^{35}$Cl) 266.07 |
| C-7-6 | C-6-6 | 3-((S)-3-Azetidin-2-yl-[1,2,4]oxadiazol-5-yl)-2-ethoxy-pyridine | 0.52 A | 247.24 |

Synthesis of Intermediate D-2

(S)-2-(5-Phenyl-4H-[1,2,4]triazol-3-yl)-azetidine-1-carboxylic acid tert-butyl ester (D-2-1)

K$_2$CO$_3$ (173 mg, 1.25 mmol) was added to a rt solution of C-2 (547 mg, 3 mmol) and commercially available benzo hydrazide D-1-1 (340 mg, 2.5 mmol) in n-BuOH (4.5 mL) and the mixture was refluxed (oil bath at 130° C.) for 1 h. The mixture was concentrated in vacuo, then DCM and 1N HCl was added until acidic. The org. layer was separated, the aq. layer was extracted with DCM (3×) and the combined org. layers were dried (MgSO$_4$), filtered and concentrated in vacuo. The crude was purified by FC (EtOAc/hept 3:7 to 1:1) to give the title compound D-2-1 as a yellow oil. LC-MS A: $t_R$=0.73 min; [M+H]$^+$=301.18.

Listed in Table 11 below are compounds of structure D-2 prepared according to the above procedure (see D-2-1).

TABLE 11

| D-2 | SM D-1 | Name | $t_R$ [min] LC/MS- Method | MS-data m/z $[M + H]^+$ |
|---|---|---|---|---|
| D-2-2 | D-1-2 | (S)-2-[5-(3-Chloro-2-methyl-phenyl)-4H-[1,2,4]triazol-3-yl]-azetidine-1-carboxylic acid tert-butyl ester | 0.82 A | ($^{35}$Cl) 349.13 |
| D-2-3 | D-1-3 | (S)-2-[5-(2-Trifluoromethoxy-phenyl)-4H-[1,2,4]triazol-3-yl]-azetidine-1-carboxylic acid tert-butyl ester | 0.82 A | 385.02 |
| D-2-4 | D-1-4 | (S)-2-[5-(3-Chloro-2-methoxy-phenyl)-4H-[1,2,4]triazol-3-yl]-azetidine-1-carboxylic acid tert-butyl ester | 0.82 A | ($^{35}$Cl) 349.13 |
| D-2-5 | D-1-5 | (S)-2-[5-(2-Ethoxy-pyridin-3-yl)-4H-[1,2,4]triazol-3-yl]-azetidine-1-carboxylic acid tert-butyl ester | 0.77 A | 346.18 |

Synthesis of Intermediate D-3

3-(S)-Azetidin-2-yl-5-phenyl-4H-[1,2,4]triazole (D-3-1)

4 N HCl in dioxane (3 mL, 12 mmol) was added dropwise to a 0° C. solution of D-2-1 (439 mg, 1.46 mmol) in DCM (6 mL). The resulting mixture was allowed to warm to rt and stirred at rt for 2 h. The rxn mixture was concentrated in vacuo and triturated with Et$_2$O to obtain the title compound D-3-1 as a white solid that was used as such without further purification. LC-MS A: $t_R$=0.44 min; $[M+H]^+$=201.17.

Listed in Table 12 below are compounds of structure D-3, prepared according to the above procedure (see D-3-1).

TABLE 12

| D-3 | SM D-2 | Name | $t_R$ [min] LC/MS- Method | MS-data m/z $[M + H]^+$ |
|---|---|---|---|---|
| D-3-2 | D-2-2 | 3-(S)-Azetidin-2-yl-5-(3-chloro-2-methyl-phenyl)-4H-[1,2,4]triazole | 0.53 A | ($^{35}$Cl) 249.05 |
| D-3-3 | D-2-3 | 3-(S)-Azetidin-2-yl-5-(2-trifluoromethoxy-phenyl)-4H-[1,2,4]triazole | 0.53 A | 285.08 |
| D-3-4 | D-2-4 | 3-(S)-Azetidin-2-yl-5-(3-chloro-2-methoxy-phenyl)-4H-[1,2,4]triazole | 0.53 A | ($^{35}$Cl) 265.07 |
| D-3-5 | D-2-5 | 3-((S)-5-Azetidin-2-yl-4H-[1,2,4]triazol-3-yl)-2-ethoxy-pyridine | 0.49 A | 246.09 |

EXAMPLE COMPOUNDS

General Method D for Amide Formation PyBOP/DIPEA DCM (Step A) Followed by Thermal Cyclization (Step B)

Example 1

(5-Methyl-2-[1,2,3]triazol-2-yl-phenyl)-[(S)-2-(3-o-tolyl-[1,2,4]oxadiazol-5-yl)-azetidin-1-yl]-methanone Step A:

PyBOP (75 mg, 0.14 mmol) was added to a rt solution of A-3-1 (34 mg, 0.12 mmol) and DIPEA (0.17 mL, 1.0 mmol) in DCM (0.5 mL) and after stirring for 10 min, A-4-3 (59 mg, 0.40 mmol) was added and the resulting mixture was stirred at rt for 1-18 h. The mixture was quenched with water and extracted with DCM (2×). The combined org. extracts were washed with brine, dried (MgSO$_4$), filtered and concentrated in vacuo to give the crude (S)-2-methyl-N-((1-(5-methyl-2-(2H-1,2,3-triazol-2-yl)benzoyl)azetidine-2-carbonyl)oxy)benzimidamide A-5-1 that was used further without purification.

Step B:

The crude A-5-1 was dissolved in dioxane (0.5 mL) and heated to reflux (85° C.) for 18 h to 4 days. The solvent was removed in vacuo and the residue was purified by prep. HPLC (method E) to give the title compound as a beige solid. LC-MS A: $t_R$=0.91 min; $[M+H]^+$=401.14.

General Method E for Amide Formation TBTU/DIPEA DCM (Step A) Followed by Thermal Cyclization (Step B)

Example 2

{(S)-2-[3-(3-Fluoro-2-methyl-phenyl)-[1,2,4]oxadiazol-5-yl]-azetidin-1-yl}-(5-methyl-2-[1,2,3]triazol-2-yl-phenyl)-methanone Step A:

TBTU (437 mg, 1.36 mmol) was added to a rt solution of A-3-1 (300 mg, 1.05 mmol) and DIPEA (0.45 mL, 2.62 mmol) in DCM (4 mL) and the resulting mixture was stirred at rt for 15 min before A-4-12 (303 mg, 1.15 mmol) was added and stirring continued for 1 h at rt. The mixture was quenched with water and extracted with DCM (2×). The combined org. extracts were washed with brine, dried (MgSO$_4$), filtered and the solvent was evaporated in vacuo to give the crude product (S)-3-fluoro-2-methyl-N-((1-(5-methyl-2-(2H-1,2,3-triazol-2-yl)benzoyl)azetidine-2-carbonyl)oxy)benzimidamide A-5-2 that was used further without purification.

Step B:

The crude A-5-2 was dissolved in dioxane (3.5 mL) and the mixture was stirred at 90° C. for 18 h to 4. The solvent was removed in vacuo and the residue was purified by prep. HPLC (method D) to give the title compound as a colorless oil. LC-MS A: $t_R$=0.92 min; $[M+H]^+$=418.92.

Listed in Table 13 below are example compounds, prepared according to the above mentioned General Method D or E, from the corresponding hydroxyamidine A-4 and carboxylic acid A-3, prepared as described above (see Example 1 or Example 2).

TABLE 13

| Ex No. | SM A-3 | SM A-4 | GM | Compound of Formula (I) |
|---|---|---|---|---|
| 3 | A-3-1 | A-4-4 | D | (5-Methyl-2-[1,2,3]triazol-2-yl-phenyl)-[(S)-2-(3-p-tolyl-[1,2,4]oxadiazol-5-yl)-azetidin-1-yl]-methanone; LC-MS A: $t_R$ = 0.92 min; $[M + H]^+$ = 401.02 |
| 4 | A-3-1 | A-4-6 | D | {(S)-2-[3-(2-Methoxy-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.84 min; $[M + H]^+$ = 416.98 |
| 5 | A-3-1 | A-4-2 | D | {(S)-2-[3-(3-Methoxy-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.89 min; $[M + H]^+$ = 417.01 |

TABLE 13-continued

| Ex No. | SM A-3 | SM A-4 | GM | Compound of Formula (I) |
|---|---|---|---|---|
| 6 | A-3-1 | A-4-15 | D | (5-Methyl-2-[1,2,3]triazol-2-yl-phenyl)-{(S)-2-[3-(2-propoxy-phenyl)-[1,2,4]oxadiazol-5-yl]-azetidin-1-yl}-methanone; LC-MS A: $t_R$ = 0.94 min; [M + H]$^+$ = 445.1 |
| 7 | A-3-1 | A-4-11 | D | {(S)-2-[3-(3-Chloro-2-methyl-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.96 min; [M($^{35}$Cl) + H]$^+$ = 435.0 |
| 8 | A-3-1 | A-4-18 | D | {(S)-2-[3-(2-Fluoro-6-methyl-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.9 min; [M + H]$^+$ = 419.01 |
| 9 | A-3-1 | A-4-17 | D | {(S)-2-[3-(2-Ethoxy-3-fluoro-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.93 min; [M + H]$^+$ = 449.0 |
| 10 | A-3-1 | A-4-5 | D | {(S)-2-[3-(2,5-Dimethyl-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.95 min; [M + H]$^+$ = 415.05 |
| 11 | A-3-1 | A-4-9 | D | {(S)-2-[3-(3,5-Difluoro-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.93 min; [M + H]$^+$ = 423.01 |
| 12 | A-3-1 | A-4-8 | D | {(S)-2-[3-(3,4-Difluoro-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.9 min; [M + H]$^+$ = 423.0 |
| 13 | A-3-1 | A-4-1 | D | (5-Methyl-2-[1,2,3]triazol-2-yl-phenyl)-[(S)-2-(3-m-tolyl-[1,2,4]oxadiazol-5-yl)-azetidin-1-yl]-methanone; LC-MS A: $t_R$ = 0.92 min; [M + H]$^+$ = 401.01 |
| 14 | A-3-1 | A-4-10 | E | {(S)-2-[3-(2-Chloro-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.89 min; [M($^{35}$Cl) + H]$^+$ = 420.90 |
| 15 | A-3-1 | A-4-7 | E | (5-Methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R$ = 0.94 min; [M + H]$^+$ = 470.96 |
| 16 | A-3-1 | A-4-13 | E | {(S)-2-[3-(3-Fluoro-2-methoxy-phenyl)-[1,2,4]oxadiazol-5-yl]-azetidin-1-yl}-(5-methyl-2-[1,2,3]triazol-2-yl-phenyl)-methanone; LC-MS A: $t_R$ = 0.89 min; [M + H]$^+$ = 435.03 |
| 17 | A-3-4 | A-4-13 | E | {(S)-2-[3-(3-Fluoro-2-methoxy-phenyl)-[1,2,4]oxadiazol-5-yl]-azetidin-1-yl}-(5-methoxy-4-methyl-2-[1,2,3]triazol-2-yl-phenyl)-methanone; LC-MS A: $t_R$ = 0.92 min; [M + H]$^+$ = 645.01 |
| 18 | A-3-2 | A-4-13 | E | (4,5-Dimethyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R$ = 0.92 min; [M + H]$^+$ = 448.96 |
| 19 | A-3-2 | A-4-7 | E | {(S)-2-[3-(3-Fluoro-2-methoxy-phenyl)-[1,2,4]oxadiazol-5-yl]-azetidin-1-yl}-(4-methyl-2-[1,2,3]triazol-2-yl-phenyl)-methanone; LC-MS A: $t_R$ = 0.97 min; [M + H]$^+$ = 484.99 |
| 20 | A-3-3 | A-4-13 | E | {(S)-2-[3-(3-Fluoro-2-methoxy-phenyl)-[1,2,4]oxadiazol-5-yl]-azetidin-1-yl}-(4-methyl-2-[1,2,3]triazol-2-yl-phenyl)-methanone; LC-MS A: $t_R$ = 0.89 min; [M + H]$^+$ = 435.03 |
| 21 | A-3-2 | A-4-12 | E | (4,5-Dimethyl-2-[1,2,3]triazol-2-yl-phenyl)-{(S)-2-[3-(3-fluoro-2-methyl-phenyl)-[1,2,4]oxadiazol-5-yl]-azetidin-1-yl}-methanone; LC-MS A: $t_R$ = 0.96 min; [M + H]$^+$ = 432.99 |
| 22 | A-3-3 | A-4-12 | E | {(S)-2-[3-(3-Fluoro-2-methyl-phenyl)-[1,2,4]oxadiazol-5-yl]-azetidin-1-yl}-(4-methyl-2-[1,2,3]triazol-2-yl-phenyl)-methanone; LC-MS A: $t_R$ = 0.93 min; [M + H]$^+$ = 419.07 |
| 23 | A-3-5 | A-4-7 | E | (4-Fluoro-5-methoxy-2-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R$ = 0.95 min; [M + H]$^+$ = 505.03 |
| 24 | A-3-5 | A-4-11 | E | {(S)-2-[3-(3-Chloro-2-methyl-phenyl)-[1,2,4]oxadiazol-5-yl]-azetidin-1-yl}-(4-fluoro-5-methoxy-2-[1,2,3]triazol-2-yl-phenyl)-methanone; LC-MS A: $t_R$ = 0.96 min; [M($^{35}$Cl) + H]$^+$ = 469.01 |
| 25 | A-3-5 | A-4-12 | E | (4-Fluoro-5-methoxy-2-[1,2,3]triazol-2-yl-phenyl)-{(S)-2-[3-(3-fluoro-2-methyl-phenyl)-[1,2,4]oxadiazol-5-yl]-azetidin-1-yl}-methanone; LC-MS A: $t_R$ = 0.93 min; [M + H]$^+$ = 453.04 |
| 26 | A-3-5 | A-4-13 | E | {(S)-2-[3-(3-Fluoro-2-methoxy-phenyl)-[1,2,4]oxadiazol-5-yl]-azetidin-1-yl}-(4-fluoro-5-methoxy-2-[1,2,3]triazol-2-yl-phenyl)-methanone; LC-MS A: $t_R$ = 0.9 min; [M + H]$^+$ = 469.03 |
| 27 | A-3-4 | A-4-7 | E | (5-Methoxy-4-methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R$ = 0.97 min; [M + H]$^+$ = 501.12 |
| 28 | A-3-4 | A-4-11 | E | {(S)-2-[3-(3-Chloro-2-methyl-phenyl)-[1,2,4]oxadiazol-5-yl]-azetidin-1-yl}-(5-methoxy-4-methyl-2-[1,2,3]triazol-2-yl-phenyl)-methanone; LC-MS A: $t_R$ = 0.97 min; [M($^{35}$Cl) + H]$^+$ = 465.00 |
| 29 | A-3-4 | A-4-12 | E | {(S)-2-[3-(3-Fluoro-2-methyl-phenyl)-[1,2,4]oxadiazol-5-yl]-azetidin-1-yl}-(5-methoxy-4-methyl-2-[1,2,3]triazol-2-yl-phenyl)-methanone; LC-MS A: $t_R$ = 0.95 min; [M + H]$^+$ = 449.02 |
| 30 | A-3-1 | A-4-14 | E | {(S)-2-[3-(2-Ethoxy-pyridin-3-yl)-[1,2,4]oxadiazol-5-yl]-azetidin-1-yl}-(5-methyl-2-[1,2,3]triazol-2-yl-phenyl)-methanone; LC-MS A: $t_R$ = 0.86 min; [M + H]$^+$ = 432.08 |
| 31 | A-3-2 | A-4-14 | E | (4,5-Dimethyl-2-[1,2,3]triazol-2-yl-phenyl)-{(S)-2-[3-(2-ethoxy-pyridin-3-yl)-[1,2,4]oxadiazol-5-yl]-azetidin-1-yl}-methanone; LC-MS A: $t_R$ = 0.89 min; [M + H]$^+$ = 446.11 |
| 32 | A-3-3 | A-4-14 | E | {(S)-2-[3-(2-Ethoxy-pyridin-3-yl)-[1,2,4]oxadiazol-5-yl]-azetidin-1-yl}-(4-methyl-2-[1,2,3]triazol-2-yl-phenyl)-methanone; LC-MS A: $t_R$ = 0.86 min; [M + H]$^+$ = 432.08 |
| 33 | A-3-5 | A-4-14 | E | {(S)-2-[3-(2-Ethoxy-pyridin-3-yl)-[1,2,4]oxadiazol-5-yl]-azetidin-1-yl}-(4-fluoro-5-methoxy-2-[1,2,3]triazol-2-yl-phenyl)-methanone; LC-MS A: $t_R$ = 0.87 min; [M + H]$^+$ = 465.79 |
| 34 | A-3-4 | A-4-14 | E | {(S)-2-[3-(2-Ethoxy-pyridin-3-yl)-[1,2,4]oxadiazol-5-yl]-azetidin-1-yl}-(5- |

TABLE 13-continued

| Ex. No. | SM A-3 | SM A-4 | GM | Compound of Formula (I) |
|---|---|---|---|---|
| | | | | methoxy-4-methyl-2-[1,2,3]triazol-2-yl-phenyl)-methanone; LC-MS A: $t_R = 0.89$ min; $[M + H]^+ = 462.15$ |
| 35 | A-3-1 | A-4-16 | D | {(S)-2-[3-(2-Cyclobutoxy-pyridin-3-yl)-[1,2,4]oxadiazol-5-yl]-azetidin-1-yl}-(5-methyl-2-[1,2,3]triazol-2-yl-phenyl)-methanone; LC-MS A: $t_R = 0.92$ min; $[M + H]^+ = 458.11$ |

General Method F for Amide Formation

TBTU/DIPEA DMF

Example 36

(5-Methyl-2-[1,2,3]triazol-2-yl-phenyl)-[(S)-2-(3-phenyl-[1,2,4]oxadiazol-5-yl)-azetidin-1-yl]-methanone TBTU (1.1 mmol) was added to a solution of carboxylic acid A-1-2 (1.0 mmol) and DIPEA (2.0 mmol) in DMF (2.0 mL). After stirring at rt for 10 min a solution of amine B-3-1 (1.0 mmol) in DMF (1.0 mL) was added. The resulting rxn mixture was stirred at rt for up to 3 d before being purified directly by prep. HPLC (method E) to furnish the desired product. LC-MS A: $t_R=0.88$ min; $[M+H]^+=386.92$.

Listed in Table 14 below are example compounds, prepared according to the above mentioned General Method F, from corresponding carboxylic acid A-1 and amine B-3.

TABLE 14

| Ex. No. | SM A-1 | SM B-3 | Compound of Formula (I) |
|---|---|---|---|
| 37 | A-1-18 | B-3-2 | [5-(2-Fluoro-phenyl)-2-methyl-thiazol-4-yl]-{(S)-2-[3-(2-trifluoromethoxy-phenyl)-[1,2,4]oxadiazol-5-yl]-azetidin-1-yl}-methanone; LC-MS A: $t_R = 1.0$ min; $[M + H]^+ = 504.95$ |
| 38 | A-1-21 | B-3-2 | (2-Methyl-5-m-tolyl-thiazol-4-yl)-{(S)-2-[3-(2-trifluoromethoxy-phenyl)-[1,2,4]oxadiazol-5-yl]-azetidin-1-yl}-methanone; LC-MS A: $t_R = 1.02$ min; $[M + H]^+ = 500.91$ |
| 39 | A-1-14 | B-3-2 | (4-Methyl-biphenyl-2-yl)-{(S)-2-[3-(2-trifluoromethoxy-phenyl)-[1,2,4]oxadiazol-5-yl]-azetidin-1-yl}-methanone; LC-MS A: $t_R = 1.03$ min; $[M + H]^+ = 479.99$ |
| 40 | A-1-24 | B-3-2 | (2-Methyl-5-phenyl-thiazol-4-yl)-{(S)-2-[3-(2-trifluoromethoxy-phenyl)-[1,2,4]oxadiazol-5-yl]-azetidin-1-yl}-methanone; LC-MS A: $t_R = 0.99$ min; $[M + H]^+ = 486.89$ |
| 41 | A-1-27 | B-3-2 | (2-Dimethylamino-5-phenyl-thiazol-4-yl)-{(S)-2-[3-(2-trifluoromethoxy-phenyl)-[1,2,4]oxadiazol-5-yl]-azetidin-1-yl}-methanone; LC-MS A: $t_R = 1.01$ min; $[M + H]^+ = 515.64$ |
| 42 | A-1-25 | B-3-3 | (5-Phenyl-thiazol-4-yl)-{(S)-2-[3-(2-trifluoromethoxy-phenyl)-[1,2,4]oxadiazol-5-yl]-azetidin-1-yl}-methanone; LC-MS A: $t_R = 0.96$ min; $[M + H]^+ = 472.91$ |
| 43 | A-1-17 | B-3-2 | [5-(3-Chloro-phenyl)-thiazol-4-yl]-{(S)-2-[3-(2-trifluoromethoxy-phenyl)-[1,2,4]oxadiazol-5-yl]-azetidin-1-yl}-methanone; $[M(^{35}Cl) + H]^+ = 506.82$ |
| 44 | A-1-28 | B-3-2 | (2-Methyl-5-p-tolyl-thiazol-4-yl)-{(S)-2-[3-(2-trifluoromethoxy-phenyl)-[1,2,4]oxadiazol-5-yl]-azetidin-1-yl}-methanone; LC-MS A: $t_R = 1.2$ min; $[M + H]^+ = 500.95$ |
| 45 | A-1-29 | B-3-2 | (2-Methyl-5-o-tolyl-thiazol-4-yl)-{(S)-2-[3-(2-trifluoromethoxy-phenyl)-[1,2,4]oxadiazol-5-yl]-azetidin-1-yl}-methanone; LC-MS A: $t_R = 1.03$ min; $[M + H]^+ = 500.89$ |
| 46 | A-1-13 | B-3-2 | (2-Methyl-6-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R = 0.94$ min; $[M + H]^+ = 471.10$ |
| 47 | A-1-9 | B-3-2 | (2-[1,2,3]Triazol-2-yl-5-trifluoromethoxy-phenyl)-{(S)-2-[3-(2-trifluoromethoxy-phenyl)-[1,2,4]oxadiazol-5-yl]-azetidin-1-yl}-methanone; LC-MS A: $t_R = 0.99$ min; $[M + H]^+ = 541.06$ |
| 48 | A-1-12 | B-3-2 | (2-[1,2,3]Triazol-2-yl-5-trifluoromethyl-phenyl)-{(S)-2-[3-(2-trifluoromethoxy-phenyl)-[1,2,4]oxadiazol-5-yl]-azetidin-1-yl}-methanone; LC-MS A: $t_R = 0.98$ min; $[M + H]^+ = 525.07$ |
| 49 | A-1-31 | B-3-2 | (5-m-Tolyl-oxazol-4-yl)-{(S)-2-[3-(2-trifluoromethoxy-phenyl)-[1,2,4]oxadiazol-5-yl]-azetidin-1-yl}-methanone; LC-MS A: $t_R = 1.0$ min; $[M + H]^+ = 471.08$ |
| 50 | A-1-4 | B-3-2 | (2-[1,2,3]Triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R = 0.92$ min; $[M + H]^+ = 456.93$ |
| 51 | A-1-26 | B-3-2 | (5-m-Tolyl-thiazol-4-yl)-{(S)-2-[3-(2-trifluoromethoxy-phenyl)-[1,2,4]oxadiazol-5-yl]-azetidin-1-yl}-methanone; LC-MS A: $t_R = 0.99$ min; $[M + H]^+ = 486.99$ |
| 52 | A-1-20 | B-3-2 | (2-Methyl-5-m-tolyl-oxazol-4-yl)-{(S)-2-[3-(2-trifluoromethoxy-phenyl)-[1,2,4]oxadiazol-5-yl]-azetidin-1-yl}-methanone; LC-MS A: $t_R = 1.02$ min; $[M + H]^+ = 484.96$ |
| 53 | A-1-23 | B-3-2 | [3-(2-Chloro-phenyl)-5-methyl-isoxazol-4-yl]-{(S)-2-[3-(2-trifluoromethoxy-phenyl)-[1,2,4]oxadiazol-5-yl]-azetidin-1-yl}-methanone; LC-MS A: $t_R = 0.97$ min; $[M(^{35}Cl) + H]^+ = 505.05$ |
| 54 | A-1-19 | B-3-2 | Biphenyl-2-yl-{(S)-2-[3-(2-trifluoromethoxy-phenyl)-[1,2,4]oxadiazol-5-yl]-azetidin-1-yl}-methanone; LC-MS A: $t_R = 1.0$ min; $[M + H]^+ = 466.10$ |
| 55 | A-1-18 | B-3-3 | {(S)-2-[3-(3-Chloro-2-methyl-phenyl)-[1,2,4]oxadiazol-5-yl]-azetidin-1-yl}-[5-(2-fluoro-phenyl)-2-methyl-thiazol-4-yl]-methanone; LC-MS A: $t_R = 1.02$ min; $[M(^{35}Cl) + H]^+ = 468.94$ |
| 56 | A-1-21 | B-3-3 | {(S)-2-[3-(3-Chloro-2-methyl-phenyl)-[1,2,4]oxadiazol-5-yl]-azetidin-1-yl}-(2-methyl-5-m-tolyl-thiazol-4-yl)-methanone; LC-MS A: $t_R = 1.03$ min; $[M(^{35}Cl) + H]^+ = 464.97$ |
| 57 | A-1-14 | B-3-3 | {(S)-2-[3-(3-Chloro-2-methyl-phenyl)-[1,2,4]oxadiazol-5-yl]-azetidin-1-yl}-(4-methyl-biphenyl-2-yl)-methanone; LC-MS A: $t_R = 1.04$ min; $[M(^{35}Cl) + H]^+ = 444.01$ |
| 58 | A-1-24 | B-3-3 | {(S)-2-[3-(3-Chloro-2-methyl-phenyl)-[1,2,4]oxadiazol-5-yl]-azetidin-1-yl}-(2-methyl-5-phenyl-thiazol-4-yl)-methanone; LC-MS A: $t_R = 1.01$ min; $[M(^{35}Cl) + H]^+ = 450.99$ |
| 59 | A-1-27 | B-3-3 | {(S)-2-[3-(3-Chloro-2-methyl-phenyl)-[1,2,4]oxadiazol-5-yl]-azetidin-1-yl}-(2-dimethylamino-5-phenyl-thiazol-4-yl)-methanone; LC-MS A: $t_R = 1.02$ min; $[M(^{35}Cl) + H]^+ = 479.97$ |
| 60 | A-1-25 | B-3-3 | {(S)-2-[3-(3-Chloro-2-methyl-phenyl)-[1,2,4]oxadiazol-5-yl]-azetidin-1-yl}-(5-phenyl-thiazol-4-yl)-methanone; LC-MS A: $t_R = 0.98$ min; $[M(^{35}Cl) + H]^+ = 436.61$ |
| 61 | A-1-17 | B-3-3 | {(S)-2-[3-(3-Chloro-2-methyl-phenyl)-[1,2,4]oxadiazol-5-yl]-azetidin-1-yl}-[5-(3-chloro-phenyl)-thiazol-4-yl]-methanone; LC-MS A: $t_R = 1.02$ min; $[M(^{35}Cl) + H]^+ = 470.92$ |
| 62 | A-1-28 | B-3-3 | {(S)-2-[3-(3-Chloro-2-methyl-phenyl)-[1,2,4]oxadiazol-5-yl]-azetidin-1-yl}-(2-methyl-5-p-tolyl-thiazol-4-yl)-methanone; LC-MS A: $t_R = 1.04$ min; $[M(^{35}Cl) + H]^+ = 464.93$ |
| 63 | A-1-29 | B-3-3 | {(S)-2-[3-(3-Chloro-2-methyl-phenyl)-[1,2,4]oxadiazol-5-yl]-azetidin-1-yl}-(2-methyl-5-o-tolyl-thiazol-4-yl)-methanone; LC-MS A: $t_R = 1.05$ min; $[M(^{35}Cl) + H]^+ = 464.97$ |

TABLE 14-continued

| Ex. No. | SM A-1 | SM B-3 | Compound of Formula (I) |
|---|---|---|---|
| 64 | A-1-13 | B-3-3 | {(S)-2-[3-(3-Chloro-2-methyl-phenyl)-[1,2,4]oxadiazol-5-yl]-azetidin-1-yl}-(2-methyl-6-[1,2,3]triazol-2-yl-phenyl)-methanone; LC-MS A: $t_R$ = 0.96 min; [M($^{35}$Cl) + H]$^+$ = 434.97 |
| 65 | A-1-9 | B-3-3 | {(S)-2-[3-(3-Chloro-2-methyl-phenyl)-[1,2,4]oxadiazol-5-yl]-azetidin-1-yl}-(2-[1,2,3]triazol-2-yl-5-trifluoromethoxy-phenyl)-methanone; LC-MS A: $t_R$ = 1.01 min; [M($^{35}$Cl) + H]$^+$ = 504.8 |
| 66 | A-1-12 | B-3-3 | {(S)-2-[3-(3-Chloro-2-methyl-phenyl)-[1,2,4]oxadiazol-5-yl]-azetidin-1-yl}-(2-[1,2,3]triazol-2-yl-5-trifluoromethyl-phenyl)-methanone; LC-MS A: $t_R$ = 1.0 min; [M($^{35}$Cl) + H]$^+$ = 489.0 |
| 67 | A-1-31 | B-3-3 | {(S)-2-[3-(3-Chloro-2-methyl-phenyl)-[1,2,4]oxadiazol-5-yl]-azetidin-1-yl}-(5-m-tolyl-oxazol-4-yl)-methanone; LC-MS A: $t_R$ = 1.01 min; [M($^{35}$Cl) + H]$^+$ = 434.96 |
| 68 | A-1-4 | B-3-3 | {(S)-2-[3-(3-Chloro-2-methyl-phenyl)-[1,2,4]oxadiazol-5-yl]-azetidin-1-yl}-(2-[1,2,3]triazol-2-yl-phenyl)-methanone; LC-MS A: $t_R$ = 0.93 min; [M($^{35}$Cl) + H]$^+$ = 420.92 |
| 69 | A-1-26 | B-3-3 | {(S)-2-[3-(3-Chloro-2-methyl-phenyl)-[1,2,4]oxadiazol-5-yl]-azetidin-1-yl}-(5-m-tolyl-thiazol-4-yl)-methanone; LC-MS A: $t_R$ = 1.01 min; [M($^{35}$Cl) + H]$^+$ = 451.00 |
| 70 | A-1-6 | B-3-3 | {(S)-2-[3-(3-Chloro-2-methyl-phenyl)-[1,2,4]oxadiazol-5-yl]-azetidin-1-yl}-(4,5-dimethyl-2-[1,2,3]triazol-2-yl-phenyl)-methanone; LC-MS A: $t_R$ = 0.99 min; [M($^{35}$Cl) + H]$^+$ = 449.10 |
| 71 | A-1-20 | B-3-3 | {(S)-2-[3-(3-Chloro-2-methyl-phenyl)-[1,2,4]oxadiazol-5-yl]-azetidin-1-yl}-(2-methyl-5-m-tolyl-oxazol-4-yl)-methanone; LC-MS A: $t_R$ = 1.03 min; [M($^{35}$Cl) + H]$^+$ = 449.00 |
| 72 | A-1-23 | B-3-3 | {(S)-2-[3-(3-Chloro-2-methyl-phenyl)-[1,2,4]oxadiazol-5-yl]-azetidin-1-yl}-[3-(2-chloro-phenyl)-5-methyl-isoxazol-4-yl]-methanone; LC-MS A: $t_R$ = 1.00 min; [M($^{35}$Cl) + H]$^+$ = 468.90 |
| 73 | A-1-19 | B-3-3 | Biphenyl-2-yl-{(S)-2-[3-(3-chloro-2-methyl-phenyl)-[1,2,4]oxadiazol-5-yl]-azetidin-1-yl}-methanone; LC-MS A: $t_R$ = 1.01 min; [M($^{35}$Cl) + H]$^+$ = 430.10 |
| 74 | A-1-7 | B-3-3 | (4-Chloro-5-methoxy-2-[1,2,3]triazol-2-yl-phenyl)-{(S)-2-[3-(3-chloro-2-methyl-phenyl)-[1,2,4]oxadiazol-5-yl]-azetidin-1-yl}-methanone; LC-MS A: $t_R$ = 0.99 min; [M($^{35}$Cl) + H]$^+$ = 484.99 |
| 75 | A-1-7 | B-3-2 | (4-Chloro-5-methoxy-2-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R$ = 0.97 min; [M($^{35}$Cl) + H]$^+$ = 520.99 |
| 76 | A-1-1 | B-3-3 | {(S)-2-[3-(3-Chloro-2-methyl-phenyl)-[1,2,4]oxadiazol-5-yl]-azetidin-1-yl}-(4-chloro-2-[1,2,3]triazol-2-yl-phenyl)-methanone; LC-MS A: $t_R$ = 0.98 min; [M($^{35}$Cl) + H]$^+$ = 454.99 |
| 77 | A-1-1 | B-3-2 | (4-Chloro-2-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R$ = 0.97 min; [M($^{35}$Cl) + H]$^+$ = 490.88 |
| 78 | A-1-3 | B-3-3 | {(S)-2-[3-(3-Chloro-2-methyl-phenyl)-[1,2,4]oxadiazol-5-yl]-azetidin-1-yl}-(4-methyl-2-[1,2,3]triazol-2-yl-phenyl)-methanone; LC-MS A: $t_R$ = 0.96 min; [M($^{35}$Cl) + H]$^+$ = 434.89 |
| 79 | A-1-3 | B-3-2 | (4-Methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R$ = 0.95 min; [M + H]$^+$ = 471.07 |
| 80 | A-1-5 | B-3-3 | {(S)-2-[3-(3-Chloro-2-methyl-phenyl)-[1,2,4]oxadiazol-5-yl]-azetidin-1-yl}-(5-chloro-2-[1,2,3]triazol-2-yl-phenyl)-methanone; LC-MS A: $t_R$ = 0.98 min; [M($^{35}$Cl) + H]$^+$ = 455.01 |
| 81 | A-1-5 | B-3-2 | (5-Chloro-2-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R$ = 0.97 min; [M($^{35}$Cl) + H]$^+$ = 490.91 |
| 82 | A-1-15 | B-3-3 | {(S)-2-[3-(3-Chloro-2-methyl-phenyl)-[1,2,4]oxadiazol-5-yl]-azetidin-1-yl}-(5-chloro-4-methyl-2-[1,2,3]triazol-2-yl-phenyl)-methanone; LC-MS A: $t_R$ = 1.01 min; [M($^{35}$Cl) + H]$^+$ = 469.01 |
| 83 | A-1-15 | B-3-2 | (5-Chloro-4-methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone; LC-MS A: $t_R$ = 0.99 min; [M($^{35}$Cl) + H]$^+$ = 505.01 |

General Method G for Amide Formation

TBTU/DIPEA DMF

Example 84

(5-Methyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone Step A:

TBTU (68 mg, 0.21 mmol) was added to a solution of carboxylic acid A-1-2 (43 mg, 0.21 mmol) and DIPEA (70 uL, 0.41 mmol) in DMF (0.7 mL). After stirring at rt for 15 min a solution of amine C-7-4 (50 mg) in DMF (0.5 mL) was added. The resulting rxn mixture was stirred at rt for up to 3 d before being purified directly by prep. HPLC (method D) followed by prep. TLC (EtOAc/hept 7:3) to furnish the desired product. LC-MS A: $t_R$=0.94 min; [M+H]$^+$=471.41.

Listed in Table 15 below are compounds of structure of formula (I), prepared according to the above procedure (General Method G).

TABLE 15

| Ex. No. | SM C-7 | SM A-1 | Compound of Formula (I) |
|---|---|---|---|
| 85 | C-7-4 | A-1-6 | (4,5-Dimethyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone; LC-MS A: $t_R$ = 0.96 min; [M + H]$^+$ = 485.07 |
| 86 | C-7-4 | A-1-11 | (5-Methoxy-4-methyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone; LC-MS A: $t_R$ = 0.96 min; [M + H]$^+$ = 501.07 |
| 87 | C-7-4 | A-1-8 | (4-Fluoro-5-methoxy-2-[1,2,3]triazol-2-yl-phenyl)-{(S)-2-[5-(2-trifluoromethoxy-phenyl)-[1,2,4]oxadiazol-3-yl]-azetidin-1-yl}-methanone; LC-MS A: $t_R$ = 0.94 min; [M + H]$^+$ = 505.05 |
| 88 | C-7-2 | A-1-11 | {(S)-2-[5-(3-Fluoro-2-methoxy-phenyl)-[1,2,4]oxadiazol-3-yl]-azetidin-1-yl}-(5-methoxy-4-methyl-2-[1,2,3]triazol-2-yl-phenyl)-methanone; LC-MS A: $t_R$ = 0.91 min; [M + H]$^+$ = 465.01 |
| 89 | C-7-3 | A-1-6 | (4,5-Dimethyl-2-[1,2,3]triazol-2-yl-phenyl)-{(S)-2-[5-(3-fluoro-2-methyl-phenyl)-[1,2,4]oxadiazol-3-yl]-azetidin-1-yl}-methanone; LC-MS A: $t_R$ = 0.95 min; [M + H]$^+$ = 433.03 |
| 90 | C-7-6 | A-1-2 | {(S)-2-[5-(2-Ethoxy-pyridin-3-yl)-[1,2,4]oxadiazol-3-yl]-azetidin-1-yl}-(5-methyl-2-[1,2,3]triazol-2-yl-phenyl)-methanone; LC-MS A: $t_R$ = 0.87 min; [M + H]$^+$ = 432.12 |
| 91 | C-7-6 | A-1-6 | (4,5-Dimethyl-2-[1,2,3]triazol-2-yl-phenyl)-{(S)-2-[5-(2-ethoxy-pyridin-3-yl)-[1,2,4]oxadiazol-3-yl]-azetidin-1-yl}-methanone; LC-MS A: $t_R$ = 0.9 min; [M + H]$^+$ = 446.10 |

TABLE 15-continued

| Ex. No. | SM C-7 | SM A-1 | Compound of Formula (I) |
|---|---|---|---|
| 92 | C-7-6 | A-1-11 | {(S)-2-[5-(2-Ethoxy-pyridin-3-yl)-[1,2,4]oxadiazol-3-yl]-azetidin-1-yl}-(5-methoxy-4-methyl-2-[1,2,3]triazol-2-yl-phenyl)-methanone; LC-MS A: $t_R$ = 0.89 min; [M + H]$^+$ = 462.10 |
| 93 | C-7-3 | A-1-2 | {(S)-2-[5-(3-Fluoro-2-methyl-phenyl)-[1,2,4]oxadiazol-3-yl]-azetidin-1-yl}-(5-methyl-2-[1,2,3]triazol-2-yl-phenyl)-methanone; LC-MS A: $t_R$ = 0.93 min; [M + H]$^+$ = 418.99 |
| 94 | C-7-4 | A-1-7 | (4-Chloro-5-methoxy-2-[1,2,3]triazol-2-yl-phenyl)-{(S)-2-[5-(2-trifluoromethoxy-phenyl)-[1,2,4]oxadiazol-3-yl]-azetidin-1-yl}-methanone; LC-MS A: $t_R$ = 0.97 min; [M($^{35}$Cl) + H]$^+$ = 520.82 |
| 95 | C-7-4 | A-1-15 | (5-Chloro-4-methyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone; LC-MS A: $t_R$ = 0.98 min; [M($^{35}$Cl) + H]$^+$ = 504.93 |
| 96 | C-7-3 | A-1-7 | (4-Chloro-5-methoxy-2-[1,2,3]triazol-2-yl-phenyl)-{(S)-2-[5-(3-fluoro-2-methyl-phenyl)-[1,2,4]oxadiazol-3-yl]-azetidin-1-yl}-methanone; LC-MS A: $t_R$ = 0.96 min; [M($^{35}$Cl) + H]$^+$ = 470.06 |
| 97 | C-7-6 | A-1-3 | {(S)-2-[5-(2-Ethoxy-pyridin-3-yl)-[1,2,4]oxadiazol-3-yl]-azetidin-1-yl}-(4-methyl-2-[1,2,3]triazol-2-yl-phenyl)-methanone; LC-MS A: $t_R$ = 0.87 min; [M + H]$^+$ = 432.08 |
| 98 | C-7-6 | A-1-7 | (4-Chloro-5-methoxy-2-[1,2,3]triazol-2-yl-phenyl)-{(S)-2-[5-(2-ethoxy-pyridin-3-yl)-[1,2,4]oxadiazol-3-yl]-azetidin-1-yl}-methanone; LC-MS A: $t_R$ = 0.90 min; [M($^{35}$Cl) + H]$^+$ = 482.00 |
| 99 | C-7-6 | A-1-15 | (5-Chloro-4-methyl-2-[1,2,3]triazol-2-yl-phenyl)-{(S)-2-[5-(2-ethoxy-pyridin-3-yl)-[1,2,4]oxadiazol-3-yl]-azetidin-1-yl}-methanone; LC-MS A: $t_R$ = 0.92 min; [M($^{35}$Cl) + H]$^+$ = 466.04 |
| 100 | C-7-1 | A-1-4 | {(S)-2-[5-(3-Chloro-2-methyl-phenyl)-[1,2,4]oxadiazol-3-yl]-azetidin-1-yl}-(2-[1,2,3]triazol-2-yl-phenyl)-methanone; LC-MS A: $t_R$ = 0.92 min; [M($^{35}$Cl) + H]$^+$ = 421.04 |
| 101 | C-7-1 | A-1-2 | {(S)-2-[5-(3-Chloro-2-methyl-phenyl)-[1,2,4]oxadiazol-3-yl]-azetidin-1-yl}-(5-methyl-2-[1,2,3]triazol-2-yl-phenyl)-methanone; LC-MS A: $t_R$ = 0.95 min; [M($^{35}$Cl) + H]$^+$ = 434.92 |
| 102 | C-7-1 | A-1-6 | {(S)-2-[5-(3-Chloro-2-methyl-phenyl)-[1,2,4]oxadiazol-3-yl]-azetidin-1-yl}-(4,5-dimethyl-2-[1,2,3]triazol-2-yl-phenyl)-methanone; LC-MS A: $t_R$ = 0.98 min; [M($^{35}$Cl) + H]$^+$ = 449.08 |
| 103 | C-7-1 | A-1-11 | {(S)-2-[5-(3-Chloro-2-methyl-phenyl)-[1,2,4]oxadiazol-3-yl]-azetidin-1-yl}-(5-methoxy-4-methyl-2-[1,2,3]triazol-2-yl-phenyl)-methanone; LC-MS A: $t_R$ = 0.97 min; [M($^{35}$Cl) + H]$^+$ = 465.06 |
| 104 | C-7-1 | A-1-7 | (4-Chloro-5-methoxy-2-[1,2,3]triazol-2-yl-phenyl)-{(S)-2-[5-(3-chloro-2-methyl-phenyl)-[1,2,4]oxadiazol-3-yl]-azetidin-1-yl}-methanone; LC-MS A: $t_R$ = 0.98 min; [M($^{35}$Cl) + H]$^+$ = 484.99 |
| 105 | C-7-1 | A-1-15 | {(S)-2-[5-(3-Chloro-2-methyl-phenyl)-[1,2,4]oxadiazol-3-yl]-azetidin-1-yl}-(5-chloro-4-methyl-2-[1,2,3]triazol-2-yl-phenyl)-methanone; LC-MS A: $t_R$ = 1.00 min; [M($^{35}$Cl) + H]$^+$ = 469.01 |
| 106 | C-7-1 | A-1-3 | {(S)-2-[5-(3-Chloro-2-methyl-phenyl)-[1,2,4]oxadiazol-3-yl]-azetidin-1-yl}-(4-methyl-2-[1,2,3]triazol-2-yl-phenyl)-methanone; LC-MS A: $t_R$ = 0.95 min; [M($^{35}$Cl) + H]$^+$ = 434.92 |
| 107 | C-7-1 | A-1-1 | {(S)-2-[5-(3-Chloro-2-methyl-phenyl)-[1,2,4]oxadiazol-3-yl]-azetidin-1-yl}-(4-chloro-2-[1,2,3]triazol-2-yl-phenyl)-methanone; LC-MS A: $t_R$ = 0.98 min; [M($^{35}$Cl) + H]$^+$ = 455.00 |
| 108 | C-7-1 | A-1-10 | {(S)-2-[5-(3-Chloro-2-methyl-phenyl)-[1,2,4]oxadiazol-3-yl]-azetidin-1-yl}-(2-[1,2,3]triazol-2-yl-4-trifluoromethyl-phenyl)-methanone; LC-MS A: $t_R$ = 1.00 min; [M($^{35}$Cl) + H]$^+$ = 489.01 |
| 109 | C-7-5 | A-1-2 | {(S)-2-[5-(3-Chloro-2-methoxy-phenyl)-[1,2,4]oxadiazol-3-yl]-azetidin-1-yl}-(5-methyl-2-[1,2,3]triazol-2-yl-phenyl)-methanone; LC-MS A: $t_R$ = 0.92 min; [M($^{35}$Cl) + H]$^+$ = 450.92 |
| 110 | C-7-5 | A-1-6 | {(S)-2-[5-(3-Chloro-2-methoxy-phenyl)-[1,2,4]oxadiazol-3-yl]-azetidin-1-yl}-(4,5-dimethyl-2-[1,2,3]triazol-2-yl-phenyl)-methanone; LC-MS A: $t_R$ = 0.94 min; [M($^{35}$Cl) + H]$^+$ = 465.06 |
| 111 | C-7-5 | A-1-11 | {(S)-2-[5-(3-Chloro-2-methoxy-phenyl)-[1,2,4]oxadiazol-3-yl]-azetidin-1-yl}-(5-methoxy-4-methyl-2-[1,2,3]triazol-2-yl-phenyl)-methanone; LC-MS A: $t_R$ = 0.94 min; [M($^{35}$Cl) + H]$^+$ = 481.06 |
| 112 | C-7-5 | A-1-7 | {(S)-2-[5-(3-Chloro-2-methoxy-phenyl)-[1,2,4]oxadiazol-3-yl]-azetidin-1-yl}-(4-chloro-5-methoxy-2-[1,2,3]triazol-2-yl-phenyl)-methanone; LC-MS A: $t_R$ = 0.95 min; [M($^{35}$Cl) + H]$^+$ = 501.00 |
| 113 | C-7-5 | A-1-15 | {(S)-2-[5-(3-Chloro-2-methoxy-phenyl)-[1,2,4]oxadiazol-3-yl]-azetidin-1-yl}-(5-chloro-4-methyl-2-[1,2,3]triazol-2-yl-phenyl)-methanone; LC-MS A: $t_R$ = 0.97 min; [M($^{35}$Cl) + H]$^+$ = 484.99 |
| 114 | C-7-1 | A-1-14 | {(S)-2-[5-(3-Chloro-2-methyl-phenyl)-[1,2,4]oxadiazol-3-yl]-azetidin-1-yl}-(4-methyl-biphenyl-2-yl)-methanone; LC-MS A: $t_R$ = 1.04 min; [M($^{35}$Cl) + H]$^+$ = 444.07 |
| 115 | C-7-1 | A-1-30 | {(S)-2-[5-(3-Chloro-2-methyl-phenyl)-[1,2,4]oxadiazol-3-yl]-azetidin-1-yl}-(5-fluoro-2-pyrimidin-2-yl-phenyl)-methanone; LC-MS A: $t_R$ = 0.94 min; [M($^{35}$Cl) + H]$^+$ = 450.0 |
| 116 | C-7-1 | A-1-16 | {(S)-2-[5-(3-Chloro-2-methyl-phenyl)-[1,2,4]oxadiazol-3-yl]-azetidin-1-yl}-(5-methoxy-4-methyl-2-pyrimidin-2-yl-phenyl)-methanone; LC-MS A: $t_R$ = 0.96 min; [M($^{35}$Cl) + H]$^+$ = 476.07 |
| 117 | C-7-1 | A-1-22 | {(S)-2-[5-(3-Chloro-2-methyl-phenyl)-[1,2,4]oxadiazol-3-yl]-azetidin-1-yl}-(5-methyl-2-pyrimidin-2-yl-phenyl)-methanone; LC-MS A: $t_R$ = 0.94 min; [M($^{35}$Cl) + H]$^+$ = 446.08 |
| 118 | C-7-5 | A-1-3 | {(S)-2-[5-(3-Chloro-2-methoxy-phenyl)-[1,2,4]oxadiazol-3-yl]-azetidin-1-yl}-(4-methyl-2-[1,2,3]triazol-2-yl-phenyl)-methanone; LC-MS A: $t_R$ = 0.91 min; [M($^{35}$Cl) + H]$^+$ = 451.05 |
| 119 | C-7-5 | A-1-1 | {(S)-2-[5-(3-Chloro-2-methoxy-phenyl)-[1,2,4]oxadiazol-3-yl]-azetidin-1-yl}-(4-chloro-2-[1,2,3]triazol-2-yl-phenyl)-methanone; LC-MS A: $t_R$ = 0.94 min; [M($^{35}$Cl) + H]$^+$ = 471.04 |

General Method H for Amide Formation

HATU/DIPEA DMF

Example 120

(5-Methyl-2-[1,2,3]triazol-2-yl-phenyl)-[(S)-2-(5-phenyl-4H-[1,2,4]triazol-3-yl)-azetidin-1-yl]-methanone HATU (49 mg, 0.13 mmol) was added to a rt solution of carboxylic acid A-1-2 (25 mg, 0.12 mmol) and DIPEA (105 uL, 0.62 mmol) in DMF (1.0 mL), the rxn mixture was stirred at rt for 10 min, before D-3-1 (34 mg, 0.12 mmol) was added and stirring was continued for 18 h. The rxn mixture was directly purified by prep. HPLC (method E) to give the title compound as a white solid. LC-MS A: $t_R$=0.71 min; [M+H]$^+$=385.94.

Listed in Table 16 below are compounds of structure of formula (I), prepared according to the above procedure (General Method H).

TABLE 16

| Ex. No. | SM D-3 | SM A-1 | Compound of Formula (I) |
|---|---|---|---|
| 121 | D-3-1 | A-1-3 | (4-Methyl-2-[1,2,3]triazol-2-yl-phenyl)-[(S)-2-(5-phenyl-4H-[1,2,4]triazol-3-yl)-azetidin-1-yl]-methanone; LC-MS A: $t_R$ = 0.72 min; $[M + H]^+$ = 385.94 |
| 122 | D-3-5 | A-1-2 | {(S)-2-[5-(2-Ethoxy-pyridin-3-yl)-4H-[1,2,4]triazol-3-yl]-azetidin-1-yl}-(5-methyl-2-[1,2,3]triazol-2-yl-phenyl)-methanone; LC-MS A: $t_R$ = 0.74 min; $[M + H]^+$ = 431.13 |
| 123 | D-3-5 | A-1-3 | {(S)-2-[5-(2-Ethoxy-pyridin-3-yl)-4H-[1,2,4]triazol-3-yl]-azetidin-1-yl}-(4-methyl-2-[1,2,3]triazol-2-yl-phenyl)-methanone; LC-MS A: $t_R$ = 0.75 min; $[M + H]^+$ = 431.10 |
| 124 | D-3-2 | A-1-2 | {(S)-2-[5-(3-Chloro-2-methyl-phenyl)-4H-[1,2,4]triazol-3-yl]-azetidin-1-yl}-(5-methyl-2-[1,2,3]triazol-2-yl-phenyl)-methanone; LC-MS A: $t_R$ = 0.80 min; $[M(^{35}Cl) + H]^+$ = 433.88 |
| 125 | D-3-3 | A-1-2 | (5-Methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone; LC-MS A: $t_R$ = 0.65 min; $[M + H]^+$ = 470.13 |
| 126 | D-3-4 | A-1-2 | {(S)-2-[5-(3-Chloro-2-methoxy-phenyl)-4H-[1,2,4]triazol-3-yl]-azetidin-1-yl}-(5-methyl-2-[1,2,3]triazol-2-yl-phenyl)-methanone; LC-MS A: $t_R$ = 0.70 min; $[M(^{35}Cl) + H]^+$ = 450.10 |
| 127 | D-3-3 | A-1-3 | (4-Methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone; LC-MS A: $t_R$ = 0.67 min; $[M + H]^+$ = 470.12 |
| 128 | D-3-3 | A-1-6 | (4,5-Dimethyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone; LC-MS A: $t_R$ = 0.84 min; $[M + H]^+$ = 484.14 |
| 129 | D-3-3 | A-1-11 | (5-Methoxy-4-methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone; LC-MS A: $t_R$ = 0.84 min; $[M + H]^+$ = 500.07 |
| 130 | D-3-3 | A-1-15 | (5-Chloro-4-methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone; LC-MS A: $t_R$ = 0.86 min; $[M(^{35}Cl) + H]^+$ = 504.05 |
| 131 | D-3-3 | A-1-7 | (4-Chloro-5-methoxy-2-[1,2,3]triazol-2-yl-phenyl)-{(S)-2-[5-(2-trifluoromethoxy-phenyl)-4H-[1,2,4]triazol-3-yl]-azetidin-1-yl}-methanone; LC-MS A: $t_R$ = 0.85 min; $[M(^{35}Cl) + H]^+$ = 520.09 |
| 132 | D-3-3 | A-1-1 | (4-Chloro-2-[1,2,3]triazol-2-yl-phenyl)-{(S)-2-[5-(2-trifluoromethoxy-phenyl)-4H-[1,2,4]triazol-3-yl]-azetidin-1-yl}-methanone; LC-MS A: $t_R$ = 0.84 min; $[M(^{35}Cl) + H]^+$ = 490.05 |
| 133 | D-3-3 | A-1-10 | (2-[1,2,3]Triazol-2-yl-4-trifluoromethyl-phenyl)-{(S)-2-[5-(2-trifluoromethoxy-phenyl)-4H-[1,2,4]triazol-3-yl]-azetidin-1-yl}-methanone; LC-MS A: $t_R$ = 0.86 min; $[M + H]^+$ = 524.06 |
| 134 | D-3-3 | A-1-14 | (4-Methyl-biphenyl-2-yl)-{(S)-2-[5-(2-trifluoromethoxy-phenyl)-4H-[1,2,4]triazol-3-yl]-azetidin-1-yl}-methanone; LC-MS A: $t_R$ = 0.91 min; $[M + H]^+$ = 479.13 |
| 135 | D-3-3 | A-1-22 | (5-Methyl-2-pyrimidin-2-yl-phenyl)-{(S)-2-[5-(2-trifluoromethoxy-phenyl)-4H-[1,2,4]triazol-3-yl]-azetidin-1-yl}-methanone; LC-MS A: $t_R$ = 0.79 min; $[M + H]^+$ = 480.96 |

II. Biological Assays

Antagonistic activities on both orexin receptors have been measured for each example compound using the following procedure:

In Vitro Assay: Intracellular Calcium Measurements:

Chinese hamster ovary (CHO) cells expressing the human orexin-1 receptor and the human orexin-2 receptor, respectively, are grown in culture medium (Ham F-12 with L-Glutamine) containing 300 μg/mL G418, 100 U/mL penicillin, 100 μg/mL streptomycin and 10% heat inactivated fetal calf serum (FCS). The cells are seeded at 20,000 cells/well into 384-well black clear bottom sterile plates (Greiner). The seeded plates are incubated overnight at 37° C. in 5% $CO_2$. Human orexin-A as an agonist is prepared as 1 mM stock solution in MeOH:water (1:1), diluted in HBSS containing 0.1% bovine serum albumin (BSA), $NaHCO_3$: 0.375 g/L and 20 mM HEPES for use in the assay at a final concentration of 3 nM.

Antagonists are prepared as 10 mM stock solution in DMSO, then diluted in 384-well plates using DMSO followed by a transfer of the dilutions into in HBSS containing 0.1% bovine serum albumin (BSA), $NaHCO_3$: 0.375 g/L and 20 mM HEPES. On the day of the assay, 50 μL of staining buffer (HBSS containing 1% FCS, 20 mM HEPES, $NaHCO_3$: 0.375 g/L, 5 mM probenecid (Sigma) and 3 μM of the fluorescent calcium indicator fluo-4 AM (1 mM stock solution in DMSO, containing 10% pluronic) is added to each well. The 384-well cell-plates are incubated for 50 min at 37° C. in 5% $CO_2$ followed by equilibration at rt for 30 min before measurement.

Within the Fluorescent Imaging Plate Reader (FLIPR Tetra, Molecular Devices), antagonists are added to the plate in a volume of 10 μL/well, incubated for 120 min and finally 10 μL/well of agonist is added. Fluorescence is measured for each well at 1 second intervals, and the height of each fluorescence peak is compared to the height of the fluorescence peak induced by 3 nM orexin-A with vehicle in place of antagonist. The $IC_{50}$ value (the concentration of compound needed to inhibit 50% of the agonistic response) is determined and may be normalized using the obtained $IC_{50}$ value of an on-plate reference compound. Optimized conditions were achieved by adjustment of pipetting speed and cell splitting regime. The calculated $IC_{50}$ values may fluctuate depending on the daily cellular assay performance. Fluctuations of this kind are known to those skilled in the art. In the case where $IC_{50}$ values have been determined several times for the same compound, the geometric mean has been given. Antagonistic activities of example compounds are shown in Table 17.

TABLE 17

| Ex No. | $IC_{50}$ OX1 [nM] | $IC_{50}$ OX2 [nM] |
|---|---|---|
| 1 | 1220 | 19 |
| 2 | 713 | 9 |
| 3 | 2110 | 180 |
| 4 | 1300 | 38 |
| 5 | 1190 | 25 |
| 6 | 472 | 115 |
| 7 | 120 | 10 |
| 8 | 3430 | 115 |
| 9 | 134 | 10 |
| 10 | 335 | 17 |
| 11 | 2320 | 280 |
| 12 | 2490 | 187 |
| 13 | 1160 | 40 |
| 14 | 1040 | 40 |
| 15 | 116 | 15 |
| 16 | 641 | 17 |
| 17 | 439 | 9 |
| 18 | 160 | 5 |
| 19 | 44 | 9 |
| 20 | 634 | 33 |
| 21 | 173 | 4 |
| 22 | 821 | 23 |
| 23 | 1420 | 39 |

TABLE 17-continued

| Ex No. | IC$_{50}$ OX1 [nM] | IC$_{50}$ OX2 [nM] |
|---|---|---|
| 24 | 963 | 25 |
| 25 | 1750 | 27 |
| 26 | 2080 | 26 |
| 27 | 220 | 6 |
| 28 | 397 | 2 |
| 29 | 671 | 4 |
| 30 | 295 | 10 |
| 31 | 68 | 3 |
| 32 | 819 | 100 |
| 33 | 1500 | 27 |
| 34 | 238 | 5 |
| 35 | 292 | 71 |
| 36 | 3820 | 287 |
| 37 | 458 | 59 |
| 38 | 322 | 119 |
| 39 | 75 | 4 |
| 40 | 221 | 41 |
| 41 | 43 | 10 |
| 42 | 400 | 266 |
| 43 | 288 | 357 |
| 44 | 282 | 73 |
| 45 | 745 | 416 |
| 46 | 1020 | 115 |
| 47 | 618 | 727 |
| 48 | 960 | 239 |
| 49 | 223 | 305 |
| 50 | 583 | 91 |
| 51 | 276 | 342 |
| 52 | 357 | 309 |
| 53 | 1230 | 1190 |
| 54 | 129 | 10 |
| 55 | 1200 | 218 |
| 56 | 436 | 280 |
| 57 | 89 | 4 |
| 58 | 1030 | 133 |
| 59 | 43 | 7 |
| 60 | 1200 | 500 |
| 61 | 993 | 367 |
| 62 | 562 | 170 |
| 63 | 1130 | 448 |
| 64 | 812 | 69 |
| 65 | 2730 | 676 |
| 66 | 1600 | 390 |
| 67 | 437 | 631 |
| 68 | 1090 | 74 |
| 69 | 864 | 240 |
| 70 | 97 | 2 |
| 71 | 693 | 555 |
| 72 | 1400 | 666 |
| 73 | 383 | 20 |
| 74 | 578 | 6 |
| 75 | 378 | 12 |
| 76 | 909 | 11 |
| 77 | 616 | 28 |
| 78 | 646 | 22 |
| 79 | 338 | 17 |
| 80 | 756 | 49 |
| 81 | 338 | 47 |
| 82 | 171 | 10 |
| 83 | 167 | 13 |
| 84 | 103 | 11 |
| 85 | 34 | 3 |
| 86 | 193 | 4 |
| 87 | 1340 | 78 |
| 88 | 178 | 0.6 |
| 89 | 82 | 3 |
| 90 | 52 | 2 |
| 91 | 17 | 0.6 |
| 92 | 37 | 1 |
| 93 | 655 | 8 |
| 94 | 326 | 11 |
| 95 | 60 | 6 |
| 96 | 306 | 3 |
| 97 | 257 | 10 |
| 98 | 83 | 1 |
| 99 | 20 | 1 |
| 100 | 820 | 34 |
| 101 | 88 | 8 |
| 102 | 41 | 2 |
| 103 | 59 | 2 |
| 104 | 181 | 2 |
| 105 | 122 | 5 |
| 106 | 330 | 9 |
| 107 | 317 | 13 |
| 108 | 759 | 28 |
| 109 | 132 | 3 |
| 110 | 46 | 1 |
| 111 | 82 | 0.7 |
| 112 | 70 | 1 |
| 113 | 51 | 1 |
| 114 | 26 | 2 |
| 115 | 984 | 122 |
| 116 | 561 | 5 |
| 117 | 606 | 32 |
| 118 | 81 | 4 |
| 119 | 38 | 4 |
| 120 | 13400 | 450 |
| 121 | 9070 | 322 |
| 122 | 2300 | 92 |
| 123 | 2040 | 316 |
| 124 | 5880 | 238 |
| 125 | 2430 | 56 |
| 126 | 7230 | 170 |
| 127 | 866 | 11 |
| 128 | 414 | 9 |
| 129 | 454 | 6 |
| 130 | 245 | 5 |
| 131 | 497 | 5 |
| 132 | 315 | 16 |
| 133 | 364 | 17 |
| 134 | 563 | 39 |
| 135 | 2000 | 348 |

The invention claimed is:
1. A compound of formula (I)

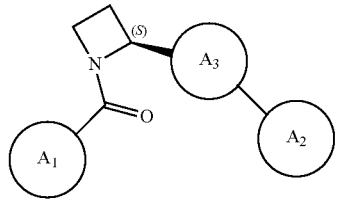

Formula (I)

wherein the carbon atom at position 2 of the azetidine ring is in absolute (S)-configuration;
ring A$_3$ represents a meta di-substituted 5-membered heteroarylene ring containing one, two or three heteroatoms; wherein at least one of said heteroatoms is nitrogen, and the remaining is/are independently selected from oxygen, sulfur and nitrogen;
ring A$_2$ represents phenyl or 6-membered heteroaryl; wherein said phenyl or 6-membered heteroaryl is independently unsubstituted, or mono-, di-, or tri-substituted; wherein the substituents are independently selected from (C$_{1-4}$)alkyl, (C$_{1-4}$)alkoxy, halogen, (C$_{1-3}$)fluoroalkyl, (C$_{1-3}$)fluoroalkoxy, and (C$_{3-6}$)cycloalkyl-oxy-;
ring A$_1$ represents phenyl or 5- or 6-membered heteroaryl, wherein said phenyl or 5- or 6-membered heteroaryl independently is mono-, di-, or tri-substituted; wherein one of said substituents is attached in ortho-position to the point of attachment of A$_1$ to the rest of the molecule; wherein said substituent is phenyl or 5- or 6-membered heteroaryl; wherein said phenyl or 5- or 6-membered heteroaryl substituent is independently unsubstituted, mono-, di-, or tri-substituted, wherein the substituents are independently selected from $(C_{1-4})$alkyl, $(C_{1-4})$alkoxy, halogen, $(C_{1-3})$fluoroalkyl, and $(C_{1-3})$fluoroalkoxy;

and the other of said substituents, if present, is/are independently selected from $(C_{1-4})$alkyl, $(C_{1-4})$alkoxy, halogen, $(C_{1-3})$fluoroalkyl, $(C_{1-3})$fluoroalkoxy and dimethylamino;

or a pharmaceutically acceptable salt thereof.

2. A compound according to claim 1; wherein the ring $A_3$ is a meta di-substituted 5-membered heteroarylene ring selected from oxadiazol-diyl, triazol-diyl, isoxazol-diyl, oxazol-diyl, thiazol-diyl, pyrazol-diyl, imidazol-diyl, isothiazol-diyl, and thiadiazol-diyl;

or a pharmaceutically acceptable salt thereof.

3. A compound according to claim 1; wherein the ring $A_3$ represents

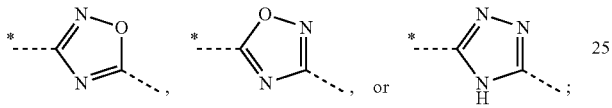

wherein the asterisks indicate the bond that is linked to the azetidin-2-yl moiety of the molecule;

or a pharmaceutically acceptable salt thereof.

4. A compound according to claim 1; wherein ring $A_2$ represents phenyl which is mono- or di-substituted; wherein the substituents are independently selected from $(C_{1-4})$alkyl, $(C_{1-4})$alkoxy, halogen, and $(C_{1-3})$fluoroalkoxy; or 6-membered heteroaryl containing one or two ring nitrogen atoms; wherein said heteroaryl is mono-substituted; wherein the substituent is selected from $(C_{1-4})$alkoxy and $(C_{3-6})$cycloalkyl-oxy-;

or a pharmaceutically acceptable salt thereof.

5. A compound according to claim 1; wherein the group $A_3$-$A_2$ represents a group independently selected from the following groups A, B and C:

A: [1,2,4]oxadiazol-3,5-diyl groups selected from the groups:

A.1

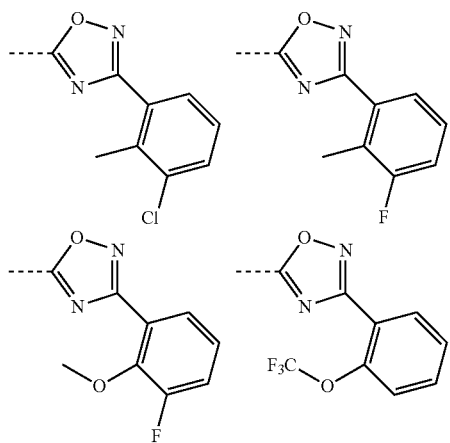

A.2

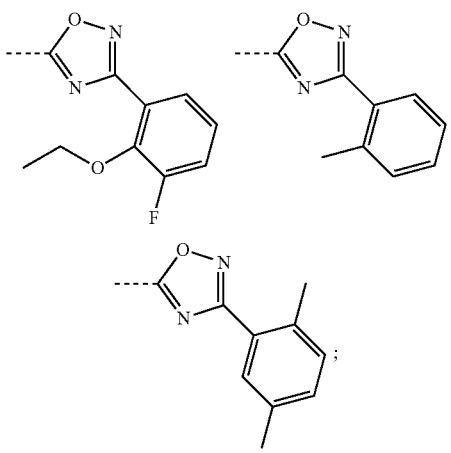

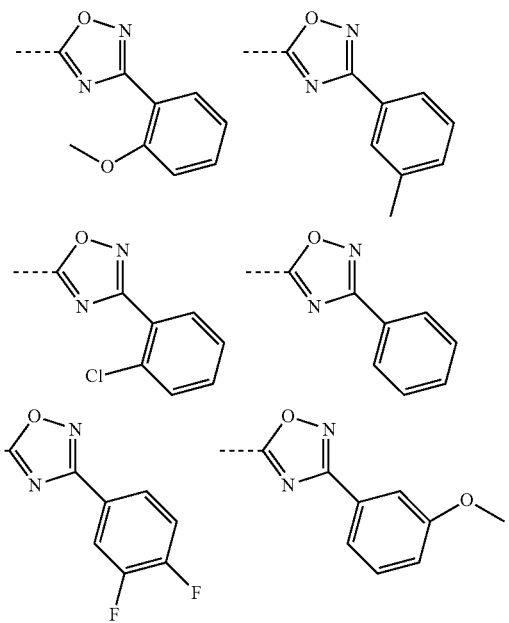

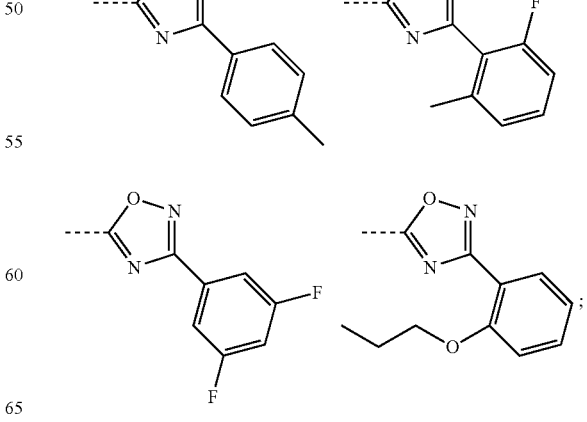

A.3

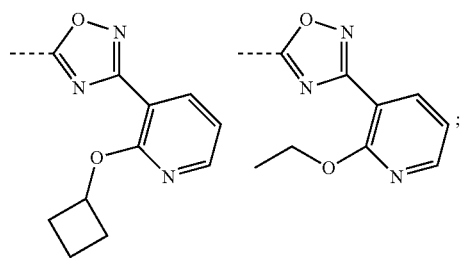

B: [1,2,4]oxadiazol-3,5-diyl groups selected from the groups:
B.1

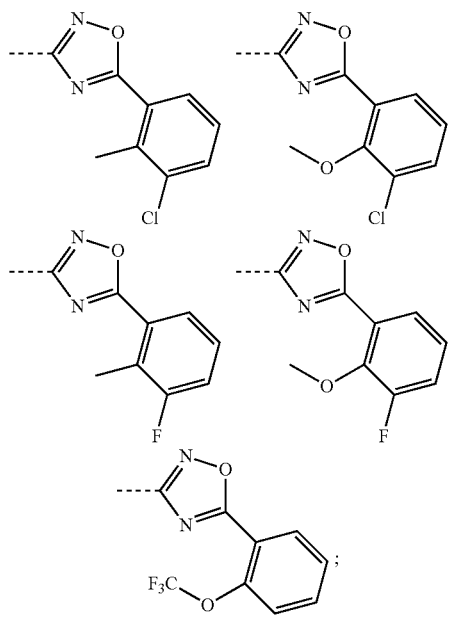

B.2

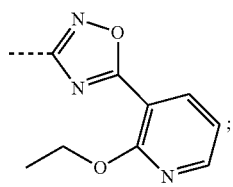

B.3

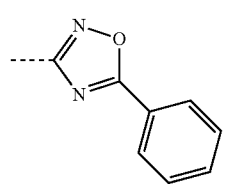

C: [1,2,4]triazol-3,5-diyl groups selected from the groups:
C.1

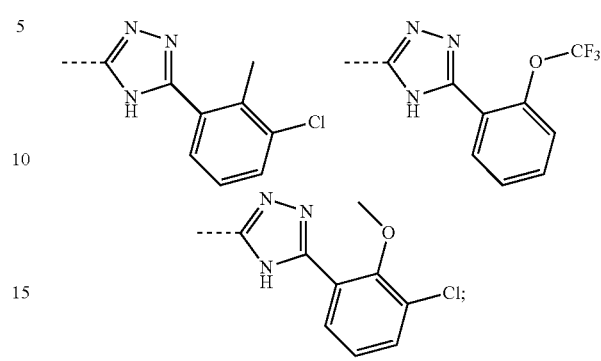

C.2

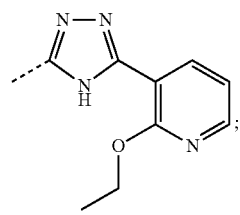

C.3

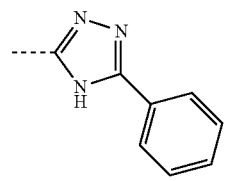

or a pharmaceutically acceptable salt thereof.

6. A compound according to claim 1; wherein one or both of the following characteristics are present:

in case ring $A_1$ represents a 5-membered heteroaryl group, such group is an oxazolyl or a thiazolyl group; and/or in case ring $A_1$ represents a 6-membered heteroaryl group, such group is a pyridinyl, a pyrazinyl, or a pyrimidinyl group;

or a pharmaceutically acceptable salt thereof.

7. A compound according to claim 1; wherein one or more of the following characteristics are present:

in case said ortho substituent of ring $A_1$ represents a 5-membered heteroaryl group, such group is an unsubstituted [1,2,3]triazol-2-yl] group; and/or in case said ortho substituent of ring $A_1$ represents a 6-membered heteroaryl group, such group is an unsubstituted pyrimidin-2-yl group; and/or in case said ortho substituent of ring $A_1$ represents a phenyl group, such group is an unsubstituted or mono-substituted phenyl group wherein the substituent is selected from $(C_{1-4})$alkyl, $(C_{1-4})$alkoxy, and halogen;

or a pharmaceutically acceptable salt thereof.

8. A compound according to claim 1; wherein ring $A_1$ represents a group

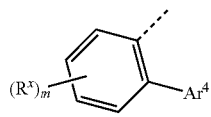

wherein $(R^x)_m$ represents one or two substituents independently selected from $(C_{1-4})$alkyl, $(C_{1-4})$alkoxy, halogen, $(C_{1-3})$fluoroalkyl, and $(C_{1-3})$fluoroalkoxy; and $Ar^4$ represents unsubstituted or mono-substituted phenyl wherein the substituent is selected from the group consisting of $(C_{1-4})$alkyl, $(C_{1-4})$alkoxy, and halogen; unsubstituted [1,2,3]triazol-2-yl; unsubstituted pyrazol-1-yl; unsubstituted pyridin-2-yl; or unsubstituted pyrimidin-2-yl;

or a pharmaceutically acceptable salt thereof.

9. A compound according to claim 1; wherein the ring $A_1$ represents a group selected from the following groups A and B:

A: substituted phenyl groups selected from the groups:

A.1

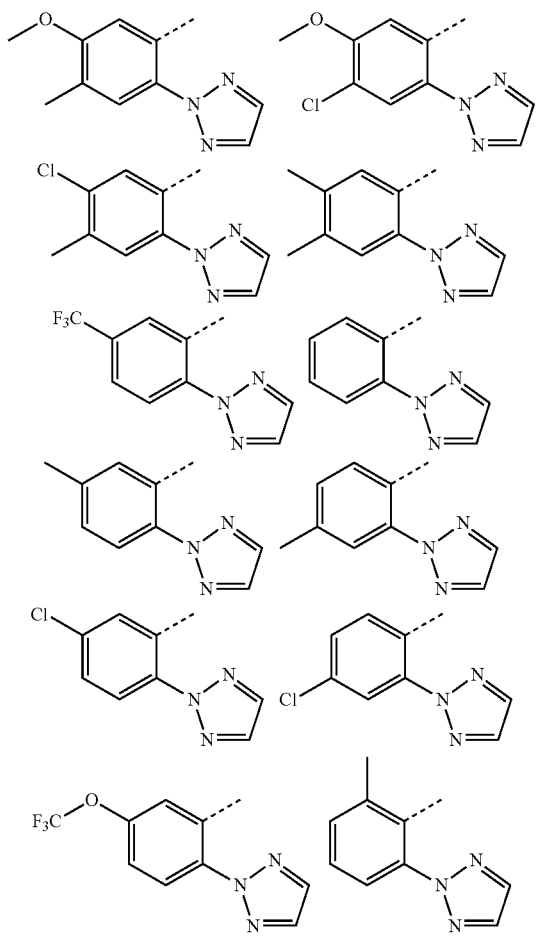

A.2

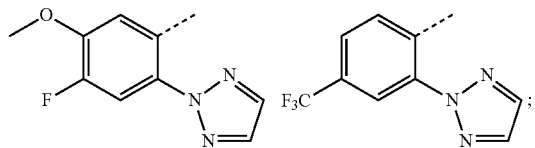

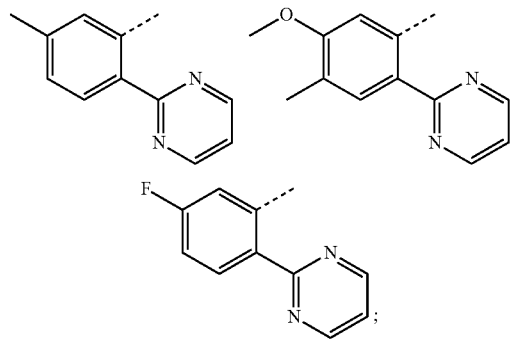

A.3

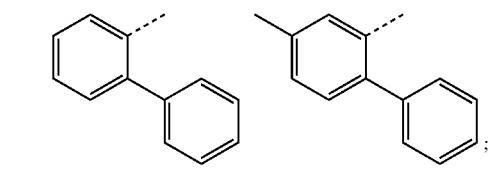

B: substituted 5-membered heteroaryl groups selected from the groups:

B.1

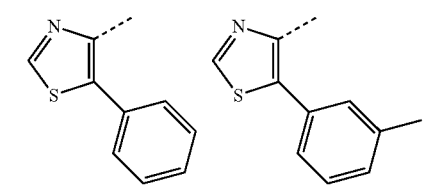

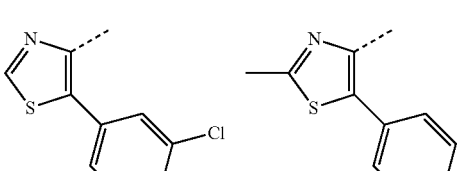

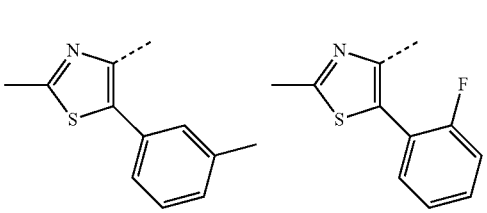

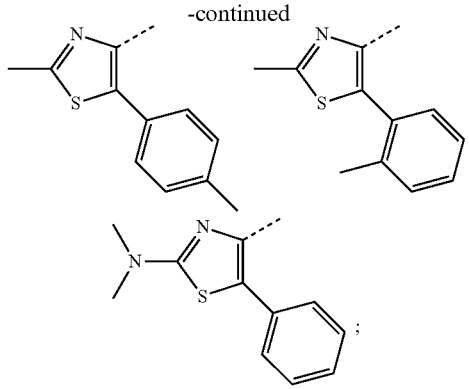

B.2

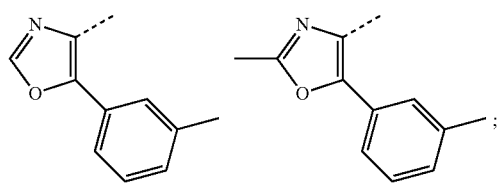

or a pharmaceutically acceptable salt thereof.

10. A compound according to claim 1 selected from:

(5-Methyl-2-[1,2,3]triazol-2-yl-phenyl)-[(S)-2-(3-o-tolyl-[1,2,4]oxadiazol-5-yl)-azetidin-1-yl]-methanone;

{(S)-2-[3-(3-Fluoro-2-methyl-phenyl)-[1,2,4]oxadiazol-5-yl]-azetidin-1-yl}-(5-methyl-2-[1,2,3]triazol-2-yl-phenyl)-methanone;

{(S)-2[3-(2-Methoxy-phenyl)-[1,2,4]oxadiazol-5-yl]-azetidin-1-yl}-(5-methyl-2-[1,2,3]triazol-2-yl-phenyl)-methanone;

{(S)-2[3-(3-Methoxy-phenyl)-[1,2,4]oxadiazol-5-yl]-azetidin-1-yl}-(5-methyl-2-[1,2,3]triazol-2-yl-phenyl)-methanone;

{(S)-2-[3-(3-Chloro-2-methyl-phenyl)-[1,2,4]oxadiazol-5-yl]-azetidin-1-yl}-(5-methyl-2-[1,2,3]triazol-2-yl-phenyl)-methanone;

{(S)-2-[3-(2-Ethoxy-3-fluoro-phenyl)-[1,2,4]oxadiazol-5-yl]-azetidin-1-yl}-(5-methyl-2-[1,2,3]triazol-2-yl-phenyl)-methanone;

{(S)-2-[3-(2,5-Dimethyl-phenyl)-[1,2,4]oxadiazol-5-yl]-azetidin-1-yl}-(5-methyl-2-[1,2,3]triazol-2-yl-phenyl)-methanone;

(5-Methyl-2-[1,2,3]triazol-2-yl-phenyl)-[(S)-2-(3-m-tolyl-[1,2,4]oxadiazol-5-yl)-azetidin-1-yl]-methanone;

{(S)-2-[3-(2-Chloro-phenyl)-[1,2,4]oxadiazol-5-yl]-azetidin-1-yl}-(5-methyl-2-[1,2,3]triazol-2-yl-phenyl)-methanone;

(5-Methyl-2-[1,2,3]triazol-2-yl-phenyl)-{(S)-2[3-(2-trifluoromethoxy-phenyl)-[1,2,4]oxadiazol-5-yl]-azetidin-1-yl}-methanone;

{(S)-2-[3-(3-Fluoro-2-methoxy-phenyl)-[1,2,4]oxadiazol-5-yl]-azetidin-1-yl}-(5-methyl-2-[1,2,3]triazol-2-yl-phenyl)-methanone;

{(S)-2[3-(3-Fluoro-2-methoxy-phenyl)-[1,2,4]oxadiazol-5-yl]-azetidin-1-yl}-(5-methoxy-4-methyl-2-[1,2,3]triazol-2-yl-phenyl)-methanone;

(4,5-Dimethyl-2-[1,2,3]triazol-2-yl-phenyl)-{(S)-2-[3-(3-fluoro-2-methoxy-phenyl)-[1,2,4]oxadiazol-5-yl]-azetidin-1-yl}-methanone;

(4,5-Dimethyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Fluoro-2-methoxy-phenyl)-[1,2,4]oxadiazol-5-yl]-azetidin-1-yl}-(4-methyl-2-[1,2,3]triazol-2-yl-phenyl)-methanone;

(4,5-Dimethyl-2-[1,2,3]triazol-2-yl-phenyl)-{(S)-2-[3-(3-fluoro-2-methyl-phenyl)-[1,2,4]oxadiazol-5-yl]-azetidin-1-yl}-methanone;

{(S)-2-[3-(3-Fluoro-2-methyl-phenyl)-[1,2,4]oxadiazol-5-yl]-azetidin-1-yl}-(4-methyl-2-[1,2,3]triazol-2-yl-phenyl)-methanone;

(4-Fluoro-5-methoxy-2-[1,2,3]triazol-2-yl-phenyl)-{(S)-2[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(4-fluoro-5-methoxy-2-[1,2,3]triazol-2-yl-phenyl)-methanone;

(4-Fluoro-5-methoxy-2-[1,2,3]triazol-2-yl-phenyl)-{(S)-2-[3-(3-fluoro-2-methyl-phenyl)-[1,2,4]oxadiazol-5-yl]-azetidin-1-yl}-methanone;

{(S)-2[3-(3-Fluoro-2-methoxy-phenyl)-[1,2,4]oxadiazol-5-yl]-azetidin-1-yl}-(4-fluoro-5-methoxy-2-[1,2,3]triazol-2-yl-phenyl)-methanone;

(5-Methoxy-4-methyl-2-[1,2,3]triazol-2-yl-phenyl)-{(S)-2[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(5-methoxy-4-methyl-2-[1,2,3]triazol-2-yl-phenyl)-methanone;

{(S)-2-[3-(3-Fluoro-2-methyl-phenyl)-[1,2,4]oxadiazol-5-yl]-azetidin-1-yl}-(5-methoxy-4-methyl-2-[1,2,3]triazol-2-yl-phenyl)-methanone;

{(S)-2-[3-(2-Ethoxy-pyridin-3-yl)-[1,2,4]oxadiazol-5-yl]-azetidin-1-yl}-(5-methyl-2-[1,2,3]triazol-2-yl-phenyl)-methanone;

(4,5-Dimethyl-2-[1,2,3]triazol-2-yl-phenyl)-{(S)-2-[3-(2-ethoxy-pyridin-3-yl)-[1,2,4]oxadiazol-5-yl]-azetidin-1-yl}-methanone;

{(S)-2-[3-(2-Ethoxy-pyridin-3-yl)-[1,2,4]oxadiazol-5-yl]-azetidin-1-yl}-(4-fluoro-5-methoxy-2-[1,2,3]triazol-2-yl-phenyl)-methanone;

{(S)-2-[3-(2-Ethoxy-pyridin-3-yl)-[1,2,4]oxadiazol-5-yl]-azetidin-1-yl}-(5-methoxy-4-methyl-2-[1,2,3]triazol-2-yl-phenyl)-methanone;

(4-Methyl-biphenyl-2-yl)-{(S)-2-[3-(2-trifluoromethoxy-phenyl)-[1,2,4]oxadiazol-5-yl]-azetidin-1-yl}-methanone;

(2-Methyl-5-phenyl-thiazol-4-yl)-{(S)-2-[3-(2-trifluoromethoxy-phenyl)-[1,2,4]oxadiazol-5-yl]-azetidin-1-yl}-methanone;

(2-Dimethylamino-5-phenyl-thiazol-4-yl)-{(S)-2-[3-(2-trifluoromethoxy-phenyl)-[1,2,4]oxadiazol-5-yl]-azetidin-1-yl}-methanone;

Biphenyl-2-yl-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(4-methyl-biphenyl-2-yl)-methanone;

{(S)-2-[3-(3-Chloro-2-methyl-phenyl)-[1,2,4]oxadiazol-5-yl]-azetidin-1-yl}-(2-dimethylamino-5-phenyl-thiazol-4-yl)-methanone;

{(S)-2-[3-(3-Chloro-2-methyl-phenyl)-[1,2,4]oxadiazol-5-yl]-azetidin-1-yl}-(4,5-dimethyl-2-[1,2,3]triazol-2-yl-phenyl)-methanone;

Biphenyl-2-yl-{(S)-2-[3-(3-chloro-2-methyl-phenyl)-[1,2,4]oxadiazol-5-yl]-azetidin-1-yl}-methanone;

(4-Chloro-5-methoxy-2-[1,2,3]triazol-2-yl-phenyl)-{(S)-2-[3-(3-chloro-2-methyl-phenyl)-[1,2,4]oxadiazol-5-yl]-azetidin-1-yl}-methanone;

(4-Chloro-5-methoxy-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(4-chloro-2-[1,2,3]triazol-2-yl-phenyl)-methanone;

(4-Chloro-2-[1,2,3]triazol-2-yl-phenyl)-{(S)-2[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(4-methyl-2-[1,2,3]triazol-2-yl-phenyl)-methanone;

(4-Methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(5-chloro-2-[1,2,3]triazol-2-yl-phenyl)-methanone;

(5-Chloro-2-[1,2,3]triazol-2-yl-phenyl)-{(S)-2[3-(2-trifluoromethoxy-phenyl)-[1,2,4]oxadiazol-5-yl]-azetidin-1-yl}-methanone;

{(S)-2-[3-(3-Chloro-2-methyl-phenyl)-[1,2,4]oxadiazol-5-yl]-azetidin-1-yl}-(5-chloro-4-methyl-2-[1,2,3]triazol-2-yl-phenyl)-methanone;

(5-Chloro-4-methyl-2-[1,2,3]triazol-2-yl-phenyl)-{(S)-2-[3-(2-trifluoromethoxy-phenyl)-[1,2,4]oxadiazol-5-yl]-azetidin-1-yl}-methanone;

(5-Methyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

(4,5-Dimethyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

(5-Methoxy-4-methyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

{(S)-2-[5-(3-Fluoro-2-methoxy-phenyl)-[1,2,4]oxadiazol-3-yl]-azetidin-1-yl}-(5-methoxy-4-methyl-2-[1,2,3]triazol-2-yl-phenyl)-methanone;

(4,5-Dimethyl-2-[1,2,3]triazol-2-yl-phenyl)-{(S)-2-[5-(3-fluoro-2-methyl-phenyl)-[1,2,4]oxadiazol-3-yl]-azetidin-1-yl}-methanone;

{(S)-2-[5-(2-Ethoxy-pyridin-3-yl)-[1,2,4]oxadiazol-3-yl]-azetidin-1-yl}-(5-methyl-2-[1,2,3]triazol-2-yl-phenyl)-methanone;

(4,5-Dimethyl-2-[1,2,3]triazol-2-yl-phenyl)-{(S)-2-[5-(2-ethoxy-pyridin-3-yl)-[1,2,4]oxadiazol-3-yl]-azetidin-1-yl}-methanone;

{(S)-2-[5-(2-Ethoxy-pyridin-3-yl)-[1,2,4]oxadiazol-3-yl]-azetidin-1-yl}-(5-methoxy-4-methyl-2-[1,2,3]triazol-2-yl-phenyl)-methanone;

{(S)-2-[5-(3-Fluoro-2-methyl-phenyl)-[1,2,4]oxadiazol-3-yl]-azetidin-1-yl}-(5-methyl-2-[1,2,3]triazol-2-yl-phenyl)-methanone;

(4-Chloro-5-methoxy-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

(5-Chloro-4-methyl-2-[1,2,3]triazol-2-yl-phenyl)-{(S)-2-[5-(2-trifluoromethoxy-phenyl)-[1,2,4]oxadiazol-3-yl]-azetidin-1-yl}-methanone;

(4-Chloro-5-methoxy-2-[1,2,3]triazol-2-yl-phenyl)-{(S)-2-[5-(3-fluoro-2-methyl-phenyl)-[1,2,4]oxadiazol-3-yl]-azetidin-1-yl}-methanone;

{(S)-2-[5-(2-Ethoxy-pyridin-3-yl)-[1,2,4]oxadiazol-3-yl]-azetidin-1-yl}-(4-methyl-2-[1,2,3]triazol-2-yl-phenyl)-methanone;

(4-Chloro-5-methoxy-2-[1,2,3]triazol-2-yl-phenyl)-{(S)-2-[5-(2-ethoxy-pyridin-3-yl)-[1,2,4]oxadiazol-3-yl]-azetidin-1-yl}-methanone;

(5-Chloro-4-methyl-2-[1,2,3]triazol-2-yl-phenyl)-{(S)-2-[5-(2-ethoxy-pyridin-3-yl)-[1,2,4]oxadiazol-3-yl]-azetidin-1-yl}-methanone;

{(S)-2-[5-(3-Chloro-2-methyl-phenyl)-[1,2,4]oxadiazol-3-yl]-azetidin-1-yl}-(2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(5-methyl-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(4,5-dimethyl-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(5-methoxy-4-methyl-2-[1,2,3]triazol-2-yl-phenyl)-methanone;

(4-Chloro-5-methoxy-2-[1,2,3]triazol-2-yl-phenyl)-{(S)-2-[5-(3-chloro-2-methyl-phenyl)-[1,2,4]oxadiazol-3-yl]-azetidin-1-yl}-methanone;

{(S)-2-[5-(3-Chloro-2-methyl-phenyl)-[1,2,4]oxadiazol-3-yl]-azetidin-1-yl}-(5-chloro-4-methyl-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(4-methyl-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(4-chloro-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(2-[1,2,3]triazol-2-yl-4-trifluoromethyl-phenyl)-methanone;

{(S)-2-[5-(3-Chloro-2-methoxy-phenyl)-[1,2,4]oxadiazol-3-yl]-azetidin-1-yl}-(5-methyl-2-[1,2,3]triazol-2-yl-phenyl)-methanone;

{(S)-2-[5-(3-Chloro-2-methoxy-phenyl)-[1,2,4]oxadiazol-3-yl]-azetidin-1-yl}-(4,5-dimethyl-2-[1,2,3]triazol-2-yl-phenyl)-methanone;

{(S)-2-[5-(3-Chloro-2-methoxy-phenyl)-[1,2,4]oxadiazol-3-yl]-azetidin-1-yl}-(5-methoxy-4-methyl-2-[1,2,3]triazol-2-yl-phenyl)-methanone;

{(S)-2-[5-(3-Chloro-2-methoxy-phenyl)-[1,2,4]oxadiazol-3-yl]-azetidin-1-yl}-(4-chloro-5-methoxy-2-[1,2,3]triazol-2-yl-phenyl)-methanone;

{(S)-2-[5-(3-Chloro-2-methoxy-phenyl)-[1,2,4]oxadiazol-3-yl]-azetidin-1-yl}-(5-chloro-4-methyl-2-[1,2,3]triazol-2-yl-phenyl)-methanone;

{(S)-2-[5-(3-Chloro-2-methyl-phenyl)-[1,2,4]oxadiazol-3-yl]-azetidin-1-yl}-(4-methyl-biphenyl-2-yl)-methanone;

{(S)-2-[5-(3-Chloro-2-methyl-phenyl)-[1,2,4]oxadiazol-3-yl]-azetidin-1-yl}-(5-methoxy-4-methyl-2-pyrimidin-2-yl-phenyl)-methanone;

{(S)-2-[5-(3-Chloro-2-methyl-phenyl)-[1,2,4]oxadiazol-3-yl]-azetidin-1-yl}-(5-methyl-2-pyrimidin-2-yl-phenyl)-methanone;

{(S)-2-[5-(3-Chloro-2-methoxy-phenyl)-[1,2,4]oxadiazol-3-yl]-azetidin-1-yl}-(4-methyl-2-[1,2,3]triazol-2-yl-phenyl)-methanone;

{(S)-2-[5-(3-Chloro-2-methoxy-phenyl)-[1,2,4]oxadiazol-3-yl]-azetidin-1-yl}-(4-chloro-2-[1,2,3]triazol-2-yl-phenyl)-methanone;

(4-Methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(4,5-Dimethyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(5-Methoxy-4-methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(5-Chloro-4-methyl-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(4-Chloro-5-methoxy-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(4-Chloro-2-[1,2,3]triazol-2-yl-phenyl)-{(S)-2-[5-(2-trifluoromethoxy-phenyl)-4H-[1,2,4]triazol-3-yl]-azetidin-1-yl}-methanone;

(2-[1,2,3]Triazol-2-yl-4-trifluoromethyl-phenyl)-{(S)-2-[5-(2-trifluoromethoxy-phenyl)-4H-[1,2,4]triazol-3-yl]-azetidin-1-yl}-methanone; and (4-Methyl-biphenyl-2-yl)-{(S)-2-[5-(2-trifluoromethoxy-phenyl)-4H-[1,2,4]triazol-3-yl]-azetidin-1-yl}-methanone;

or a pharmaceutically acceptable salt thereof.

11. A pharmaceutical composition comprising, as active principle, one or more compounds according to claim 1, or a pharmaceutically acceptable salt thereof, and at least one therapeutically inert excipient.

12. A method of treatment of sleep disorders, anxiety disorders, addiction disorders, cognitive dysfunctions, mood disorders, and appetite disorders; comprising administering to a patient an effective amount of a compound as defined in claim 1, or a pharmaceutically acceptable salt thereof.

\* \* \* \* \*